(12) United States Patent
Cummins et al.

(10) Patent No.: US 12,207,807 B2
(45) Date of Patent: Jan. 28, 2025

(54) DEVICES AND METHODS FOR TREATING A VESSEL IN A SUBJECT

(71) Applicant: National University of Ireland, Galway, Galway (IE)

(72) Inventors: Sean Cummins, County Limerick (IE); Nigel Phelan, Lucan (IE); Stephen Cox, Dublin (IE); Martin O'Halloran, Corandulla (IE)

(73) Assignee: University of Galway, Galway (IE)

( * ) Notice: Subject to any disclaimer, the term of this patent is extended or adjusted under 35 U.S.C. 154(b) by 0 days.

(21) Appl. No.: 17/547,723

(22) Filed: Dec. 10, 2021

(65) Prior Publication Data
US 2022/0133286 A1 May 5, 2022

Related U.S. Application Data

(63) Continuation of application No. 16/416,838, filed on May 20, 2019, now Pat. No. 11,903,570.

(30) Foreign Application Priority Data

May 18, 2018 (EP) .................................. 18173170

(51) Int. Cl.
*A61B 17/00* (2006.01)
*A61B 17/3207* (2006.01)
(Continued)

(52) U.S. Cl.
CPC .... *A61B 17/00008* (2013.01); *A61B 17/3207* (2013.01); *A61B 17/320758* (2013.01);
(Continued)

(58) Field of Classification Search
CPC .......... A61B 17/00008; A61B 17/3205; A61B 17/3207; A61B 17/320758;
(Continued)

(56) References Cited

U.S. PATENT DOCUMENTS

| | | | | |
|---|---|---|---|---|
| 4,935,025 A | * | 6/1990 | Bundy | A61B 10/04 600/564 |
| 5,011,489 A | * | 4/1991 | Salem | A61B 17/00008 606/159 |

(Continued)

FOREIGN PATENT DOCUMENTS

| | | |
|---|---|---|
| EP | 0501772 A1 | 9/1992 |
| EP | 3326553 A1 | 5/2018 |

(Continued)

OTHER PUBLICATIONS

Hocking et al. "Detrimental Effects of Mechanical Stretch on Smooth Muscle Function in Saphenous Veins".
(Continued)

*Primary Examiner* — Martin T Ton
(74) *Attorney, Agent, or Firm* — Bookoff McAndrews, PLLC

(57) ABSTRACT

A method of treating a vessel in a subject comprises the steps of advancing a device distally across a treatment zone in a vessel, wherein the device comprises an elongated catheter having a lumen and a distal end, and a radially expansive treatment element disposed in the lumen and configured for axial movement relative to the catheter; deploying the radially expansive treatment element proud of the distal end of the catheter to radially expand and circumferentially impress against the vessel lumen at a distal end of the treatment zone; and withdrawing the deployed radially expansive treatment element proximally along the treatment zone with the treatment element circumferentially impressed against the vessel lumen to mechanically and circumferentially denude the treatment zone of the vessel. The radially expansive treatment element is then recaptured into the lumen of the catheter, before the device is withdrawn from the treated vessel.

26 Claims, 65 Drawing Sheets

(51) Int. Cl.
*A61B 18/14* (2006.01)
*A61B 17/12* (2006.01)
*A61B 17/22* (2006.01)
*A61B 17/32* (2006.01)
*A61B 18/00* (2006.01)
*A61M 25/00* (2006.01)

(52) U.S. Cl.
CPC ............. *A61B 18/1492* (2013.01); *A61B 2017/00778* (2013.01); *A61B 2017/00867* (2013.01); *A61B 17/1204* (2013.01); *A61B 17/12109* (2013.01); *A61B 17/12136* (2013.01); *A61B 2017/22065* (2013.01); *A61B 2017/320004* (2013.01); *A61B 2017/320008* (2013.01); *A61B 2017/320733* (2013.01); *A61B 2017/320741* (2013.01); *A61B 2018/00404* (2013.01); *A61M 25/0082* (2013.01)

(58) Field of Classification Search
CPC ....... A61B 2017/320004; A61B 2017/320008; A61B 2017/320012; A61B 17/320708; A61B 17/320725; A61M 2025/1086; A61M 2025/109
See application file for complete search history.

(56) References Cited

U.S. PATENT DOCUMENTS

| | | | |
|---|---|---|---|
| 6,402,745 B1 | 6/2002 | Wilk | |
| 8,696,645 B2 | 4/2014 | Tal et al. | |
| RE46,581 E * | 10/2017 | Lafontaine | ..... A61B 17/320725 |
| 2002/0010489 A1* | 1/2002 | Grayzel | ................ A61F 2/958 |
| | | | 606/194 |
| 2002/0029052 A1* | 3/2002 | Evans | ................... A61M 29/02 |
| | | | 606/159 |
| 2005/0080448 A1 | 4/2005 | Kear et al. | |
| 2005/0085836 A1* | 4/2005 | Raymond | ........ A61B 17/12022 |
| | | | 606/159 |
| 2006/0085054 A1 | 4/2006 | Zikorus et al. | |
| 2006/0195137 A1 | 8/2006 | Sepetka et al. | |
| 2007/0239199 A1* | 10/2007 | Jayaraman | ................ A61F 2/01 |
| | | | 606/200 |
| 2007/0248640 A1 | 10/2007 | Karabey et al. | |
| 2007/0270893 A1* | 11/2007 | Pikus | .............. A61B 17/00008 |
| | | | 606/159 |
| 2008/0249420 A1* | 10/2008 | Crossman | ......... A61M 25/1002 |
| | | | 604/523 |
| 2009/0054918 A1 | 2/2009 | Henson | |
| 2009/0209987 A1 | 8/2009 | Mathews et al. | |
| 2011/0046543 A1 | 2/2011 | Brandeis | |
| 2012/0226304 A1* | 9/2012 | Ryan | ................ A61B 17/12145 |
| | | | 606/200 |
| 2013/0338689 A1* | 12/2013 | Gadalean | ....... A61B 17/320725 |
| | | | 606/159 |
| 2014/0276388 A1* | 9/2014 | Allen | ............... A61B 17/12109 |
| | | | 604/93.01 |
| 2014/0276921 A1 | 9/2014 | Bates et al. | |
| 2016/0030023 A1 | 2/2016 | Hayakawa et al. | |
| 2016/0030068 A1 | 2/2016 | Hayakawa et al. | |
| 2016/0030719 A1 | 2/2016 | Hayakawa et al. | |
| 2016/0038174 A1 | 2/2016 | Bruzzi et al. | |
| 2016/0242790 A1 | 8/2016 | Brandeis | |
| 2017/0056048 A1 | 3/2017 | Erpen | |

FOREIGN PATENT DOCUMENTS

| | | |
|---|---|---|
| GB | 2519057 | 4/2015 |
| JP | 2016034485 A | 3/2016 |
| WO | WO 2004/112569 A2 | 12/2004 |
| WO | WO 2014/140325 A1 | 9/2014 |
| WO | WO 2016/102930 A2 | 6/2016 |
| WO | WO 2017/194698 A2 | 11/2017 |

OTHER PUBLICATIONS

Michael G. Tal et al., "Histologic findings after mechanochemical ablation in a caprine model with use of ClariVein", Journal of Vascular Surgery: Venous and Lymphatic Disorders, Jan. 2015, vol. 3, No. 1, (pp. 81-85).

Michael Kendler et al., "Histology of saphenous veins after treatment with the ClariVein device—an ex-vivo experiment", Journal of the German Society of Dermatology (2013) (5 pages).

D. Boersma et al., "Macroscopic and Histologic Analysis of Vessel Wall Reaction After Mechanochemical Endovenous Ablation Using the ClariVein OC Device in an Animal Model", European Journal of Vascular and Endovascular Surgery, http://dx.doi.org/101016/j.ejvs.2016.11.024 (2016) (9 pages).

Office Action in U.S. Appl. No. 17/056,040, dated Oct. 13, 2023, (27 pages).

* cited by examiner

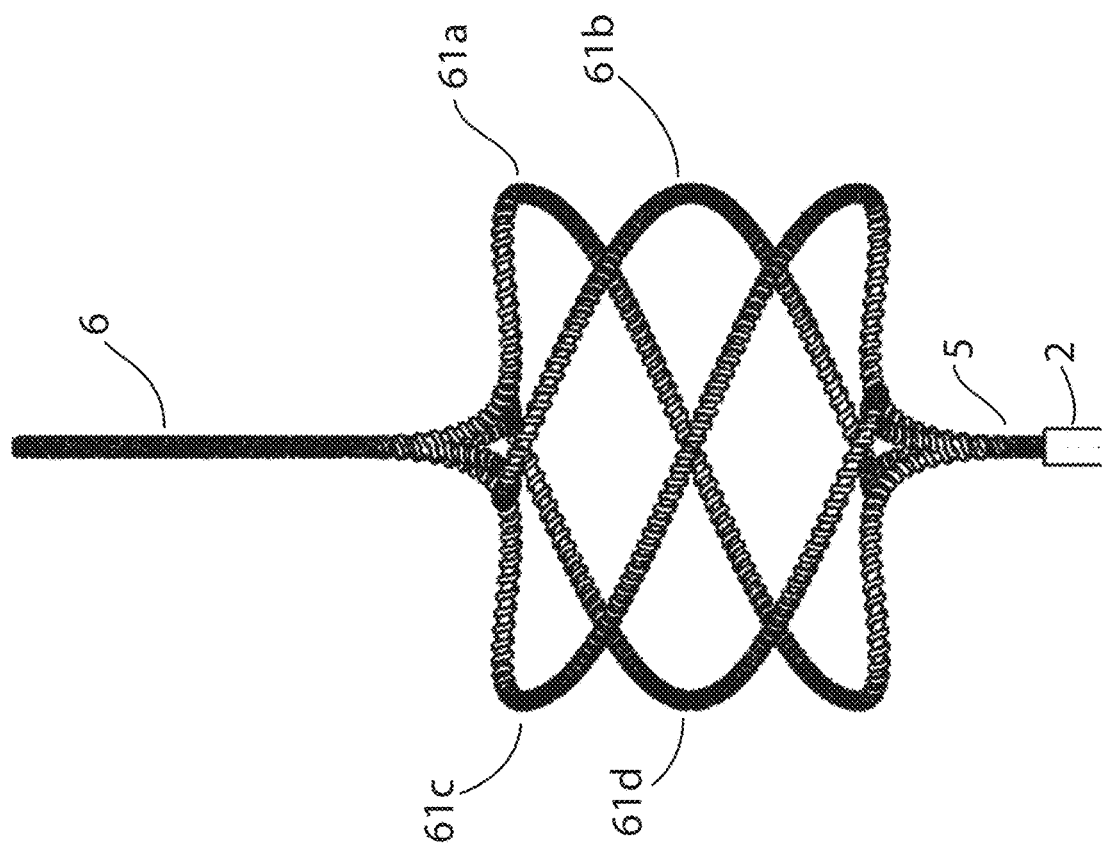

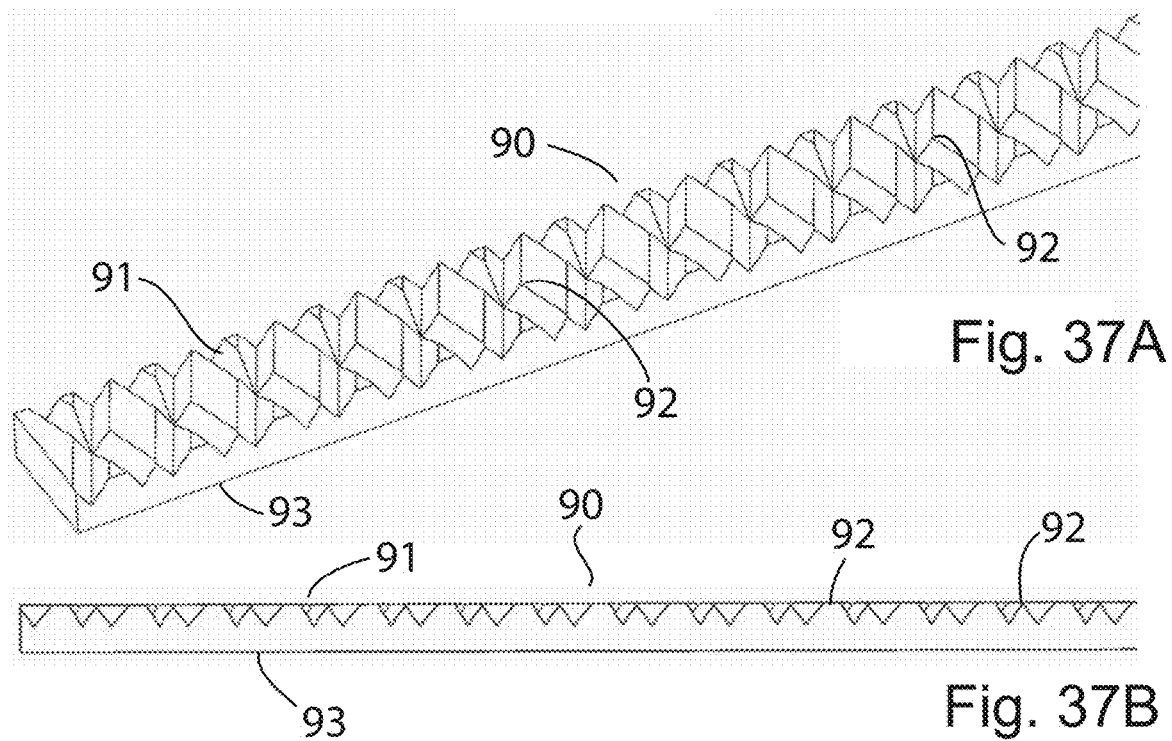
Fig. 37A
Fig. 37B
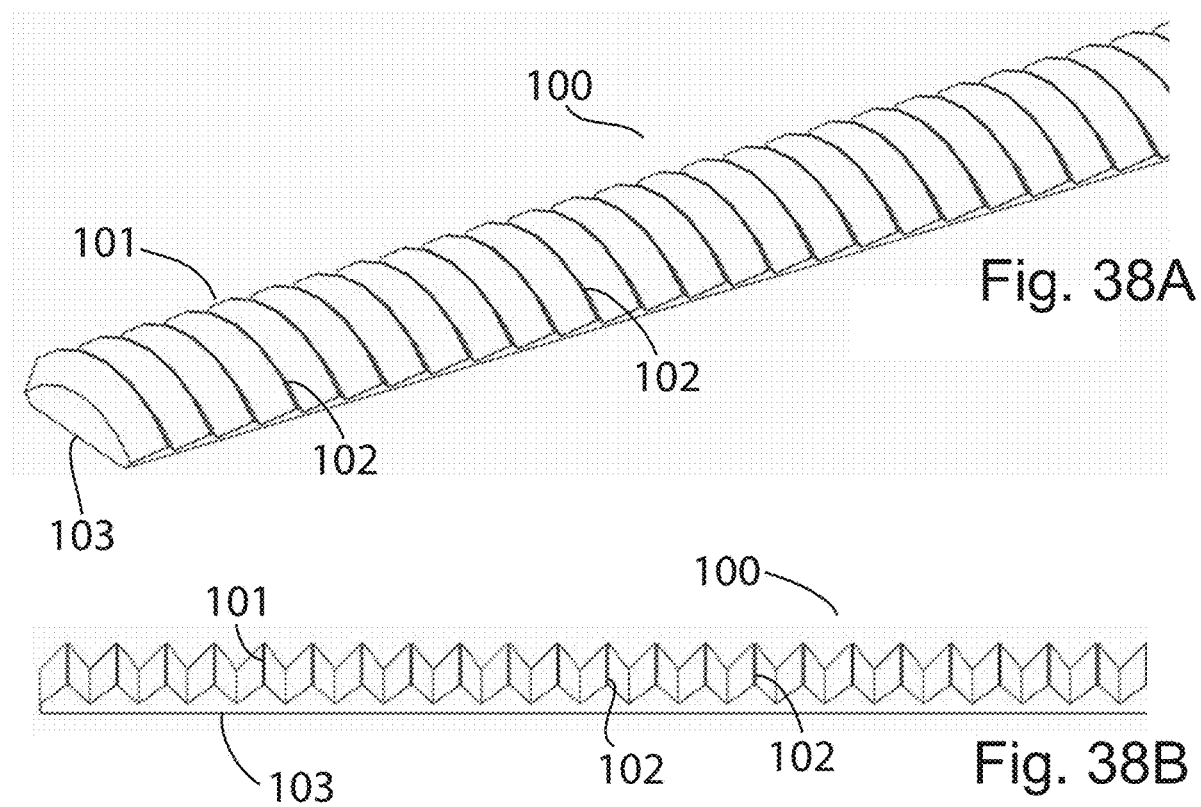
Fig. 38A
Fig. 38B

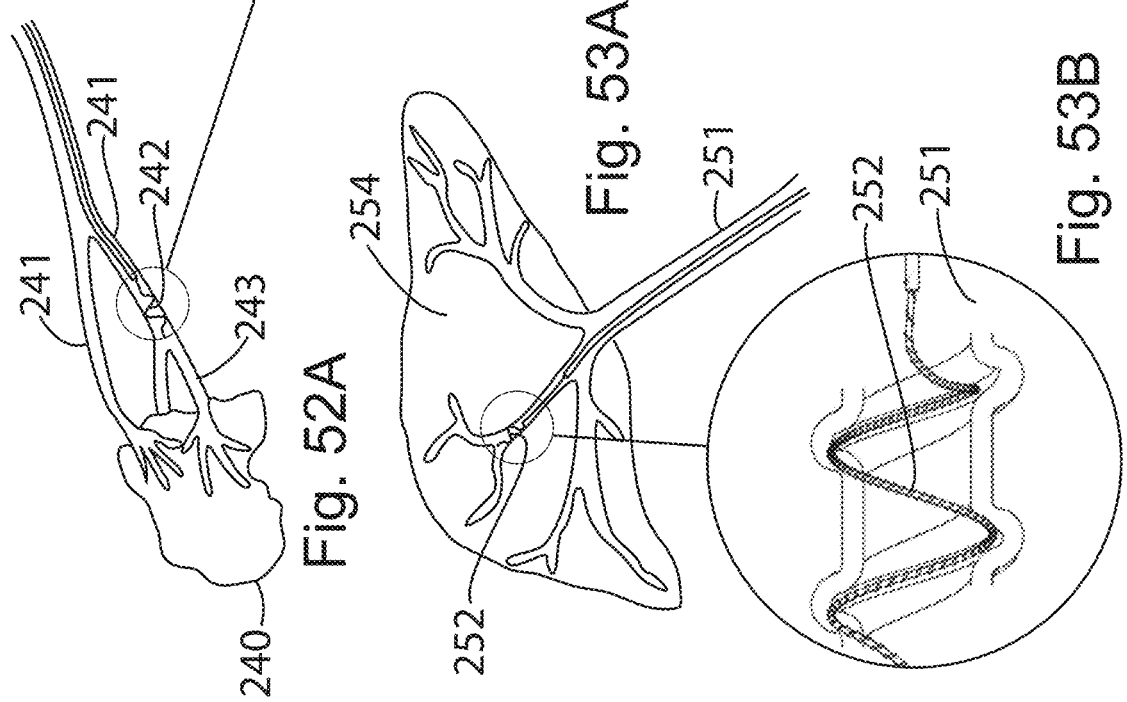

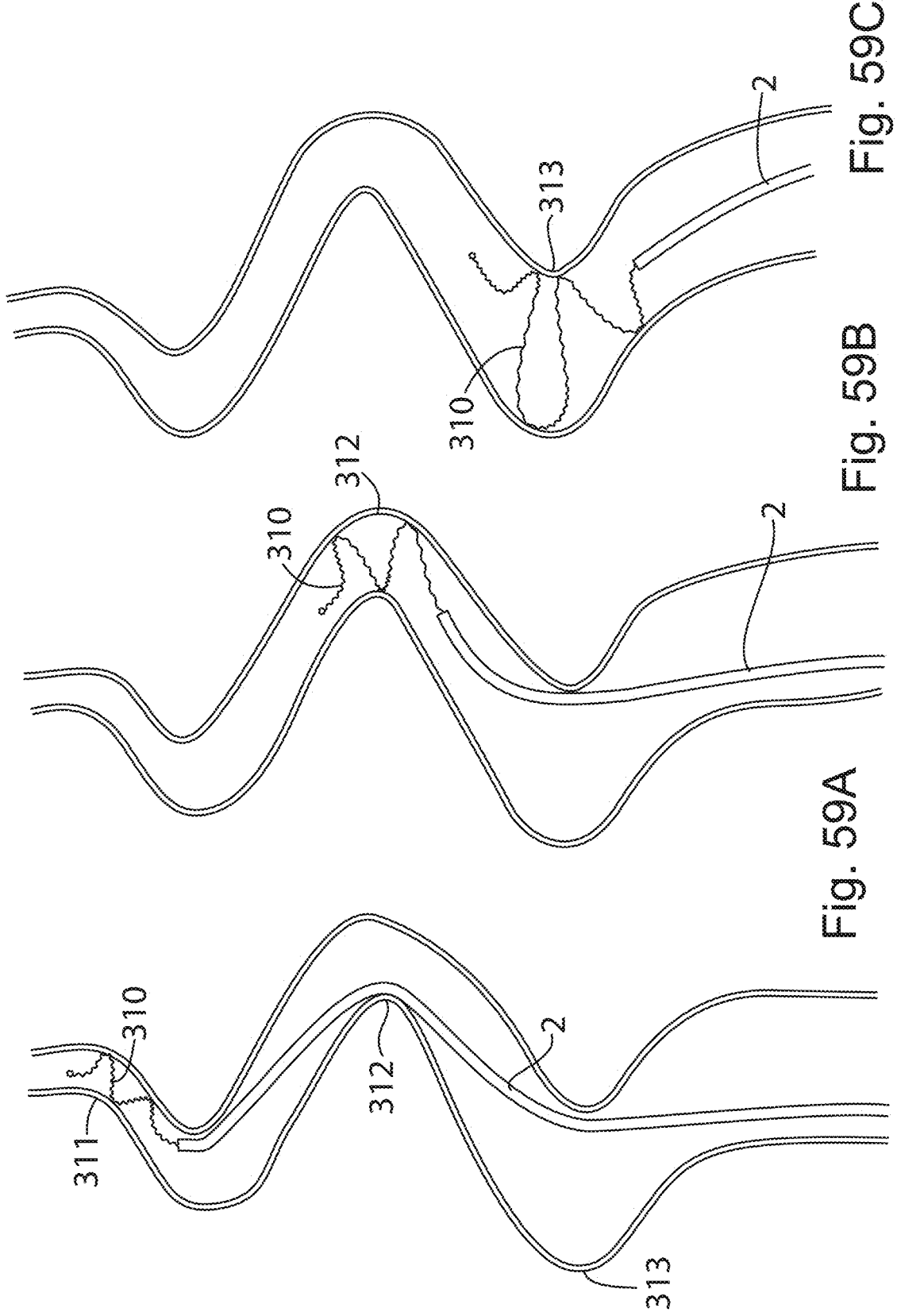

Guidewire and sheath

Advancement of sheath over wire
Removal of guidewire

Withdrawal of sheath to expose coil

Withdrawal of coil to treat vein

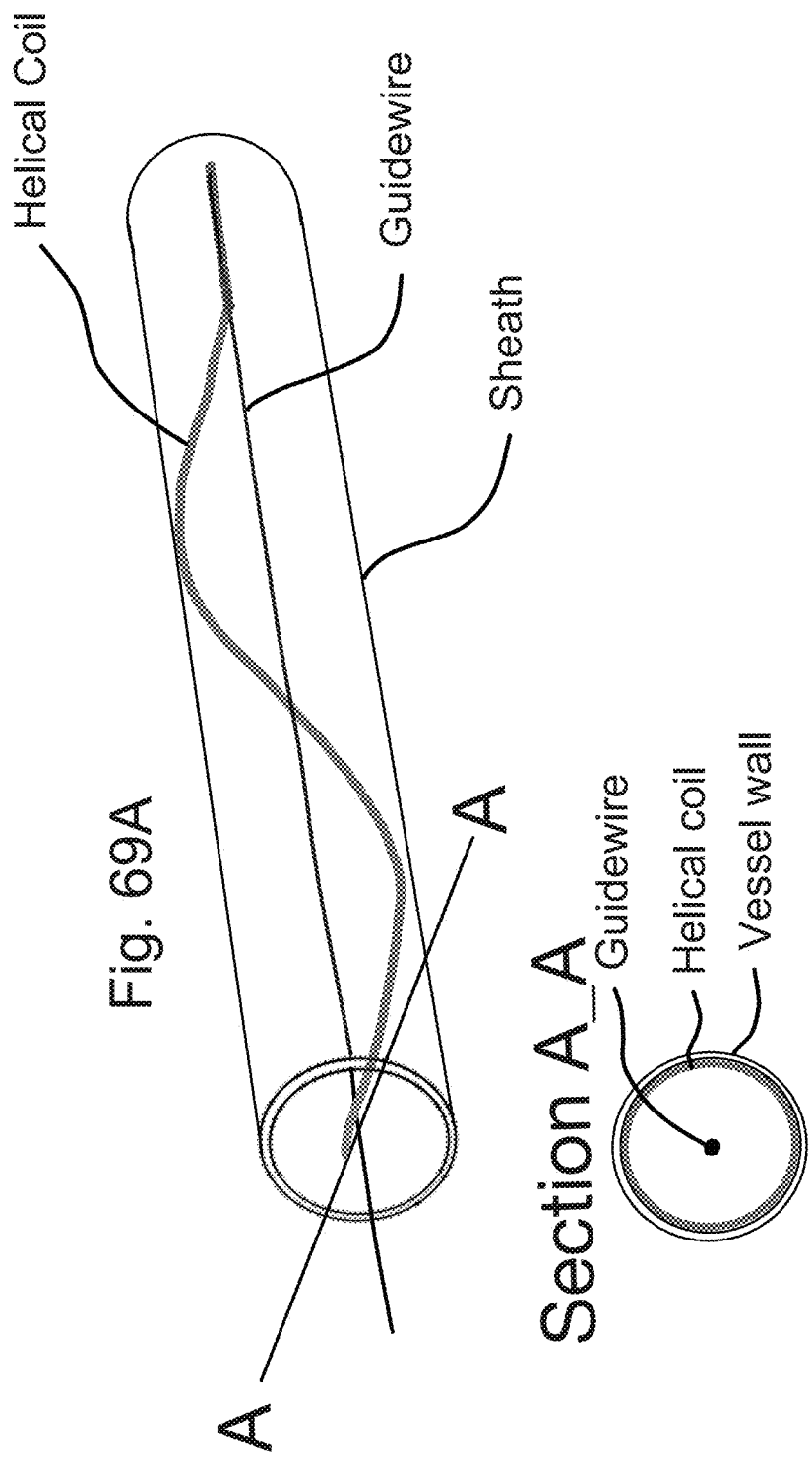

A: Peel-away sheath

B: Deployed Coil following sheath removal

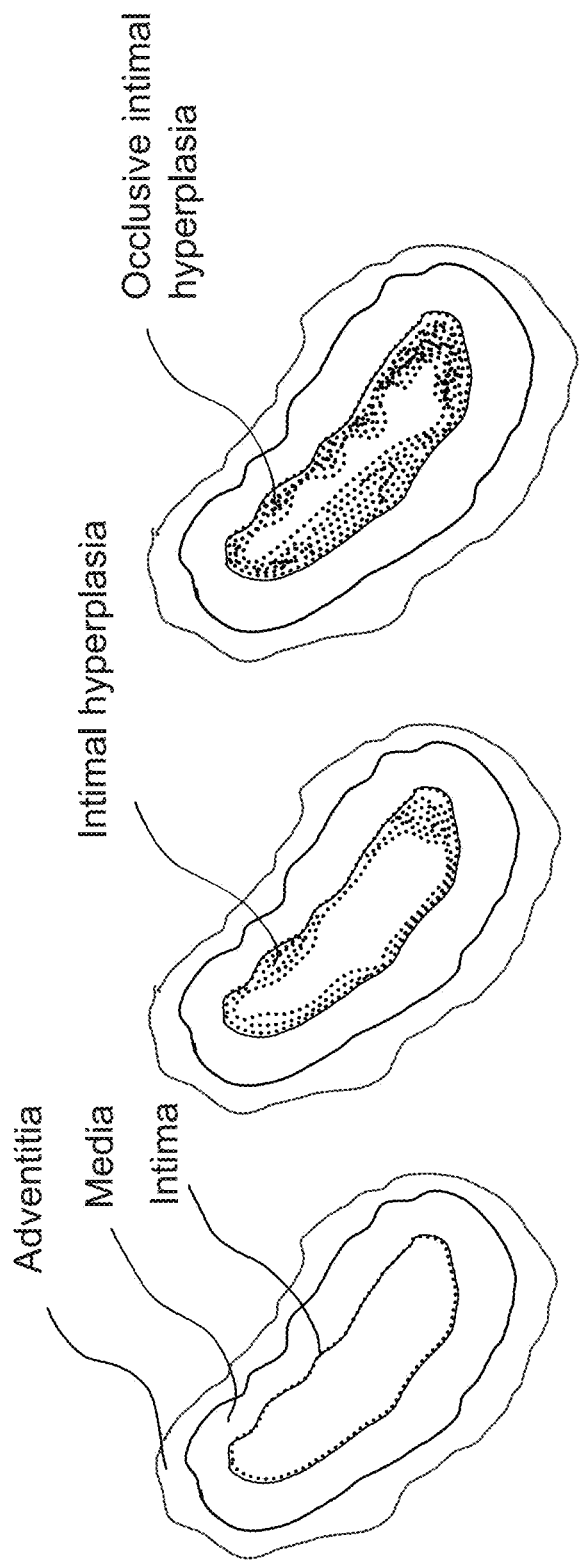
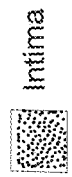
Fig. 72A    Fig. 72B    Fig. 72C
Intima

DEVICES AND METHODS FOR TREATING A VESSEL IN A SUBJECT

CROSS-REFERENCE TO RELATED APPLICATIONS

This application is a continuation of U.S. application Ser. No. 16/416,838 filed on May 20, 2019, which claims priority to European Application No. 18173170.4 filed on May 18, 2018, each of which is incorporated by reference herein in its entirety.

FIELD OF THE DISCLOSURE

The present disclosure relates to a method of treating a vessel in a subject, and a device for denuding a body lumen, in particular a superficial vein. Also contemplated are methods for denuding a body lumen, in particular a superficial vein, and methods of treating varicose veins.

BACKGROUND

Varicose veins are dilated, tortuous veins which are associated with structural vessel wall changes, incompetent venous valves, reflux and pooling of blood. They form part of the spectrum of chronic venous disease (CVD). Patients experience symptoms ranging from heaviness, aching pain and swelling to skin irritation, discolouration and ulceration in severe cases. The cause of varicose veins is unknown but genetic factors leading to weakness in vein wall components and valves are important in their development.

Varicose veins occur most commonly in the superficial venous network of the lower limb but can also occur in pelvic and oesophageal veins in certain disease states. Superficial veins drain blood from the skin and subcutaneous tissues into the deep venous network and ultimately back to the heart. The primary superficial vein is the great saphenous vein (GSV) which runs from the ankle to the groin on the medial side of the lower limb. The small saphenous vein (SSV) runs from the ankle to the knee on the posterior surface of the calf. Both the GSV and SSV drain into the deep femoral vein at junctional sites in the groin and posterior to the knee respectively.

Veins contain valves to prevent backflow of blood by increasing the efficiency of muscle pumps in the leg. Valves have a bicuspid structure formed by folds of endothelium supported by connective tissue and smooth muscle. The GSV has between 10 and 20 valves, the SSV typically has between 6 and 12 valves. Incompetent valves lead to the reflux of blood in the opposite direction to normal flow which can be seen using doppler ultrasound.

Veins have thinner walls in contrast to the thicker more elastic walls of arteries. Veins are more compliant (flexible) allowing their lumen to range from a collapsed form in low pressure states to a distended form when increases in venous pressures occur. The saphenous vein wall thickness typically ranges from 200 to 700 micrometres ($\mu$m). Like arteries, the wall comprises of three primary layers: the tunica intima, media and externa. However, unlike arteries the thickness and composition of the layers are different resulting in more compliant, less muscular vessels. The intimal layer comprises of a single layer of squamous cells known as the endothelium and some thin elastic fibres, collagen and smooth muscle cells. Importantly, there is an acellular layer of macromolecules known as the glycocalyx which covers the endothelial layer and protects it from shear forces. The glycocalyx is typically an evenly distributed structure of thickness 0.5-3 $\mu$m, which exceeds that of the endothelial Cells (0.2 $\mu$m). The media layer is composed of collagen, elastic fibres and three layers of smooth muscle cells. The externa or adventitia is the thickest layer and contains dense collagen, sensory nerves and elastic fibres.

Blood clotting or thrombosis can occur in both the deep and superficial venous networks. Thrombus in superficial veins is usually self-contained due to low-flow throughput and rarely propagates to the deep venous network. It is not dangerous to the patient and does not require treatment unless there is associated inflammation known as thrombophlebitis. Thrombosis in the deep veins of the leg, known as deep vein thrombosis (DVT) is clinically relevant as it can cause venous outflow obstruction, raising venous pressure and leading to oedema in the leg. The thrombus can also travel (embolise) to the lung causing a potentially fatal condition known as pulmonary embolism (PE).

Varicose veins are the most common peripheral vascular disorder, present in up to 40% of the adult population [1]. Risk factors include age, family history, obesity, occupations that involve long durations of standing and a sedentary lifestyle.

Treatment options range from conservative compression hosiery to surgical procedures. In the USA approximately 600,000 to 700,000 procedures take place per year to treat varicose veins. There the treatment of varicose veins has transitioned from open surgery (involving stripping out of the entire GSV) to less invasive thermal endovenous catheter-based techniques (involving radiofrequency or laser energy). Some countries including Germany and the United Kingdom, still perform a large portion of open vein stripping procedures.

In general, catheter directed minimally invasive thermal based treatments are used to treat superficial venous reflux today. A significant limitation of using thermal energy is the need for multiple preparation injections of high volumes of local anaesthetic mixed with saline (tumescence) to insulate the vein and protect surrounding tissues from thermal injury. This is both time-consuming for the physician and painful for the patient due to the requirement of multiple needle stick injections to the leg. As space is required between the skin and the vein for injection of tumescence, it also limits treatment when veins are located close to important nerves (as is the case with treatment of veins below the knee), near the skin or close to ulcers in patients with advanced CVD (CEAP Classification 5 & 6).

Thermal injury to surrounding nerves and skin can still occur despite the use of tumescent anaesthesia. The rate of nerve injury leading to persistent paresthesia is reported between 0% and 9% across a range of studies with higher rates for below knee GSV or SSV ablations.

Thromboembolic events are the most serious complication of superficial venous reflux treatment. The rate of DVT and PE in real world studies has been reported as 3% to 4% and 0.2 to 0.3% [2] respectively. All currently used techniques for treatment have inherent limitations which can increase the risk of developing a DVT and/or PE. It is important that any new treatment for varicose veins aims to reduce the risk of thromboembolic complications further.

An inherent problem with current thermal treatments is the risk of endothermal heat induced thrombosis (EHIT) which can lead to DVT and PE. This is thought to result from forward conduction of thermal energy from the tip of the thermal ablation device into the deep venous system. Newer laser tip fibres emit energy radially to reduce the risk of forward conduction. However, these technologies will not prevent steam bubbles spreading to adjacent non target locations which is still considered a possible mechanism of action of thermal ablation in addition to light absorption by tissues [3].

Newer non-thermal non-tumescent (NTNT) techniques for treatment of CVD have emerged in the last 10 years. Less painful NTNT techniques are more suitable for the clinical office setting where approximately 90% of procedures now take place in the US. Current NTNT techniques include chemical foam sclerotherapy, mechano-chemical ablation (MOCA) and cyanoacrylate glue (CAG) embolisation.

Chemical sclerotherapy (injection of a chemical detergent which disrupts endothelial cell membranes leading to vein occlusion by sclerosis) has been used for many years but its efficacy is greatly reduced in large veins due to the dilution effect and deactivation of sclerosant by blood constituents. Foaming of the sclerosant with gases to form a micro-bubble emulsion is a newer technique which displaces blood and allows the chemical to remain in contact with the endothelium for longer. Despite this enhancement, efficacy remains significantly lower than thermal techniques most likely due to incomplete endothelial coverage by the chemical sclerosant as seen in previous histological studies [4]. There is also a potentially increased risk of DVT as foam can propagate into the deep system, damaging the endothelium and forming a DVT. Higher concentrations of sclerosant foam mixtures can be more effective but also have a higher risk of DVT and systemic complications. Systemic complications of chemical sclerosant include transient ischaemic attacks (TIAs) and even stroke due to sclerosant compounds travelling into the arterial circulation via a small hole in the septum of the heart (patent foramen ovale). The teratogenicity of chemical sclerosants is also unknown, contraindicating their use in pregnant women.

MOCA involves a combination of chemical sclerosant and a mechanical action from within the vein lumen to both improve distribution of sclerosant and irritate the vein to encourage venospasm which reduces the vein diameter. Histological studies show a limited mechanical effect on endothelial cell integrity [5]. Medium term follow up studies have shown clinical efficacy but at levels inferior to current thermal techniques. The distal end of current MOCA devices, which causes a mechanical effect, can be prone to snagging or catching in the vein wall or valves. This results in patient discomfort, bruising, and even inadvertent vein stripping as previously reported [6].

Glue embolization involves injection of cyanoacrylate or equivalent compound resulting in an inflammatory response which causes vein occlusion. Limitations include the permanent implantation of a foreign material in the vein lumen, subsequent risk of allergic reactions, and risk of emboli travelling into the deep venous system causing DVT and/or PE.

Venous leg ulcers represent a major healthcare cost burden of $14 Billion annually in the United States [7] and are currently primarily managed using compression bandages. New data arising from the EVRA study [8] announced in April 2018 provides Level I evidence to support early endovenous treatment of varicose veins to increase the speed of ulcer healing in patients with CEAP class VI disease (C6). Thermal methods are less appropriate for venous ulcer patients. The need for multiple injections of tumescent anaesthesia both lengthens the procedure for a more elderly patient population and increases the risk of infection and haematoma formation due to the poor skin integrity adjacent to the ulcer. There is also an increased risk of nerve injury resulting in paresthesia when treating veins below the knee which is often the aim of treatment to prevent venous reflux near the ulcer bed [9].

Devices for treating blood vessels, including varicose veins, are described in the following documents: WO2017194698, US2016030719, US2016030068, US2016030023, WO2016102930, US2011046543, US2016242790, JP2016034485, WO2004112569, US2017056048, GB2519057 and U.S. Pat. No. 5,011,489.

U.S. Pat. No. 6,402,745 discloses a spring electrode having a helical configuration that functions to electrically disrupt an inner lumen of a vessel. The electrode is contained within a catheter, and a distal end of the electrode trails from the end of the catheter to contact the inner lumen of the vessel in a helical manner. This device would only partially denude an inner lumen of a blood vessel due to the contact area between the electrode and the inner lumen of the vessel.

WO2014140325 describes an implantable embolization bristle device that can denude a blood vessel in the treatment of various indications including varicose veins and haemorrhoids. The device comprises a core wire having a multiplicity of bristles extending radially outwardly from the core wire, in which the bristles are configured to engage the lumen of the blood vessel to denude the vessel by brushing against the vessel lumen. Bulky implantable devices are likely to cause patient discomfort in superficial veins, especially in the groin and knee areas. The use of bristles to denude a vein results in incomplete denudation of the inner lumen of the vein. Multiple pointed and/or elongated components significantly increase the risk of snagging and perforation in thin compliant vein walls.

It is an object of the present disclosure to overcome at least one of the above-referenced problems.

SUMMARY

The present disclosure addresses the need for a device for treating superficial venous reflux, that avoids the problems associated with the thermal, chemical and glue implant treatment techniques of the prior art while providing comparable best in class efficacy to thermal options. These objectives are met by providing a vein denuding device comprising a coil configured for transluminal delivery to a vein to be treated during the procedure (non-implant) and deployment whereby the coil circumferentially (ideally fully circumferentially) engages an inner lumen of the vein. The coil is an oversized coil (i.e. when deployed it has a diameter greater than the vein being treated) and has a roughened lumen-engaging surface, so that when it is deployed the roughened surface bears against the inner lumen of the vein, and axial movement of the coil along the vein in the deployed configuration causes the abrasive surface to shear the inner lumen of the vein. This results in the vein being mechanically denuded along a length of the vein, typically with consequent disruption of the endothelial and media layers of the vein, and ideally ultimately resulting in vein occlusion due to the formation of a thrombus which undergoes fibrotic transformation in the absence of an endothelial lining in a blood vessel. Ideally, the endothelium is completely circumferentially disrupted as if small areas are left intact, thrombus may not form and blood will continue to flow leading to treatment failure, recanalisation and/or early recurrence. Thus, a disclosed device may comprise a helical coil that is oversized relative to the diameter of the vein being treated to ensure circumferential engagement between the roughened surface of the helical coil and lumen of the vein. In addition, the coil (due to its resiliently deformable configuration) can self-adjust to allow continuous circumferential engagement while maintaining outward radial force along sections of vein or vessels with varying diameters and tortuous bends (FIGS. 59A-C).

According to a first aspect of the present disclosure, there is provided a device for denuding a body lumen comprising a body lumen denuding head operatively attached to an elongated catheter member and configured for transluminal delivery and deployment in the body lumen, the body lumen denuding head comprising a coil that is adjustable from an uncoiled delivery configuration suitable for transluminal delivery within the catheter member and a coiled deployed configuration having a diameter equal to or greater than the body lumen to be denuded and that circumferentially engages an inner lumen of the body lumen, whereby the coil has an abrasive surface configured to denude the body lumen when the helical coil is moved axially with or without rotation along the body lumen in the coiled configuration.

According to a second aspect of the present disclosure, there is provided a method of denuding a body lumen that employs a device comprising a body lumen denuding head operatively attached to an elongated catheter member and configured for transluminal delivery and deployment in a body lumen, the method comprising the steps of:

transluminally delivering the body lumen denuding head to a body lumen to be treated;

deploying the body lumen denuding head within the body lumen to be treated, in which the body lumen denuding head has an abrasive surface in circumferential contact with an inner lumen of the body lumen when deployed;

moving the body lumen denuding head along the section of the body lumen to be treated with the abrasive surface in circumferential contact with the body lumen, whereby the abrasive surface denudes the body lumen;

recapturing the denuding head into the catheter member; and removal of the device from the body lumen.

In one embodiment, the coil is a helical coil.

In one embodiment, the coil is "oversized" with respect to the diameter of the body lumen to be treated.

In one embodiment, the diameter of the coil (or the maximum diameter in the case of helical coils whose diameter varies along its length) is generally at least about 5% greater than the diameter of the body lumen to be treated (or in the case of body lumens with varying diameter, at least about 5% greater than the diameter of the body lumen at it widest point), for example at least 10%, 15%, 20%, 25% or 30% greater than the diameter of the body lumen to be treated, and typically from 5-30% greater. It is important that the coil is oversized along at least one turn of the coil, and typically oversized along 1-2 turns.

In one embodiment, the device is configured to denude an internal lumen of a vein.

In one embodiment, the coil comprises a shape memory material and is configured to adopt the coiled configuration when deployed.

The helical coil is generally sufficiently resiliently deformable to self-adjust to maintain a circumferential radial force against the wall of a body lumen of varying diameter as it travels along the body lumen. In one embodiment, the helical coil is configured to reflexively self-adjust its diameter in response to variable vein diameters and variable axial forces during axial movement along the treatment zone while maintaining an outward radial force on the vein.

The helical coil in its deployed state is oversized with respect to the widest part of the body lumen (or the section of the body lumen to be treated), thereby exerting a radial force around the full circumference of the body lumen along the length of the body lumen to be treated including its widest point.

The helical coil is typically sufficiently resiliently deformable to allow the coil pass around tortuous bends in the body lumen, while maintaining a radial force against the body lumen along the bend.

The helical coil is typically sufficiently resiliently deformable to allow the coil pass through a narrowing or obstruction in a body lumen, for example a valve in a vein.

In one embodiment, the device comprises an elongated control arm for the body lumen denuding head disposed within the catheter member.

Typically, the control arm is connected to a proximal end of the coil.

The control arm may be a hypotube, for example a hypotube formed from stainless steel, polymer or another material.

In one embodiment, the coil has a single coil element.

In one embodiment, the single coil element has 1-5, 1-4 turns, 1-3 turns, and preferably 1-2 turns, and ideally about 1.5 to 1.7 turns, in a deployed configuration.

In one embodiment, the diameter of the helical coil varies along its length.

In one embodiment, the diameter of the helical coil increases towards one end (i.e. conical).

The increase in diameter may be proximal to distal, or distal to proximal.

As used herein, the term "proximal" as applied to a helical coil refers to an end of the device that is closest to the introduction point—the term "distal" should be construed accordingly.

In one embodiment, the diameter of the helical coil increases towards a mid-point along the coil, and then decreases.

In one embodiment, the distal end of the coil terminates at a point disposed along, or adjacent to, a longitudinal axis of the helical coil.

In one embodiment, the helical coil has a proximal section of a first diameter, an intermediate section of reduced diameter relative to the proximal section, and a distal section of increased diameter relative to the intermediate section.

In one embodiment, the helical coil has a proximal and distal helical coil section, and an intermediate connecting (transition) section that is typically not helical and may be straight or curved.

In one embodiment, one of the proximal or distal helical coil sections is a right-handed helix, and the other of the proximal or distal helical coil sections is a left-handed helix.

In one embodiment, the proximal helical coil section is a right-handed helix and distal helical coil section is a left-handed helix.

In one embodiment, the distal helical coil section is a right-handed helix and proximal helical coil section is a left-handed helix.

In one embodiment, the coil comprises a plurality of coil elements, for example 2, 3, 4, 5 or more. Typically, each coil element is helical.

The helical coils may be arranged in a double, triple or quadruple coil arrangement.

Typically, the coil elements are co-axial.

Typically, each coil element has the same diameter when deployed.

Typically, each coil element has the same pitch when deployed. When in a deployed configuration, the plurality of coil elements together provide circumferential engagement of the inner lumen of the body lumen. Thus, each coil element may be configured such that, in a deployed configuration, it engages only a part of the circumference of the inner lumen, for example 90°-270°, 90°-180°, 180°-270° of engagement with the circumference of the body lumen.

The coil elements may be connected to the same control arm.

In one embodiment, the coil has two helical coil elements, for example a double helix.

Typically, each of the two helical coil elements has at least 0.5 turns when deployed, and typically from 0.5 to 1.0 turns or 0.5 to 0.7 turns.

In one embodiment, the coil has three helical coil elements, for example a triple helix.

Typically, each of the three helical coil elements has at least 0.3 turns when deployed, and typically from 0.3 to 1.0 turns or about 0.3 to 0.5 turns, when deployed.

In one embodiment, the coil has four helical coil elements.

Typically, each of the four helical coil elements has at least 0.25 turns when deployed, and typically from 0.25 to 0.75 turns when deployed.

In one embodiment, the plurality of coil elements are connected together at their distal ends.

In one embodiment, the plurality of coil elements are unconnected at their distal ends.

In one embodiment, the coil or each coil element is helical and is configured to have a pitch of about 0.5 to 1.5 times the coil diameter in the coiled configuration when deployed.

In one embodiment, the coil or each coil element is helical and is configured to have a pitch approximately equal to the diameter in the coiled configuration when deployed.

In one embodiment, one of the helical coil elements is axially spaced from another coil element. Generally, in this embodiment, the control arm (generally a distal end of the control arm) is bifurcated to provide distal control arms, each connected to one of the helical coils. However, the device may comprise separate control arms, for independent control of the two helical coils.

In an embodiment of the vein denuding head having axially spaced apart helical coils, the control arm of the distal helical coil typically passes axially through the proximal helical coil (through one, more or all of the coils making up the proximal helical coil).

In one embodiment, the proximal helical coil has a maximum diameter that is greater than the maximum diameter of the distal helical coil (for example, 1.5-4 times greater).

In another embodiment, the proximal helical coil has a maximum diameter that is less than the maximum diameter of the distal helical coil (for example 1.5 to 4 times less).

In one embodiment, the pitch of the proximal and distal coil elements is different.

In one embodiment, the narrower coil has a greater pitch.

In one embodiment, the distal and/or proximal helical coil is conical.

In one embodiment, the distal and proximal helical coils are conical.

Typically, the diameter of the helical coil increases in the proximal direction (i.e. towards the entry point of the device).

In one embodiment, the coil or each coil is configured to have a diameter in the coiled configuration when deployed that is at least equal to or greater than the diameter of the vein to be treated.

In one embodiment, the or each helical coil is conical (i.e. the diameter of the coil increases or decreases as it approaches the device entry point—i.e. proximally).

Typically, the diameter of the helical coil increases in the proximal direction.

In one embodiment, the coil has a profile selected from circular, oval, curved, convex, concave, T-shaped, inverted T-shaped, or any other shape.

In one embodiment, the coil has a flat internal surface, and an external surface that is curved, concave, convex, or inverted T-shaped. Helical coils having these profiles are illustrated in FIGS. 34A to 41B.

In one embodiment, the roughened surface of the coil or each coil element is formed by treating the surface of the coil, typically an external body lumen facing surface of the coil (and/or a lateral surface of the coil), to introduce surface roughness.

In one embodiment, an internal surface of the coil is not roughened, and ideally smooth. This facilitates retraction of the coil into the catheter member where the smooth surface of the coil comes into contact with the mouth of the catheter.

In one embodiment, surface roughness is produced by mechanical, electrical, chemical abrasion, or abrasion by other means.

In one embodiment, the external surface of the coil comprises indentations configured to provide the roughened surface.

In one embodiment, the indentations are configured to provide teeth on the surface. In one embodiment, the indentations are transverse indentations.

In one embodiment, the transverse indentations extend fully across the external surface of the coil.

In one embodiment, the transverse indentations are disposed on each side of the external surface (i.e. when the external surface of the coil is concave).

In one embodiment, the indentations are longitudinal, and extend fully or at least partially along the length of the helical coil. The longitudinal indentations may be straight, curved, wavy, zig-zagged, diamond shaped or any configuration.

In one embodiment, the helical coil has an inverted T-shape profile, in which the teeth from the leg of the inverted T shape.

In one embodiment, the teeth have a profile selected from triangular, polygonal, rhomboid or any other profile configured to scrape away an endothelial layer of a body lumen.

In one embodiment, the coil comprises lateral teeth.

In one embodiment, the coil has a flat internal and external surface, and lateral teeth.

In one embodiment, the coil is formed from a flat wire with a diamond textured and roughened outer surface and a smooth inner surface.

In one embodiment, the coil has grooves or pores to act as reservoirs for therapeutic agents.

In one embodiment, the coil or each coil element comprises a core wire and the abrasive surface is formed by a second wire wound helically around the core wire to form a second coil.

In one embodiment, the second wire has a polygonal cross-section.

In one embodiment, the second coil has a pitch of 1 to 5 mm.

In one embodiment, a pitch of the second coil is greater at a proximal end thereof.

In one embodiment, a pitch of the second coil is lesser at a proximal end thereof.

In one embodiment, the second coil is bonded to the core wire, typically at a plurality of locations.

In one embodiment, a surface of the second wire is treated to introduce surface roughness.

In one embodiment, the helical coil has a proximal section that is generally co-axial with a longitudinal axis of the helical coil.

In one embodiment, the helical coil has a distal section that is generally co-axial with a longitudinal axis of the helical coil.

In one embodiment, the control arm for the body lumen denuding head is disposed within the catheter member. Typically, the control arm is connected to a proximal end of the coil. The control arm may be a hypotube, for example a hypotube formed from stainless steel, polymer or another material.

In one embodiment, the control arm is configured for axial movement to deploy the body lumen denuding head at a target location in a body, and withdraw the body lumen denuding head into the catheter member after treatment.

In one embodiment, the control arm is configured for rotational movement to rotate the body lumen denuding head in the body lumen.

In one embodiment, the device comprises a distal control arm connected to a distal end of the coil and a proximal control arm connected to a proximal end of the coil, whereby relative axial movement of the distal and proximal arms effects coiling and uncoiling of the coil.

In one embodiment, a distal end of the coil comprises an atraumatic head, for example a flexible material or a spherical ball.

In one embodiment, the device comprises a handle operatively connected to a proximal end of the catheter member and configured to control the deployment and retraction of the coil. In one embodiment, the handle comprises a control element configured for axial adjustment of the control arm or arms with or without rotation. In one embodiment, the handle comprises a control element configured for rotational adjustment of the control arm or arms.

In one embodiment, the device is configured for adjustment between:
 a delivery configuration in which the helical coil is stowed within the catheter member in an uncoiled configuration,
 a first body lumen denuding configuration in which in use the coil is deployed in the body lumen to be treated at a first axial position and bears against a circumference of the body lumen;
 a second body denuding configuration in which in use the coil is deployed in the body lumen to be treated proximal to the first axial position and bears against a circumference of the body lumen; and
 a withdrawal configuration in which the coil is stowed within the catheter member.

The method of the disclosure may be employed to venous disease, especially superficial venous reflux, and preferably varicose veins. The veins treated are generally saphenous veins, and typically the Great Saphenous Vein (GSV) or Small Saphenous Vein SSV). In one embodiment of the method of the disclosure, the body lumen denuding head is moved proximally towards the access site along the section of the body lumen to be treated.

In one embodiment, the method comprises treating a section of the body lumen having a length of at least 2, 4, 6, 8, 10, 12, 14, 16, 18 or 20 cm.

In one embodiment, the method is for completely occluding a body lumen, for example a vein or an artery.

In one embodiment, the method is for partially occluding a body lumen, for example a vein or an artery. Thus, the device and method may be employed to treat conditions or indications characterised by dysregulated or unwanted blood volume or flow rate through a section of the vasculature, by employing the device to partially occlude the section of the vasculature.

In another case, the method is to thicken the wall of a vein by inducing significant wall thickening such as circumferential intimal hyperplasia. This effect "arterialises" a vein making it more resilient to the effect of higher blood pressure and shear forces. This thickening effect should be self-limiting when it occurs in response to a once off mechanical stimulus as opposed to the uncontrolled intimal hyperplasia that occurs when veins are exposed to persistently higher shear forces when used as conduits in the arterial system. Thus, the device and method may be employed to prepare a vein prior to grafting into the arterial circulatory system.

The body lumen may be vasculature, for example an artery or vein.

In one embodiment, the method is a method of treating a varicose vein by denuding a section of the superior rectal artery.

In one embodiment, the method is a method of treating haemorrhoids by denuding a section of the vein.

In one embodiment, the method is a method of thrombectomy by denuding a section of a vein or artery occluded by thrombus.

In one embodiment, the method is as a preparation step to prime a target area of a body lumen (i.e. section of vasculature) prior to the implantation of a medical device such as a valve or stent.

In one embodiment, the method is as a preparation step to prime a target area of an artery prior to grafting to reduce risk of Type 1 endoleaks.

In one embodiment, the body lumen being denuded is an artery feeding a tumour such as a solid tumour.

In one embodiment, the body lumen is a portal vein providing nutrients from the intestine to the liver. In one embodiment, the subject being treated has a liver disease such as cancer and the method is typically performed prior to liver resection.

In one embodiment, the body lumen being treated is a blood vessel forming part of an arteriovenous malformation.

In one embodiment, the body lumen being treated is a spermatic vein. Thus, methods of treating varicocele are also described.

In one embodiment, the body lumen being treated is a blood vessel (i.e. uterine artery) supplying a uterine fibroid.

In one embodiment, the body lumen being treated is part of the gastro-intesinal tract such as the duodenum, jejunum, or ileum.

In one embodiment, the body lumen being treated is the prostatic artery.

In one embodiment, the body lumen being treated is a pelvic vein.

In one embodiment, the method is employed to treat Patent Foramen Ovale (PFO), by denuding a contacting surface of the arterial septal flaps involved in PFO.

In one embodiment, the method is employed to treat Patent Ductus Arteriosus, by disrupting mucosal layers of the ileocaecal valve and ileum.

In one embodiment, the method is employed to treat Small Intestinal; Bacterial Overgrowth, by denuding the ductus arteriosus.

In one embodiment, the method is employed to treat Barrett's Oesophagus, by mechanically ablating or denuding cells (abnormal cells) in the lower oesophagus.

In one embodiment of the method, the method includes a step of delivering a liquid sclerosant into the body lumen distal of the catheter member.

In one embodiment of the method, the method includes a step of delivering thermal energy to the body lumen by conduction through the lumen engaging surface of the device.

In one embodiment of the method, the method includes a step of using an intravenous ultrasound (IVUS) probe attached or incorporated in denuding head element to determine the vessel response to treatment.

In one embodiment of the method, therapeutic agents coat the outer surface or are embedded in grooves or pores on the device and delivered to the inner surface of a body lumen.

In one embodiment of the method, the method employs a body lumen denuding device.

In another aspect, the present disclosure provides a method of treating a vessel (or any body lumen) in a subject, comprising the steps of:

advancing a device distally across a treatment zone in the vessel, wherein the device comprises an elongated catheter having a lumen and a distal end, and a radially expansive treatment element disposed in the lumen and configured for axial movement relative to the catheter;

deploying the radially expansive treatment element proud of the distal end of the catheter to radially expand and circumferentially impress against the lumen at a distal end of the treatment zone;

withdrawing the deployed radially expansive treatment element proximally along the treatment zone with the treatment element circumferentially impressed against the vessel lumen to mechanically and circumferentially denude the treatment zone of the vessel;

recapturing the radially expansive treatment element into the lumen of the catheter; and withdrawing the device from the treated vessel.

In one embodiment, the vessel is a varicose vein, and in which the method is typically a method of treating the varicose vein by denuding a lumen of the vein to cause occlusion of the varicose vein.

In one embodiment, the step of mechanically and circumferentially denuding the treatment zone of the vessel comprises affecting circumferential exposure of the subendothelial vessel surface along the treatment zone.

In one embodiment, the radially expansible treatment element is self-adjustable from an undeployed delivery configuration suitable for transluminal delivery within the catheter and a deployed radially expanded configuration having a diameter greater than the vessel in the treatment zone.

In one embodiment, the radially expansible treatment element is resiliently deformable, wherein the radially expansible treatment element reflexively self-adjusts its diameter in response to variable vessel diameters and variable axial forces during axial movement along the treatment zone while maintaining an outward radial force on the vessel.

In one embodiment, an external vessel-lumen facing surface of the radially expansible treatment element has a roughened surface.

In one embodiment, an external vessel-lumen facing surface of the radially expansible treatment element has a roughened surface, in which the roughened surface comprises a macro and micro abrasive surface.

In one embodiment, the vessel is a superficial vein such as the great saphenous vein, the small saphenous vein, a perforator vein or tributary vein.

In one embodiment, the superficial vessel is a vein selected from the great saphenous vein and the short saphenous vein.

In one embodiment, the method is a method of treatment of superficial venous reflux in a subject, and in which the vessel is a superficial vein.

In one embodiment, the method is a method of treatment of a varicose vein in the subject, wherein the vein being treated is varicose.

In one embodiment, the method results in occlusion of the treated vessel.

In one embodiment, the method is a method of narrowing but not occluding a vessel.

In one embodiment, the step of withdrawing the deployed radially expansive treatment element proximally along the treatment zone causes mechanical stretch or the vessel wall resulting in activation of smooth muscle within the wall leading to vasospasm along the treatment zone and optionally prevention of nitric oxide secretion from endothelial cells and subsequent prolongation of vasospasm.

In one embodiment, the radially expansible treatment element is a coil.

In one embodiment, the radially expansible treatment element is a helical coil.

In one embodiment, the method is performed using an imaging modality such as ultrasound guidance.

In one embodiment, the method includes the step of recapturing the treatment element into the catheter member comprises returning the treatment element to an undeployed state, allowing repositioning and repeat deployment.

In one embodiment, the method includes a step of deploying a temporary lumen occluding element during at least one of the steps to halt blood flow in high flow vessels.

In another aspect, the present disclosure provides a method of treating superficial venous reflux in a superficial vein in a subject comprising a step of mechanically and circumferentially denuding a treatment zone of the superficial vein.

In one embodiment, the treatment zone of the superficial vein that is circumferentially denuded has a length of 5 to 25 cm.

In one embodiment, the step of mechanically and circumferentially denuding the treatment zone of the superficial vein comprises effecting circumferential exposure of the subendothelial vessel surface along the treatment zone.

In one embodiment, the step of mechanically and circumferentially denuding the treatment zone of the vein comprises deploying a vein denuding device in a distal part of the target section of the superficial vein to circumferentially impress against the vein lumen, and withdrawing the deployed vein denuding device proximally along the treatment zone with the device circumferentially impressed against the vein lumen.

In one embodiment, the step of mechanically and circumferentially denuding the treatment zone of the vessel comprises effecting circumferential exposure of the subendothelial vessel surface along the treatment zone.

In one embodiment, the vein denuding device is self-adjustable from an undeployed delivery configuration suitable for transluminal delivery within the catheter and a deployed radially expanded configuration having a diameter greater than the vessel in the treatment zone.

In one embodiment, the vein denuding device is resiliently deformable, wherein the radially expansible treatment element reflexively self-adjusts its diameter in response to variable vessel diameters and variable axial forces during axial movement along the treatment zone while maintaining an outward radial force on the vessel.

In one embodiment, an external vessel-lumen facing surface of the vein denuding device has a roughened surface.

In one embodiment, an external vessel-lumen facing surface of the vein denuding device has a roughened surface, in which the roughened surface comprises a macro and micro abrasive surface.

In one embodiment, the radially expansible treatment element is a coil and preferably a resiliently deformable coil.

In one embodiment, the radially expansible treatment element is a resiliently deformable helical coil.

In one embodiment, the method is performed under ultrasound guidance.

In one embodiment, the axial movement of the radially expansive treatment element (or helical coil) is automatic or semi-automatically controlled independent of the operator.

In one embodiment, the device is configured to collect data for operator feedback, or for further interpretation by human, statistical, big-data or machine learning analysis. This, the device may incorporate one or more sensors configured to detect in-vivo data, for example temperature, pressure, electrical impedance or the like, of tissue or blood. The device may be configured to relay the in-vivo data wirelessly or along wires disposed in the catheter member. The device may be configured to relay data to a remote processor.

Other aspects and preferred embodiments of the disclosure are defined and described in the other claims set out below.

BRIEF DESCRIPTION OF THE FIGURES

FIG. 33 is a side elevational view of the device of FIG. 31.

FIG. 37A and FIG. 37B are perspective and side elevational views of a section of a further helical coil according to the disclosure.

FIG. 38A and FIG. 38B are perspective and side elevational views of a section of a further helical coil according to the disclosure.

FIG. 52A illustrates small arteries feeding a tumor, and FIG. 52B is an exploded view of part of one of the arteries showing a device of the present disclosure in use to denude a section of the lumen of the artery and occluding the artery due to the formation of thrombus.

FIG. 53A illustrates portal vein vasculature, and FIG. 53B is an exploded view of part of one of the veins showing a device of the present disclosure in use to denude a section of the lumen of the artery and occluding the artery due to the formation of thrombus.

FIG. 54 illustrates a natural arteriovenous shunt section of vasculature incorporating a malformation, and a device according to the present disclosure in use denuding a section of the shunt to occlude the malformed shunt by formation of a thrombus.

FIG. 55 illustrates the left spermatic vein and varicoceles surrounding the left testicle, and a device according to the present disclosure in use denuding a section of the left spermatic vein to occlude the vein by formation of a thrombus.

FIGS. 59A to 59C illustrate how the helical coil forming part of a device of the present disclosure can self-adapt to varying vessel diameter and navigate a tortuous vessel: (A) the deployed helical coil in circumferential contact with the lumen of the vessel at a narrowed section of the vessel; (B) the helical coil navigating through a sharp turn in the vessel while maintaining circumferential contact with the lumen of the vessel; and (C) the helical coil navigating through a sharp turn in the vessel of greater diameter while maintaining circumferential contact with the lumen of the vessel.

FIGS. 69A and 69B illustrate the sheath used in FIGS. 68A-68D which holds an undeployed helical coil in its internal perimeter to accommodate passage of a guidewire.

FIGS. 72A to 72C illustrate vein remodelling in Arteriofistula formation (A) Normal vein; (B) Intimal hyperplasia with self limited thickening of the intimal layer. (C) Vein graft failure due to excessive intimal hyperplasia causing lumen obstruction.

DETAILED DESCRIPTION

Figure 1:
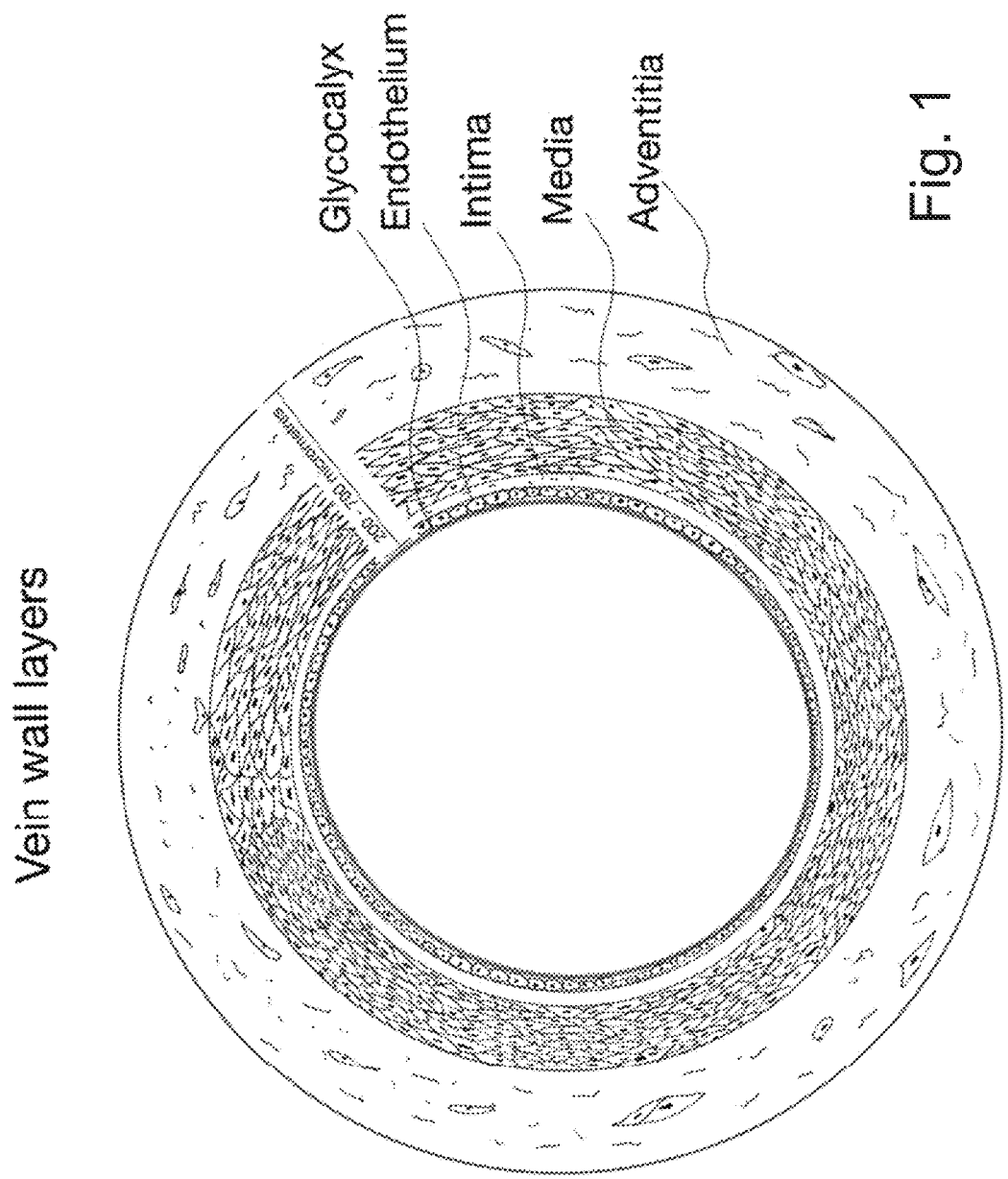
FIG. 1 is an illustration of the human vasculature in an axial plane showing the composition of a typical vein wall including the inner lining of the vein (tunica intima) with associated endothelium and glycocalyx coverings, adjacent intermediate layer (tunica media) and outer layer (tunica adventitia). The typical thickness in micrometres for an adult vein wall is also included.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, elements, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, goats, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

As used herein, the term "denuding" should be understood to mean mechanical removal or irreversible functional destruction of the superficial layer of an inner luminal surface of a body lumen along a section of the body lumen. When the body lumen is a vessel or vein, the superficial layer of the inner lumen is generally a single layer of squamous cells known as the vascular endothelium and its associated connective tissue extending to the superficial cell layers of the media but not deeper than the media layer. The endothelium is required for the survival of the body lumen as it provides a selective barrier and anti-thrombotic surface, the removal of which results in the exposure of pro-thrombotic factors which interact with normal blood constituents to cause clotting and occlusion of the body lumen and release natural vasoconstrictors into the lumen. When the body lumen is a vein, the term refers to removal of one or more layers of the tunica intima layer and superficial media layer. The device and methods of the present disclosure denude a longitudinal section of a body lumen, for example 1-60 cm, and denude the body lumen circumferentially; that is the full circumference (or partial or nearly the full circumference) if the body lumen is denuded along a section being treated.

As used herein, the term "body lumen" means a cavity in the body, and may be an elongated cavity such as a vessel (i.e. an artery, vein, lymph vessel, urethra, ureter, sinus, auditory canal, nasal cavity, bronchus, fallopian tube, spermatic duct) or an annular space in the heart such as the left atrial appendage, left ventricular outflow tract, the aortic valve, the mitral valve, mitral valve continuity, tricuspid valve, pulmonary valve, or heart valve, or venous valve, or valve opening. Preferably the body lumen is a vasculature (i.e. a vein or artery or an arterio-venous vessel). The vein may be selected from a saphenous vein (SSV, GSV, AASV), a pelvic vein, varicocele, or a portal vein. The artery may be selected from an aorta, superior rectal artery, a section of artery intended for stenting for full or partial embolisation, a uterine artery, or a ductus arteriosus. The body lumen may be a section of the gastrointestinal tract, for example the duodenum, small intestine. The body lumen may be the oesophagus.

As used herein, the term "elongated catheter member" should be understood to mean an elongated body having a distal end that is operably connected to the body lumen denuding body. In one embodiment, the catheter member comprises a control arm (for example a tubular member) operably connected to the denuding body for control thereof. The control arm may take any form, for example, a rod, wire, or tubular member such as a hypotube. In one embodiment, the control arm and denuding body are axially adjustable relative to the catheter member. The denuding body is generally uncoiled and stowed in a distal end of the catheter member during delivery and withdrawal. Axial adjustment of the control arm relative to the catheter body results in deployment of the denuding body in its coiled configuration.

"Transluminal delivery" means delivery of the body lumen denuding body to a target site (for example a varicose vein) through a body lumen, for example delivery through an artery, vein, or the gastrointestinal tract.

As used herein, the term "coil" should be understood to mean a loop-shaped element that is adjustable from an uncoiled configuration suitable for retraction into a catheter member and coiled configuration that in use is capable of circumferentially engaging and impressing its surface against a body lumen (i.e. engage the internal lumen of the vein along at least one full turn of the coil). The coil in its coiled configuration is generally circular, but may also be oval, square, triangular, or rectangular, as long as it is capable of circumferentially engaging an inner wall of the body lumen. As most veins and arteries have a circular, or almost circular, profile, a circular coil is preferred, as the radial force exerted by the coil in its deployed configuration is spread evenly around the wall of the body lumen. A coil having a diameter equal or greater than the diameter of the body lumen to be treated along at least one full turn of the coil is required to achieve circumferential engagement with the internal lumen of a vein, and thereby achieve circumferential denuding of the vein (see A in FIG. 13). In a preferred embodiment, the coil is a helical coil having at least one full circumferential turn, and preferably from 1 to 3 turns, for example about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, or 2.9 turns. The coils of the helical coil are preferably circular, but may also have another profile, for example oval, square, triangular, or rectangular. The helical coil may be conical. The diameter of the coil is typically 2-20 mm, more preferably 3-12 mm, in a relaxed state. The pitch of the helical coil is typically approximately the same as the diameter, but it may vary from 0.5 to 1.5 times the diameter, in a relaxed state. It will be appreciated that the dimensions of the coil may be varied depending on the body lumen, to ensure that the coil is "oversized" with respect to the diameter of the body lumen. In this regard, the diameter of the coil (or the maximum diameter in the case of helical coils whose diameter varies along its length) is generally at least about 5% greater than the diameter of the body lumen to be treated, for example at least 10%, 15%, 20%, 25% or 30% the diameter of the body lumen to be treated, and typically from 5-30% greater. It is important that the coil is oversized along at least one turn of the coil, and typically oversized along 1-2 turns. The coil may be formed from an elongated element, typically a single elongated element, for example a wire or filament. The coil may be formed from a metal (for example stainless steel) or metal alloy, or it may be formed from a shape-memory alloy such as NITINOL, or it may be formed from a natural, synthetic or semi-synthetic polymer such as chitosan, nylon or rayon. The body lumen denuding head ideally consists of a single coil element, although in certain embodiments the coil may comprise a plurality of coil elements, for example 2, 3, 4, 5, 6, 7, 8, 9 or 10, and preferably 2-4 coil elements.

The width of the coil element is at least 0.1 mm. The width is typically 1 to 3 mm to allow delivery via an appropriately sized catheter and introducer sheath.

Figure 60A:
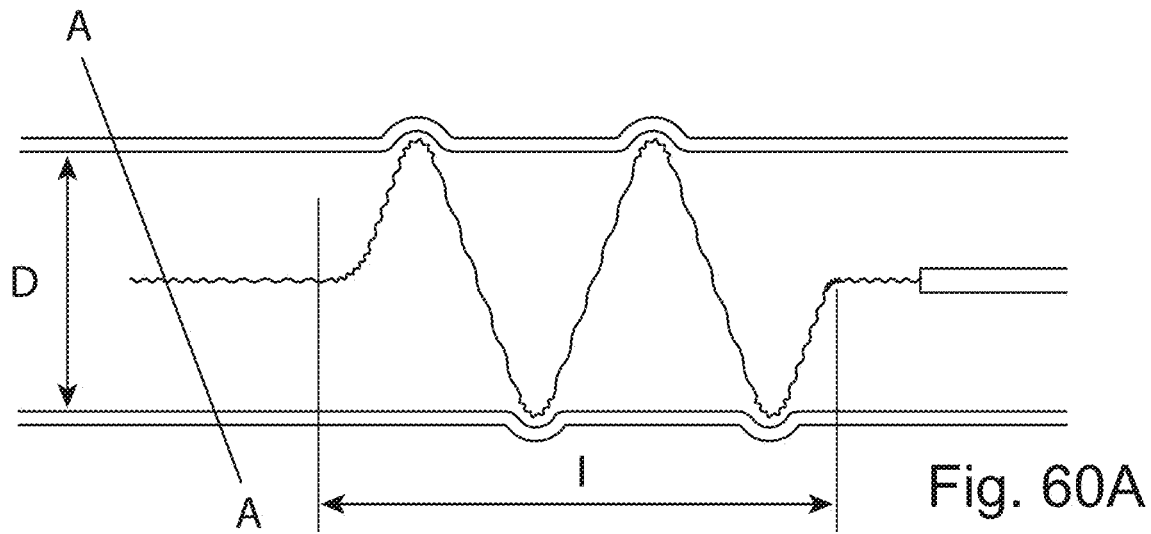
FIGS. 60A to 60C illustrate how the helical coil forming part of a device of the present disclosure can self-adjust the diameter of the coil to maintain circumferential engagement with the lumen of the vessel when the vessel actively constricts due to vasospasm or tapers to a smaller width: (A) the deployed helical coil in circumferential contact with a vessel section of length l and diameter D prior to vasospasm of the vessel; (B) Section A-A is an axial view of the helical wire in contact with the vessel wall under a hoop force HF generated by pressure from a constraint force P; (C) the deployed helical coil in circumferential contact over an extended length L within the constricted vessel of diameter d during vasospasm.
Figure 60B:
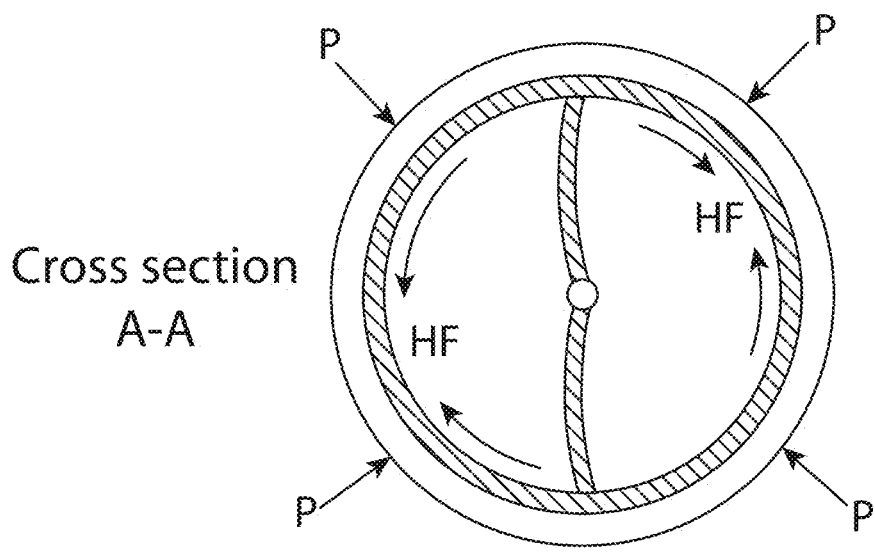
Figure 60C:
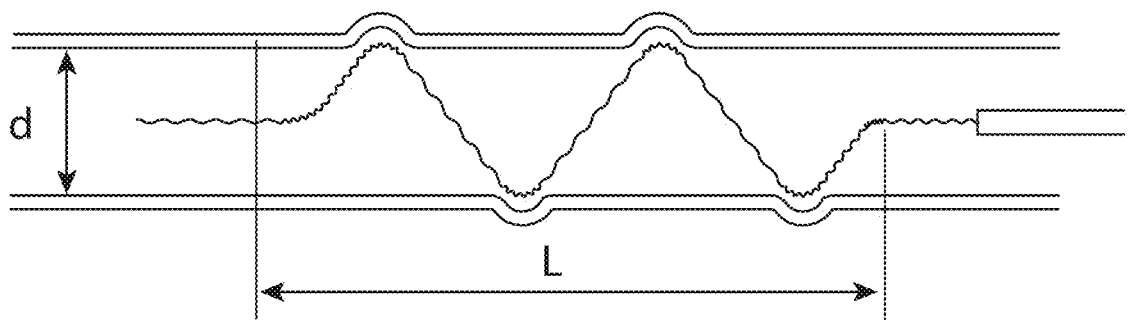

Typically, the helical coil is sufficiently resiliently deformable to maintain a circumferential radial force against the wall of the body lumen of varying diameter as it travels along the body lumen (i.e. it is configured to "self-adjust" or is "self-adjustable"). This is illustrated in FIGS. 59A-59C which illustrate the use of a device of the present disclosure to denude a vein with several bends and a diameter that progressively increases. In this embodiment, the helical coil in its deployed state will be oversized with respect to the widest part of the body lumen, thereby exerting a radial force around the full circumference of the body lumen at its widest point shown in FIG. 59C, and is sufficiently resiliently deformable for the coil diameter to adjust to varying diameter of the vein while maintaining a denuding radial force against the circumference of the body lumen. The helical coil is typically sufficiently resiliently deformable to allow the coil pass through constrictions or valves in veins, as illustrated in FIGS. 56A-C and 57A-C, respectively. These constrictions or changes in vein diameter over the treatment length may be either static (wider diameter of proximal vessel tapering to narrower distal vessel) or dynamic (contraction of vein wall smooth muscle leading to reduced vein diameter in a physiological process known as venospasm). The reducing vein diameter will increase the radial forces on the helical coil, this will in turn increase the hoop force generated within the material of the helical coil which will translate as a longitudinal force to increase the length of the coil. This concept is illustrated in FIGS. 60A-C where the device is shown deployed in a typical vessel over a length l and diameter D. The radial force is equivalent to the pressure P acting perpendicular to the vein wall. The pressure that the vessel exerts on the oversized coil or hoop force (HF) is acting to compress the coil and increases when the diameter of the vessel is reduced to d. Due to the open helical coil design this increased hoop force will translate longitudinally to lengthen the coil to a length L. This will allow a reduction of the radial forces at the contact point of the device outer surface with the vein wall to prevent excessive friction but maintain sufficient force to keep the surface engaged and impressed against the vein. Excessive friction can lead to undesirable catching or snagging of coil segments and wall perforation and/or trauma to connective tissue adjacent to the vein.

As used herein, the term "coil element" refers to individual and separate coil elements that together make up the coil part of a device of the present disclosure. Typically, each coil element is helical. Typically, the coil elements are co-axial. Typically, each coil element has the same diameter when deployed. Typically, each coil element has the same pitch when deployed. When in a deployed configuration, the plurality of coil elements together provide circumferential engagement of the inner lumen of the body lumen. Thus, each coil element may be configured such that, in a deployed configuration, it engages only a part of the circumference of the inner lumen, for example 90°-270°, 90°-180°, 140°-220°, or 180°-270°, of engagement with the circumference of the body lumen. In one embodiment, the coil has two helical coil elements, for example a double helix. Typically, each of the two helical coil elements has at least 0.5 turns when deployed, and typically from 0.5 to 1.0 turns or 0.5 to 0.7 turns. In one embodiment, the coil has three helical coil elements, for example a triple helix. Typically, each of the three helical coil elements has at least 0.3 turns when deployed, and typically from 0.3 to 1.0 turns or about 0.3 to 0.5 turns, when deployed. In one embodiment, the coil has four helical coil elements. Typically, each of the four helical coil elements has at least 0.25 turns when deployed, and typically from 0.25 to 0.75 turns when deployed. In one embodiment, the plurality of coil elements are connected together at their distal ends (closed configuration). In one embodiment, the plurality of coil elements are unconnected at their distal ends (open configuration).

As used herein, the term "non-detachably attached to the catheter member" as applied to the body lumen (or vessel or vein) denuding head should be understood to mean that the device is not configured to detachment and release of the head from the catheter member in the body; in other words, the device is not configured to implantation of the body lumen denuding head in the body.

Implantable devices are undesirable for use in the treatment of superficial venous disease for the following reasons; Superficial leg veins are located relatively close to the skin surface where they can be easily palpated to touch. Bulky implantable devices can potentially cause pain, irritation or local skin deformity; Implants may inhibit the ability of the vein to reduce its diameter by contraction of smooth muscle known as venospasm. This is important in reducing vein diameter, reducing the amount of thrombus within the vein and preventing recanalisation; Implants may cause immune mediated inflammatory reactions.

The body lumen engaging surface of at least part of the coil is abrasive for shearing or irreversibly damaging an inner lining of the body lumen away from the body lumen. The surface may be treated chemically, electrically or physically/mechanically to make it abrasive. There are several types of machining that can be adopted in order to roughen the surface including mechanical abrasion, shot blasting, sand blasting, knurling, electrical discharge machining, and pulse electrochemical machining. Chemical etching can also be used to roughen the surface of the part. The surface may be serrated. The surface could also include raised portions that when contacting the vessel lumen act as an abrasive surface, these raised portions could be pieces bonded to the surface of the abrasive surface or sections that are folded up from the abrasive surface, or pitted indentations that have a grating effect. One way of providing a helical coil having an abrasive surface is to wrap a second wire, or multiple wires, helically around a core wire as described below and shown in the figures. The second wire may have a round, flat, polygonal, triangular, square, rectangular, x-shaped, or star-shaped cross-section, so long as the combination of the elongated element (core wire) and the helically wound second wire create an abrasive lumen engaging surface capable of denuding the lumen when moved axially along the lumen in the deployed configuration. Wires may not be the only type of material wrapped around a central core wire or central housing, for example a polymer-based moulding, fins, abrasive granules, or spot welds. Another way of making a serrated surface is to score indentations in the surface of the coil, or to fabricate raised formations on the surface, for example helical indentations or formations. The surface should be abrasive enough so as to denude the lumen following a single longitudinal passage of the device to avoid the requirement of multiple passes which could be restricted by initial vasospasm. A preferred configuration includes surface elements to create both a macro and micro abrasive surface. The macro abrasive surface comprises grooves, indentations or teeth of at least about 0.5 mm in height (for example. 0.5 to 1.0 mm) from peak to trough.

Figure 64:
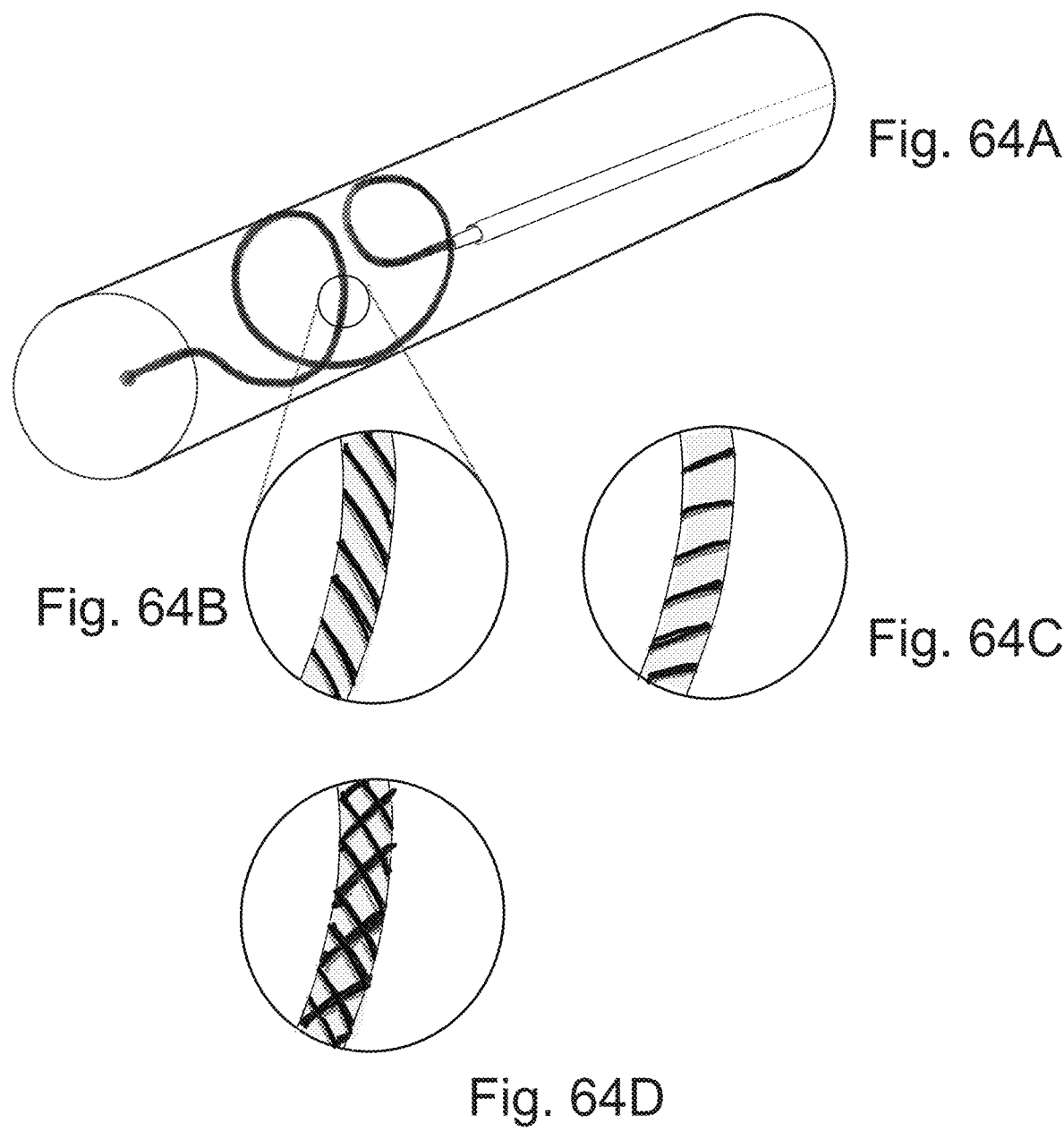
FIGS. 64A to 64D illustrate an oblique view of the device within the vessel. Close-up views of the outer texturing embodiments show (B) a macro-abrasive grooved surface that is perpendicular to the vein wall in the direction of withdrawal; (C) a macro-abrasive surface that is parallel to the vein wall in the direction of withdrawal; (D) a diamond configuration of a macro-abrasive surface.

The micro surface comprises grooves, indentations or teeth of about 5 to 100 microns in height from peak to trough. These grooves cause abrasion and prevent clogging of the abrasive surface by cellular debris over the treatment length. The orientation of the macro abrasive grooves is important as they should not be parallel but perpendicular to the axial direction of withdrawal. This is illustrated in FIG. 64 which shows a device deployed in a vessel. A detailed view of the coil surface is shown in the enlarged views in FIGS. 64B, 64C, and 64D. FIG. 64B illustrates a groove pattern perpendicular to the vessel wall on withdrawal which is effective for causing mechanical ablation. FIG. 64C shows an orientation that lies parallel to the vein wall during withdrawal and is less effective. Due to the variability in vessel diameter and tortuosity in venous anatomy a macro-abrasive texture pattern in required to overcome this problem. FIG. 64D illustrates a diamond knurled pattern which is ideal to ensure part of the macro abrasive surface is always perpendicular to the vein wall during engagement when the device is withdrawn axially. The micro abrasive surface may have a surface roughness or RA value typically between 0.8 and 3.2 to achieve endothelial disruption and prevent excessive static friction. The RA value is the arithmetic average of the absolute values of the profile height deviations from the mean line, recorded within the evaluation length. An RA value of 0.8 corresponds to average peak to trough heights of 4 μm. Endothelial Cells (ECs) are protected in most vessels from direct exposure to flowing blood by an acellular layer known as the glycocalyx. This gel like structure is typically of thickness 0.5-3 μm, exceeding that of the ECs (0.2-2.0 μm) themselves.

As used herein, the term "shape memory material" should be understood to mean a material, typically a metal alloy, that remembers its original shape and that when deformed or forced into a different configuration, returns to its pre-deformed shape when deformation forces are released. An example is Nitinol. In one embodiment, the coil, or the core element of the coil, is formed from a shape memory material. Methods for making the coil from a shape memory material generally involve the steps wrapping the shape memory alloy around a die or heat setting fixture so it forms the desired shape post heat setting, placing the loaded fixture into an oven for a set temperature/time and the removing and cooling the piece. It is also possible to form the shape from a cylindrical piece of tubing that is laser cut to the desired size. It may also possible to fabricate this shape memory by other means, for example electro activated polymers.

As used herein, the term "treatment zone" as applied to a body lumen, vessel or superficial vein refers to a cylindrical section of a body lumen that is involved in the pathogenesis of a disease state and is typically 1 cm or greater in length. In the context of a superficial vein, the term "treatment zone" should be understood to mean a cylindrical section of the lumen of the superficial vein that fails to circulate blood effectively, and is typically 1 cm or greater in length. In one embodiment, the treatment zone is 1-50 cm, 1-40 cm, 1-30 cm, 1-25 cm, 1-15 cm, 1-10 cm, 5-50 cm, 5-40 cm, 5-30 cm, 5-25 cm, 5-15 cm, 5-10 cm, 10-50 cm, 10-40 cm, 10-30 cm, 10-25 cm, or 10-15 cm, in length.

As indicated in FIG. 1, veins comprise of 3 primary cellular layers: an outer adventitia layer made up of tough fibrous tissue and unmyelinated nerve fibres, a media layer made up of collagen and smooth muscle cells and an inner endothelial layer comprised of a single layer of squamous cells and some connective tissue. In addition, the endothelial layer is covered by the acellular glycocalyx which is typically an evenly distributed structure of thickness 0.5-3 μm.

Veins have thinner walls than arteries and are less rigid and more compliant. Unlike arteries which retain their cylindrical shape at all times, veins can empty of blood and collapse down or alternatively stretch significantly to accommodate increased volumes of blood.

Vein spasm or constriction occurs in response to physical stretch activating nerves on the outside of the vein wall. Constriction also occurs when chemicals such as endothelin-1 are released by the endothelium in response to stretch or disruption.

The endothelial layer prevents blood from clotting in veins. If the endothelium is disrupted or damaged, pro-thrombotic factors are exposed which platelets will immediately adhere to and the clotting cascade will begin. Over time (4-12 weeks, typically an average of 8 weeks) clot within a vein becomes fibrotic as it is invaded by surrounding cells which deposit fibrin and collagen in a process known as sclerosis or fibrotic transformation. This prevents blood reflux in the vein and thus successfully treats the varicose vein.

The aim of the device is to disrupt the endothelial and media layers of the vein but not the outer adventitia layer. This requires selective controlled mechanical disruption to a depth of at least 5 μm and up to but not exceeding 100 μm. This ensures endothelial and superficial medial layer disruption without deeper media/adventitial disruption which can lead to pain and/or perforation. There may be further cell death in deeper layers due to intracellular content release causing apoptosis in adjacent cells and continuing in a cascade over time to a depth of up to 300 μm. The resultant thrombosis or clot and fibrous scar tissue prevents blood from entering the vein and thus the appearance and symptoms associated with varicose veins. It is important that the endothelium is completely circumferentially disrupted as if small areas are left intact, clot may not form and blood will continue to flow leading to treatment failure and/or early recurrence. This is likely to occur when liquid or foam chemical sclerosants are used in large veins and is the suspected cause of poor efficacy rates of only 70% compared to 90-98% with thermal treatments.

As the treatment begins two or more centimetres back from the junction to the deep veins, the attached created thrombus is confined to the superficial vein and as there is no blood flow it cannot be carried into the deep system where it can cause complications.

The precise requirements for successful long-term vein ablation are currently unknown. Some experts in the treatment of superficial venous reflux propose that complete endothelial damage is sufficient. This leads to thrombus formation and discontinuation of blood flow, the body then converts the thrombosed vein into a fibrous cord in a process known as sclerosis or fibrotic transformation, achieving long-term ablation. Others argue that damage of vein wall tissue into the deeper media layer, in addition to the inner intima layer, is required for long-term vein ablation. Others such as thermal ablation proponents propose that complete transmural damage of the vein wall from the intima to the outer adventitia layer is required.

A device of the present disclosure may achieve complete circumferential endothelial damage by its oversized coiled configuration with abrasive surface. It also causes media layer damage by at least three separate mechanisms. Firstly, the abrasive polygonal coil surface can penetrate to over 50 μm allowing damage to occur deeper than the intima layer. This could also be further increased by the use of more than one coil allowing the second abrasive coil, located more distally on the device, to penetrate deeper into the vessel wall section that has already been denuded by a coil more proximally on the device. This could also be achieved by repeating the procedure over the same treatment length using the same device. Secondly, it has been shown in studies of foam sclerotherapy that cell death occurs up to 300 μm into the vein wall [10]. This is likely due to a cascading effect of cell death caused by release of molecules by damaged cells signalling apoptosis to occur in neighbouring cells. In this manner cell vein wall damage can occur deeper to the superficial cells affected by mechanical destruction. Thirdly, frictional forces caused by the device acting on superficial layers combined with resistance of deeper media layers have a shearing effect within the vein wall layers resulting in deeper vessel wall damage. This effect has been reported in previous studies and was also seen on pre-clinical testing of the present disclosure.

The risk of vein rupture and/or snagging of the device is proportional to the abrasiveness or sharpness of the device in contact with the wall causing frictional or cutting forces respectively and the depth that the abrasive elements penetrate into the wall. Snagging is a commonly reported pain point for physicians and patients following the use of current mechanochemical devices. There are even documented cases where the vein was snagged and stripped out inadvertently leading to pain and haematoma formation known as "inadvertent spontaneous stripping" [6]. Vein valve leaflets also represent an obstacle where a mechanical tip can become stuck and lead to snagging.

The key problem therein is the difficulty in completely removing the endothelial layer and partially damaging the media layer without causing excessive resistance and/or snagging.

Figure 2:
FIG. 2 is a histological axial section of a caprine vein 28 days post mechanical endovenous treatment in our animal study. The image highlights the importance of circumferential coverage in terms of endothelial cell destruction. It is taken from a partially treated vein in our animal study. The upper right corner shows a clot adherent to the vein wall with inflammatory cell migration into the thrombus from the outer layers in the early phases of fibrotic transformation. The lower left corner has intact endothelium remaining. Thrombus has failed to adhere or has recanalised due to the effect of the intact endothelium. Blood can flow in the channel leading to overall treatment failure in this segment.
Figure 3:
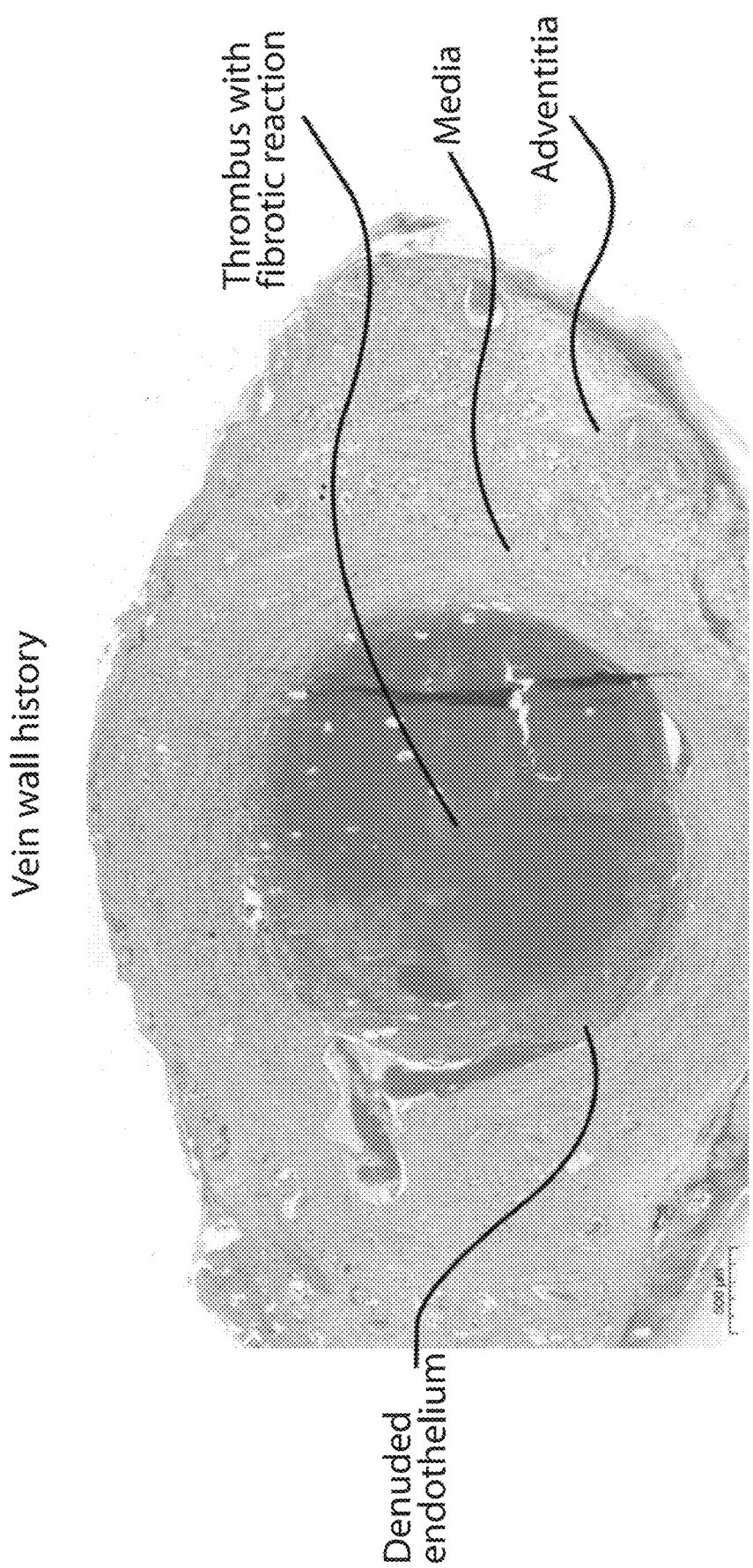
FIG. 3 shows a histological axial section of a goat vein at 28 days post mechanical endovenous treatment in our animal study. Circumferential denudation of the endothelium and shearing due to frictional forces between superficial and deep layers has occurred. The lumen is filled with adherent thrombus undergoing fibrotic change as it is invaded by inflammatory cells including collagen forming fibroblasts.
Figure 4:
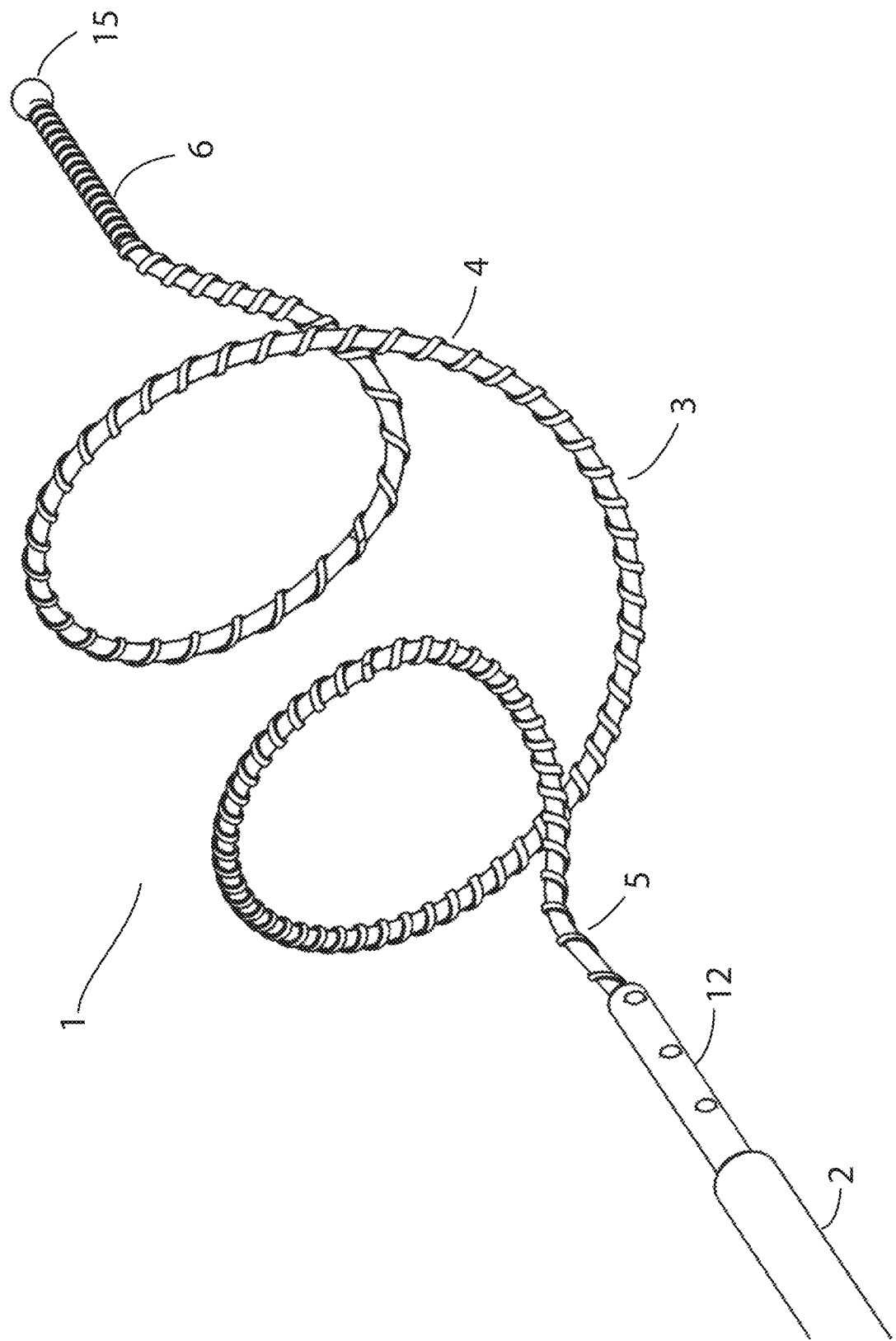
FIG. 4 illustrates a device for denuding a body lumen according to a first embodiment of the disclosure.
Figure 5:
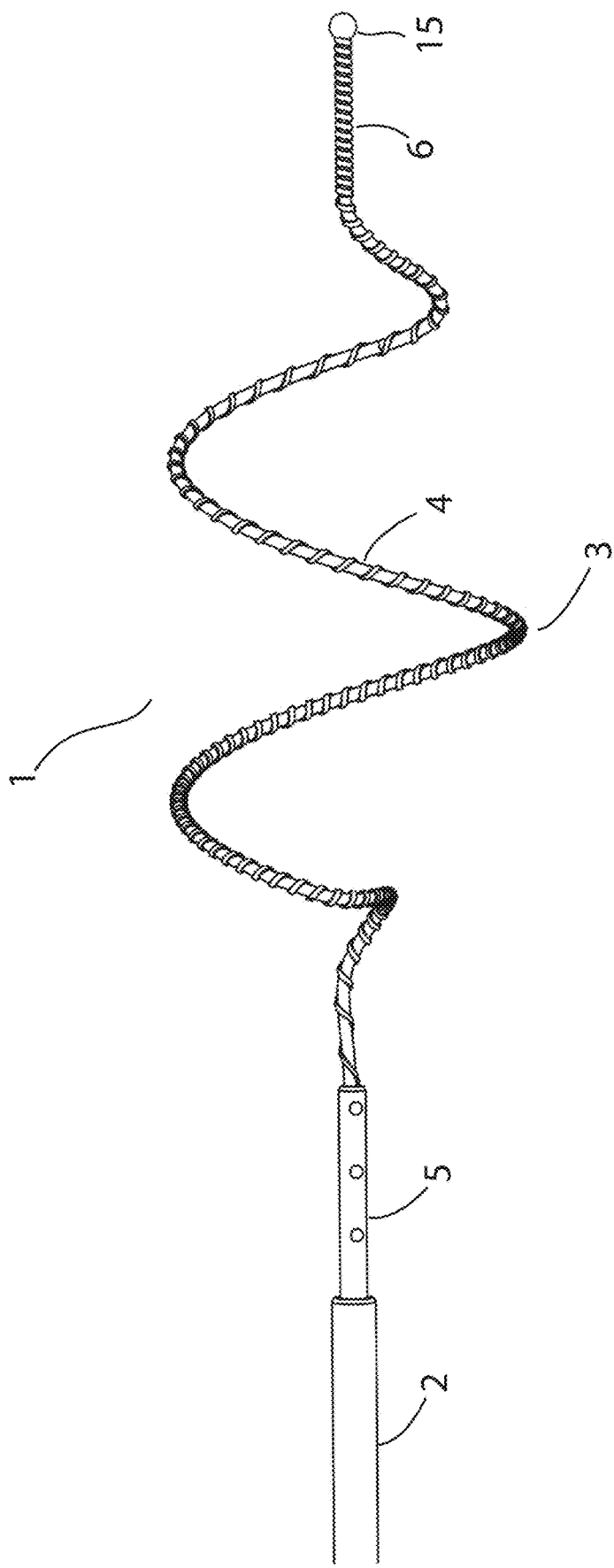
FIG. 5 is a side elevational view of the device of FIG. 1.
Figure 6:
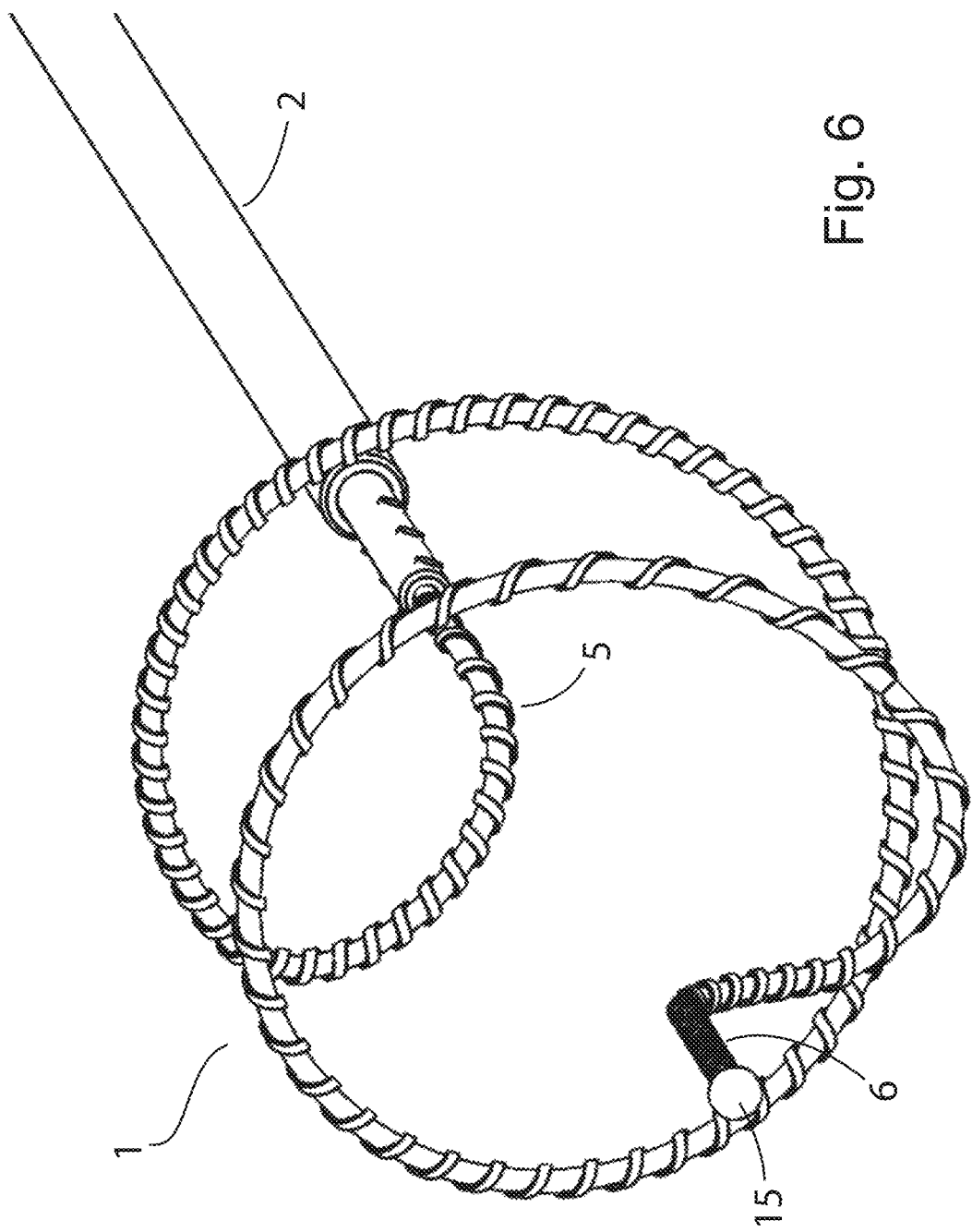
FIG. 6 is a perspective view of the device of FIG. 1.
Figure 7:
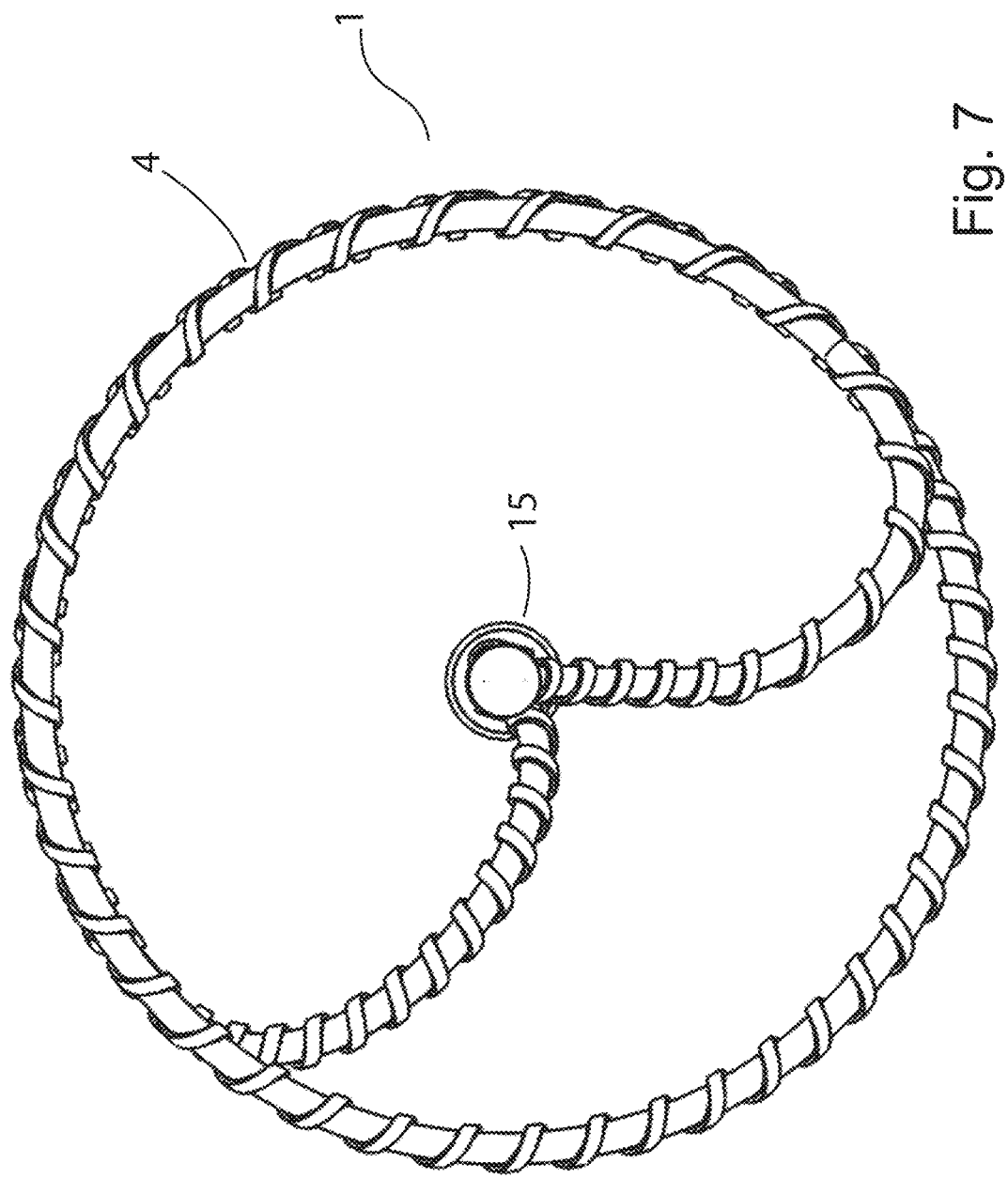
FIG. 7 is a distal end elevational view of the device of FIG. 1

FIG. 2 highlights the importance of circumferential coverage in terms of endothelial cell destruction. It is taken from a partially treated vein in our animal study. The upper right corner shows a clot adherent to the vein wall with tissue invasion as it starts to become fibrotic at 28 days post procedure. The lower left corner has intact endothelium remaining. No clot has formed and blood can flow in the channel leading to overall treatment failure in this segment. Conversely, FIG. 3 illustrates the results of full endothelial coverage and damage at 28 days post procedure with adherent thrombus formation obliterating the entire vessel lumen preventing blood flow resulting in treatment success. Inflammatory cell migration from the adventitia into the thrombus can be identified on microscopic examination. This leads to fibrotic transformation of the thrombus and long-term occlusion.

Devices and methods of the present disclosure will now be described with reference to specific embodiments. These are merely exemplary and for illustrative purposes only: they are not intended to be limiting in any way to the scope of the claimed invention. These examples constitute the best mode currently contemplated for practicing the invention.

Referring to the drawings, and initially to FIGS. 4 to 7, there is illustrated a device according to the present disclosure for denuding a body lumen, indicated generally by the reference numeral 1. The device 1, which in this embodiment, is a device for denuding a varicose vein for the purpose of causing occlusion of the vein and thereby treating the varicose vein, comprises a polyimide catheter member 2 and a denuding head 3 configured for transluminal delivery to a section of a varicose vein to be treated, and deployment at the target location in the vein. The denuding head 3 comprises a helical coil 4 having a proximal end 5 and a distal end 6, which are generally co-axial with an axis of the helical coil, and a coiled part having about 1.5 rotations, an outer diameter of 13 mm, and a pitch of about 9 mm.

The helical coil 4 is axially adjustable with respect to the catheter member from a delivery configuration (not shown) in which the coil is unwound and stowed in a distal end of the catheter member 2, and a deployed, coiled, configuration, shown in FIGS. 4 to 7. The helical coil comprises a shape memory alloy, and is biased to assume the coiled configuration when it is extended beyond the distal end of the catheter member. The device is suitable for use in a varicose vein having a normal diameter of 4-12 mm (i.e. where the coil is oversized with regard to the vein to be treated).

It will be noted that the "oversized" diameter of the helical coil extends along at least one full loop of the coil (360 degrees). This feature, added to the oversized diameter of the coil relative to the vein, ensures that the coil engages and impresses circumferentially against the inner lumen of the vein, exerting radial pressure evenly around the full circumference of the vein. It is possible for the oversized diameter to extend along less than one full loop, for example at least 300 degrees, however this leads to a risk that the inner lumen of the vein will be incompletely denuded resulting in partial vein occlusion and subsequent recanalisation. In this embodiment, the coil has just over one complete turn, to allow complete coverage even when stretched while not being too long to cause increased friction against the vein wall and snagging. The addition of further coil turns in a longer coil can be used to induce further mechanical damage into the vein wall. The increased surface area of the device in contact with the vein in such an embodiment would also increase the risk of snagging and vein wall damage. Therefore, a coil with just over one complete turn represents the most efficient method of attaining complete denudation of the vessel inner surface.

The coiled configuration and flexible material of the denuding head allows it to adapt to different vein diameters within a range of sizes which are smaller than the diameter of the coil while still exerting adequate radial force to cause denudation. These properties also enable the coil to adapt to changing vein diameters within the same vein over its target treatment length. These changes may be due to the natural tapering of the vein or due to venous valves. The latter can cause significant snagging and vein perforation if rigid structures become caught or trapped by the valve leaflets. Due to the flexible nature of the coil and minimal protrusions of the abrasive components this is unlikely to occur. In the event of the device being caught by valve leaflets, a resultant small increase in force along the longitudinal axis will automatically decrease the diameter of the coil, while increasing its length, allowing the coil to free itself and avoid snagging or detaching the valve and associated leaflets, illustrated in FIGS. 60A-60C and 61A-61C. This will occur automatically during normal withdrawal of the device within the vein and does not require adjustment, extra manoeuvres or supplementary imaging to be performed by the operator.

Figure 8:
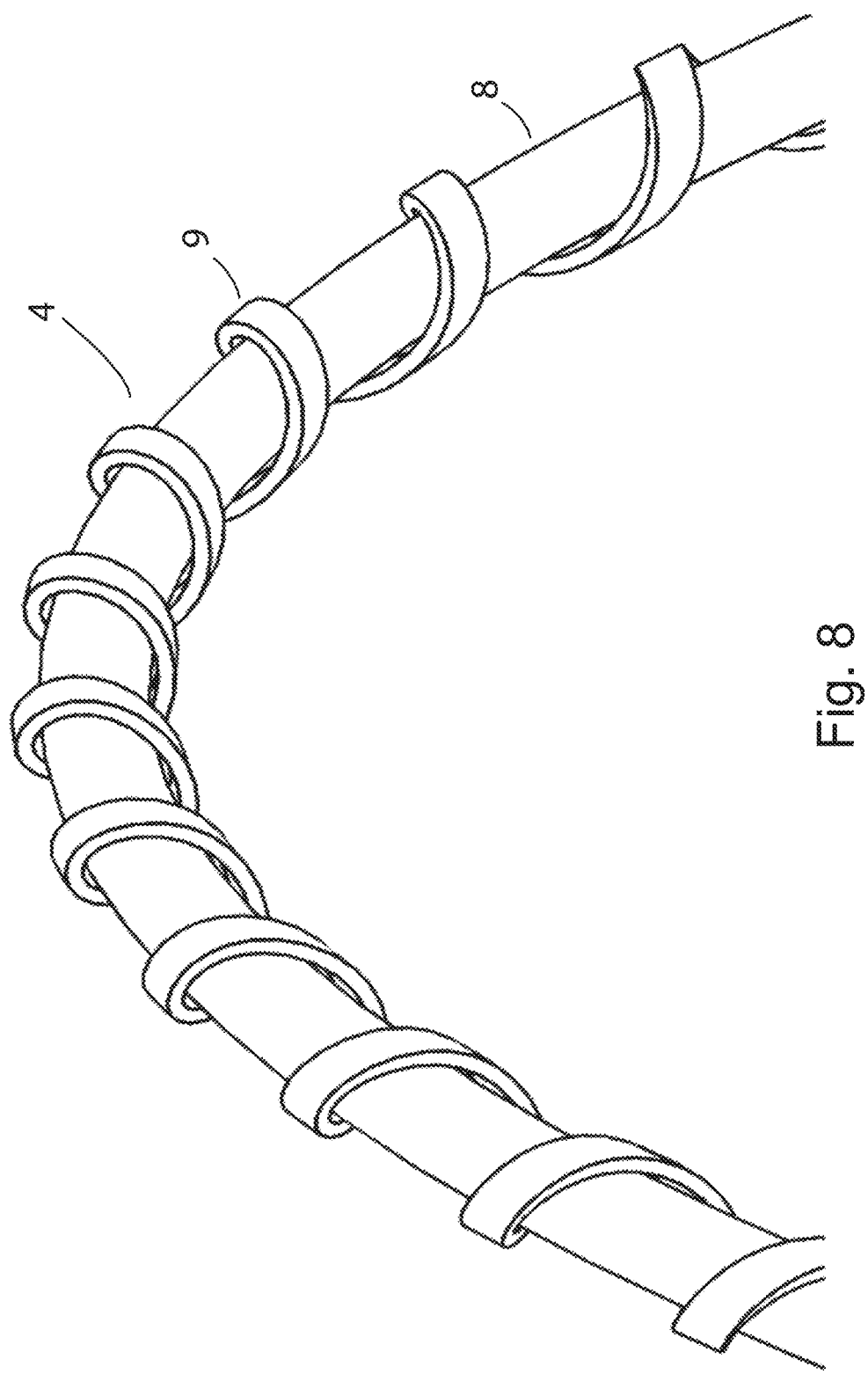
FIG. 8 is a detailed view of a section of the helical coil of the device of FIG. 4, showing the serrated surface formed by the second wire helically wound around the core wire.
Figure 9:
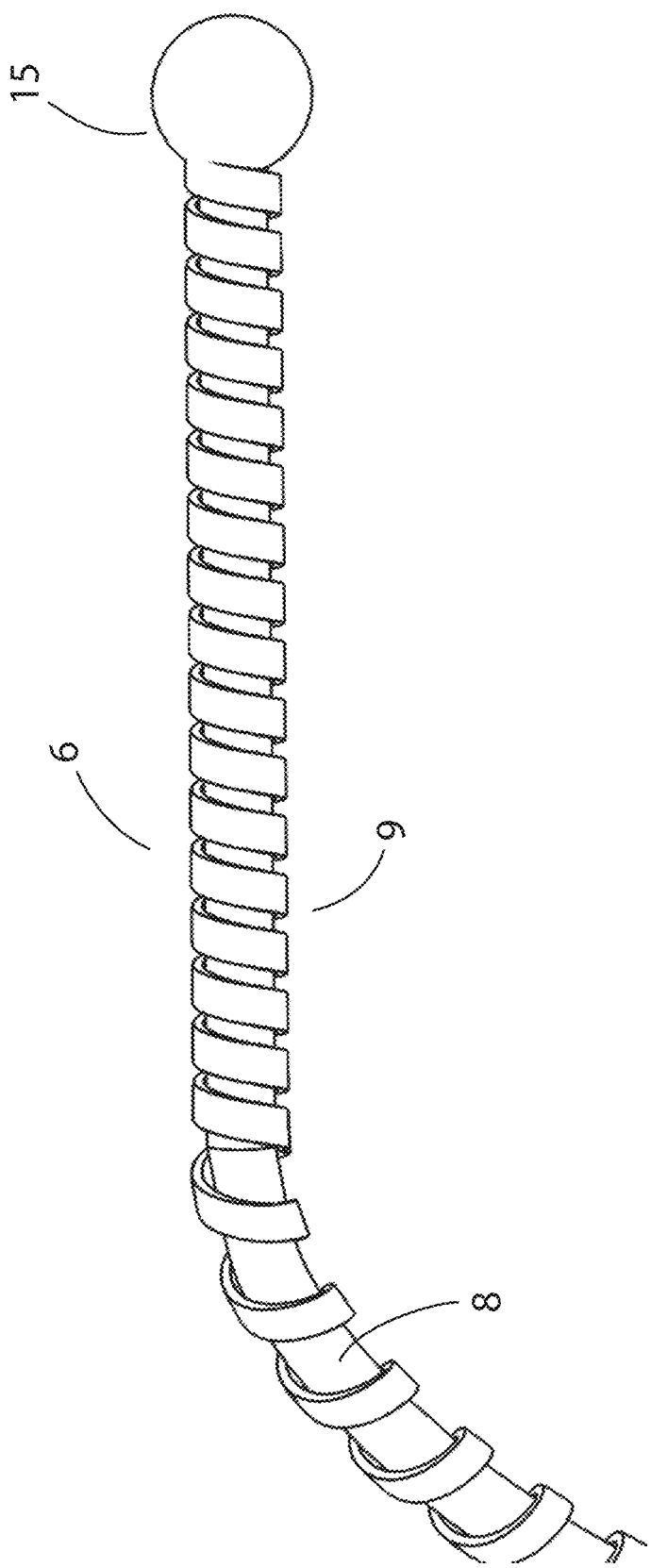
FIG. 9 is a detailed view of a distal end of the helical coil of the device of FIG. 4, showing the higher pitch of the second wire and the spherical end-hub.
Figure 10:
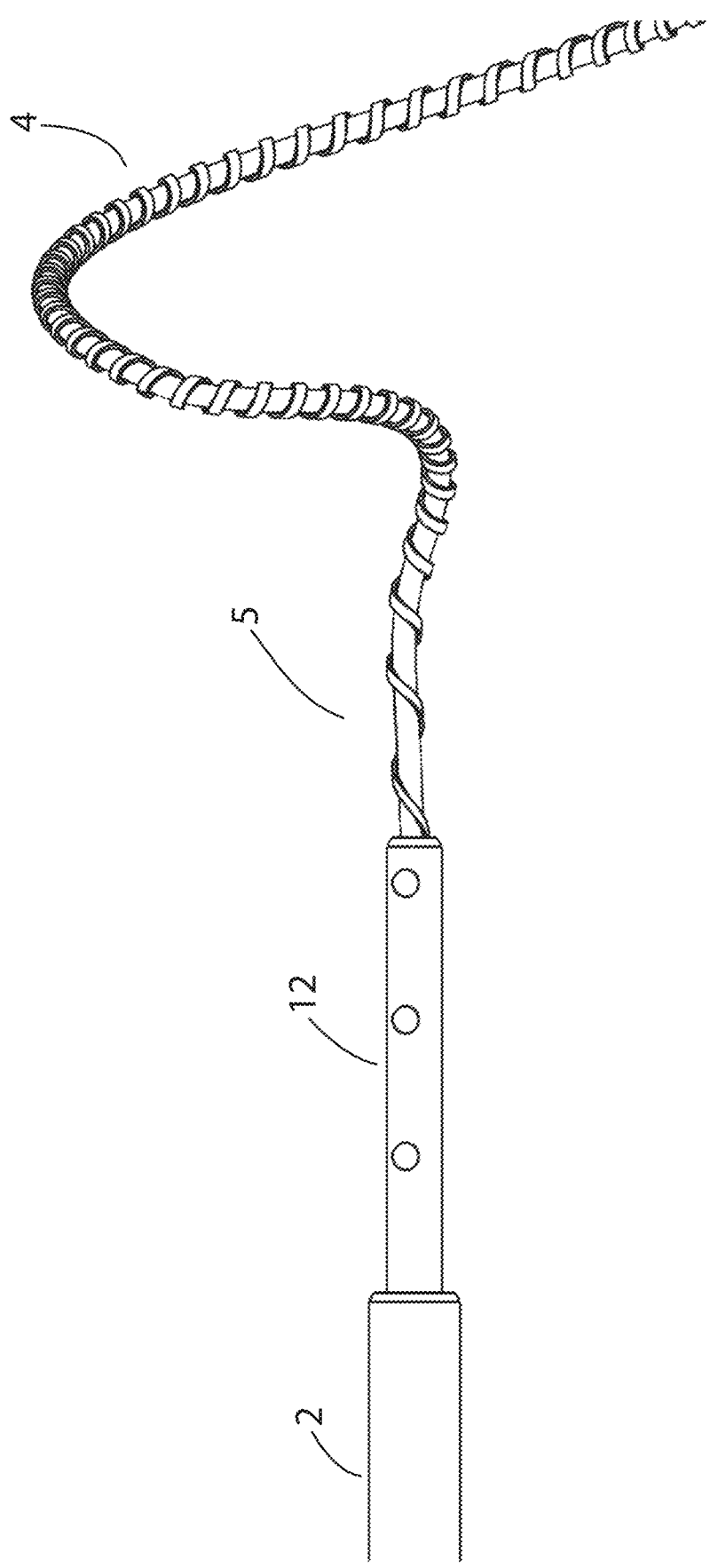
FIG. 10 is a detailed view of a proximal end of the helical coil of the device of FIG. 4, showing the helical coil attached to a steel hypotube, which is mounted within the catheter member.

Referring to the drawings, and initially to FIGS. 8 and 9, the helical coil 4 has an abrasive surface configured to shear the inner lining of the vein (primarily but not limited to the endothelial cell layer) away from the vein when the helical coil is moved axially along the vein when in a deployed configuration. In this embodiment, the helical coil comprises a 0.01181" NITINOL core wire 8 and a second wire 9 helically wound around the core wire 8 forming an abrasive, serrated, surface on the helical coil 4. Referring to FIGS. 8 and 9, the second wire 9 is a flat wire that is formed from stainless Steel or Nitinol. In this embodiment, the core wire 8 has a diameter of about 1 mm and the second wire 9 has width of about 0.7 mm and a thickness of about 0.02 mm. The pitch of the second wire is about 1.5 mm. Referring to FIG. 9, the pitch of the second wire 9 on the core wire 8 reduces at the distal end 6 of the helical coil 4, in this case to about 0.3 mm. The purpose of the smaller pitch/closed pitch at the distal end is to form a flexible distal member of the device to help navigate the device to the target anatomy. Referring to FIG. 10, the pitch of the second wire 9 on the core wire 8 increases at the proximal end 5 of the helical coil 4, in this case to a maximum of about 3 mm. The purpose the higher pitch at the proximal end is to assist in the smooth recapture of the distal tip following the procedure. This proximal partition could also have a closed section with a lower, tighter pitch to aid recapture.

The thickness of the second wire 9 is between 0.1 and 1 mm. Based on testing using equivalent animal venous tissue, a diameter of greater than 1 mm will carry the risk of creating a surface protrusion which can snag or stick to the vein wall surface.

Figure 11:
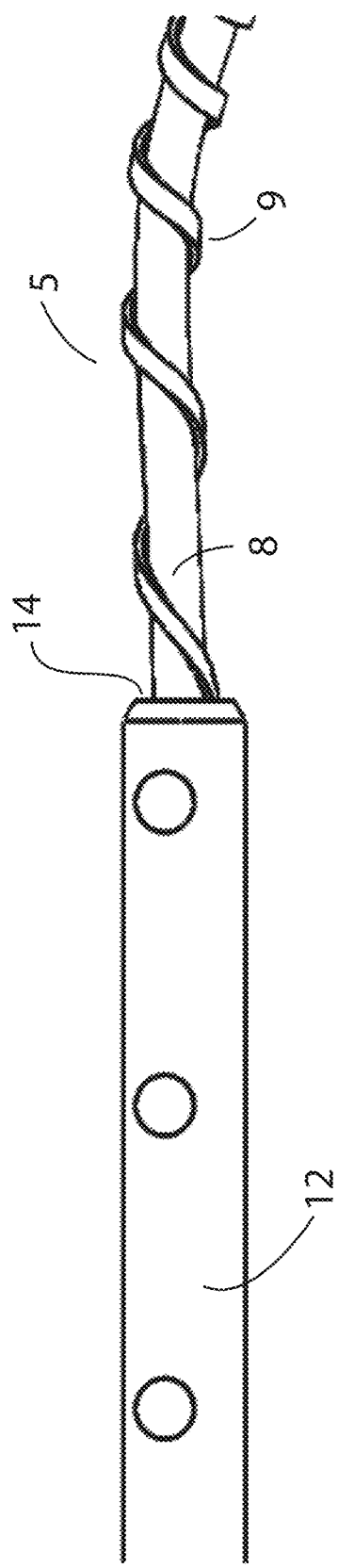
FIG. 11 is a detailed view of a proximal end of the helical coil of the device of FIG. 4, showing the shorter pitch of the second wire as it approaches the proximal end of the coil to aid recapture.

Referring to FIGS. 10 and 11, the proximal end 5 of the coil 4 is attached to a stainless steel hypotube 12 which extends through the catheter member 2 to a proximal end thereof (not shown). In use, the hypotube 12 can be axially adjusted with respect to the catheter member 2 to effect deployment of the helical coil 4 distally of the catheter member into the coiled configuration, and retraction of the helical coil 4 into the catheter member during transluminal delivery and withdrawal of the device. In this embodiment, the catheter member 2 is 4 Fr polyimide extruded catheter tube, having an inwardly tapering mouth 14 in FIG. 11 to assist in recapturing the helical coil 4 when it is retracted into the catheter member 2.

Referring to FIG. 9, the distal end of the helical coil 4 terminates in an atraumatic head, in this embodiment provided by a smooth metal ball 15, which serves to prevent the helical coil snagging on a vein or valve and reduce the risk of the distal tip causing perforation to the vein wall when it is deployed and withdrawn. In addition, referring to FIG. 9 the ball 15 is dimensioned to nest in the tapered mouth 14 in FIG. 11 of the catheter member 2 when the device is in the delivery configuration.

Referring to FIG. 9, between the end of the abrasive coil and the distal smooth ball there is an elongated straight section of approximately 5 mm to aid navigation and placement of the device. The ball at the distal side of the device forms an atraumatic tip, in another embodiment this can be the same diameter as the diameter of the abrasive member so as to not create a ball but a straight atraumatic tip.

Figure 12:
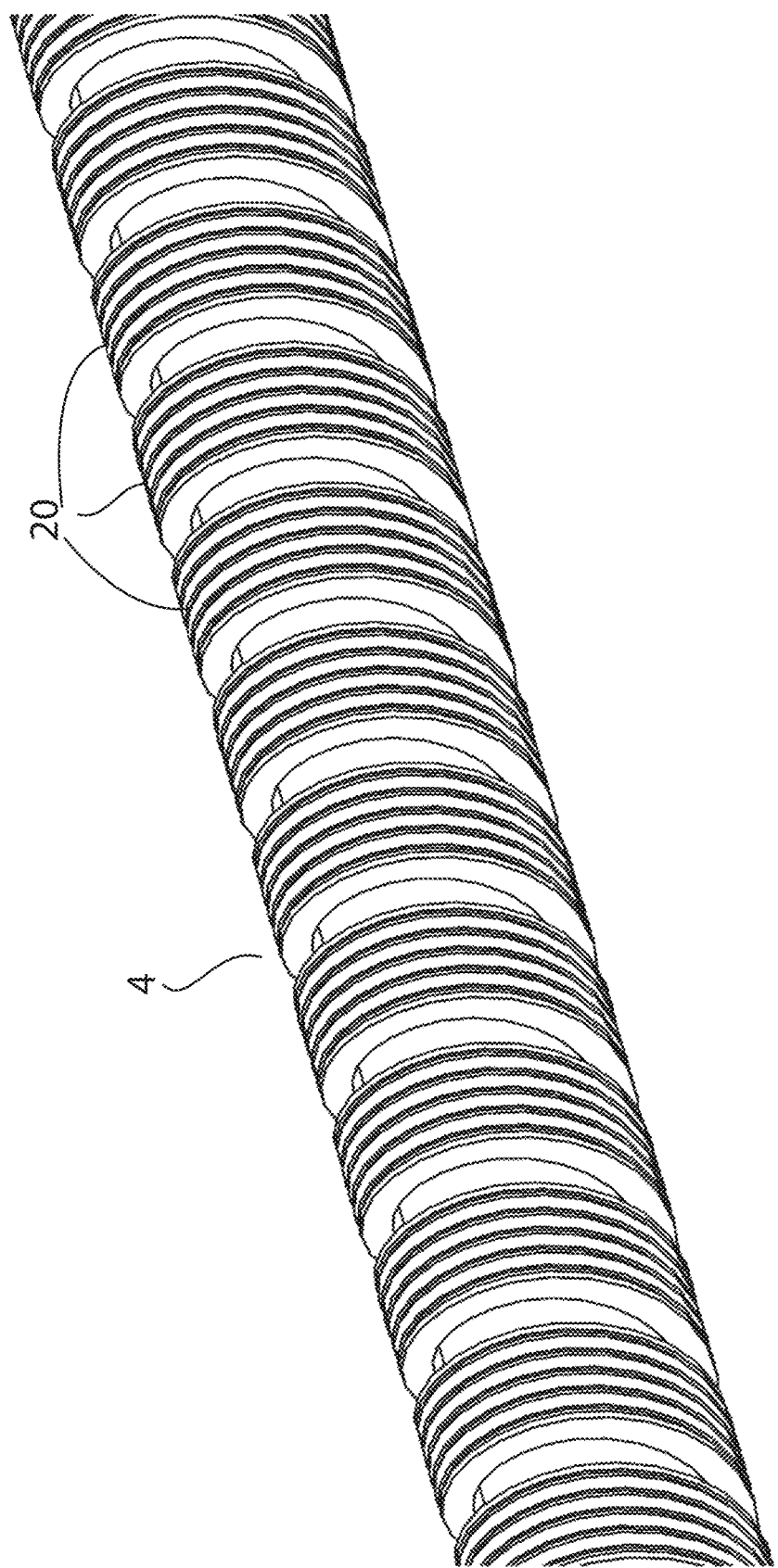
FIG. 12 is a perspective view of a helical coil forming part of a device according to an alternative embodiment of the disclosure, in which a lumen-engaging surface of the second wire incorporates a series of helical indentations.

Referring to FIG. 12 there is illustrated part of a device according to an alternative embodiment of the present disclosure, in which parts identified with reference to the previous embodiments are assigned the same reference numerals. In this embodiment, a surface of the second wire is scored with helical indentations 20 which serve to provide an abrasive, serrated, surface on the helical coil 4.

Referring to FIGS. 13 to 19, the use of the device of the present disclosure is illustrated. In the following description proximal refers to toward the access insertion site while distal refers to away from the access site in the blood vessel. The device can be delivered and removed through a single injection site and does not require any implantation or administration of chemical agents. The method of treating a vein with reflux to cause permanent occlusion may comprise the following steps.

In a first step, the device is adjusted into a delivery configuration, with the helical coil 4 retracted into the end of the catheter member (not shown). In some embodiments the catheter member is a polyimide extrusion. The device is then delivered to the target vein via a separate introducer catheter under image guidance, for example ultrasound.

The device is then navigated distally under ultrasound guidance to the required position. The correct placement, with a distal end of the catheter member 2 positioned at the beginning of the vein to be treated is verified by ultrasound shown in FIG. 17.

Figure 13:
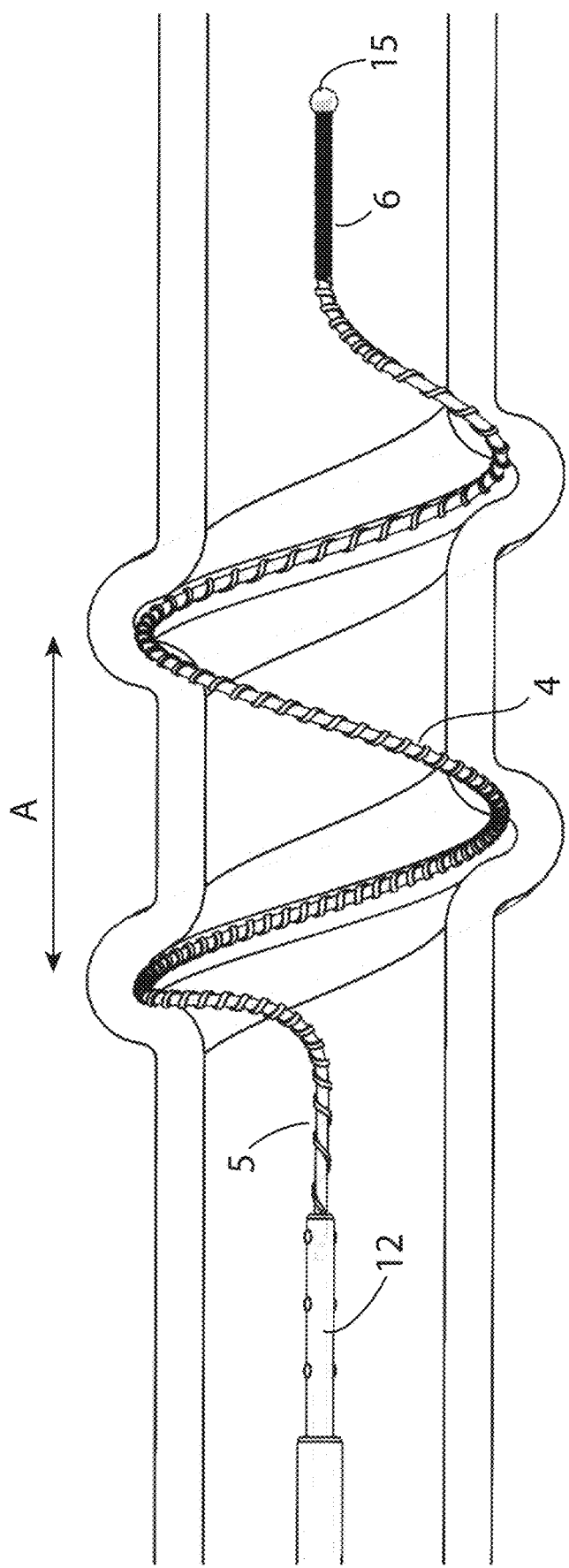
FIG. 13 is a side elevational view of the device of FIG. 4 in a vein with the helical coil in a deployed configuration. This figure illustrates how the oversized coil is forced into circumferential engagement with the body lumen, and that the radial force exerted by the oversized coil deforms the vein.
Figure 14:
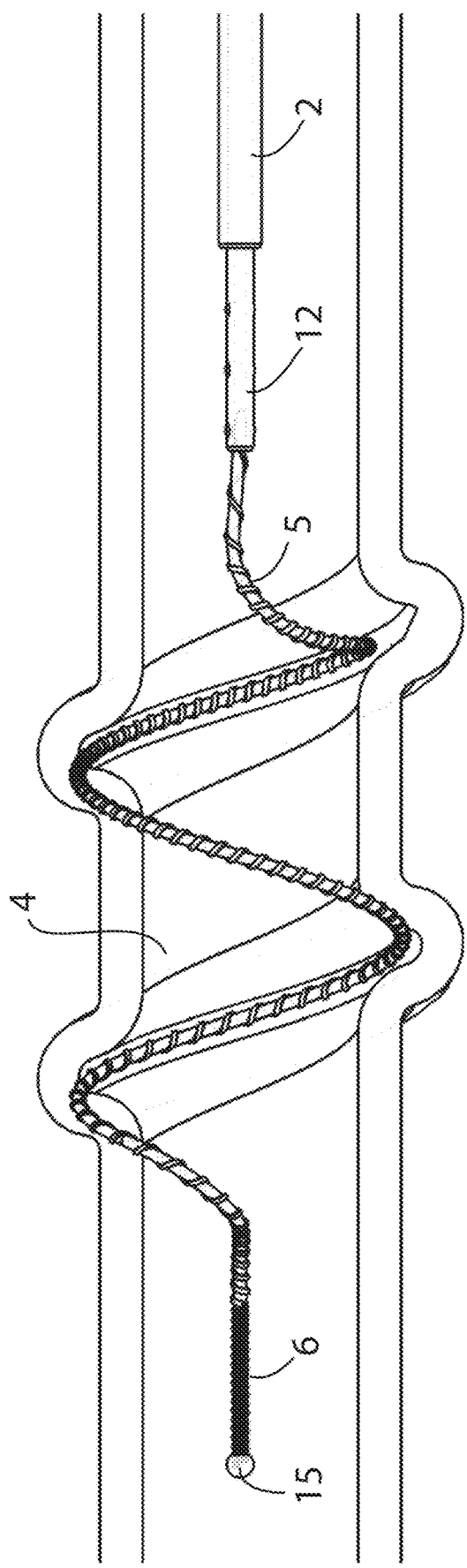
FIG. 14 is a similar illustration to FIG. 13, and shows how a smaller diameter coil is employed with a smaller diameter vein.
Figure 15:
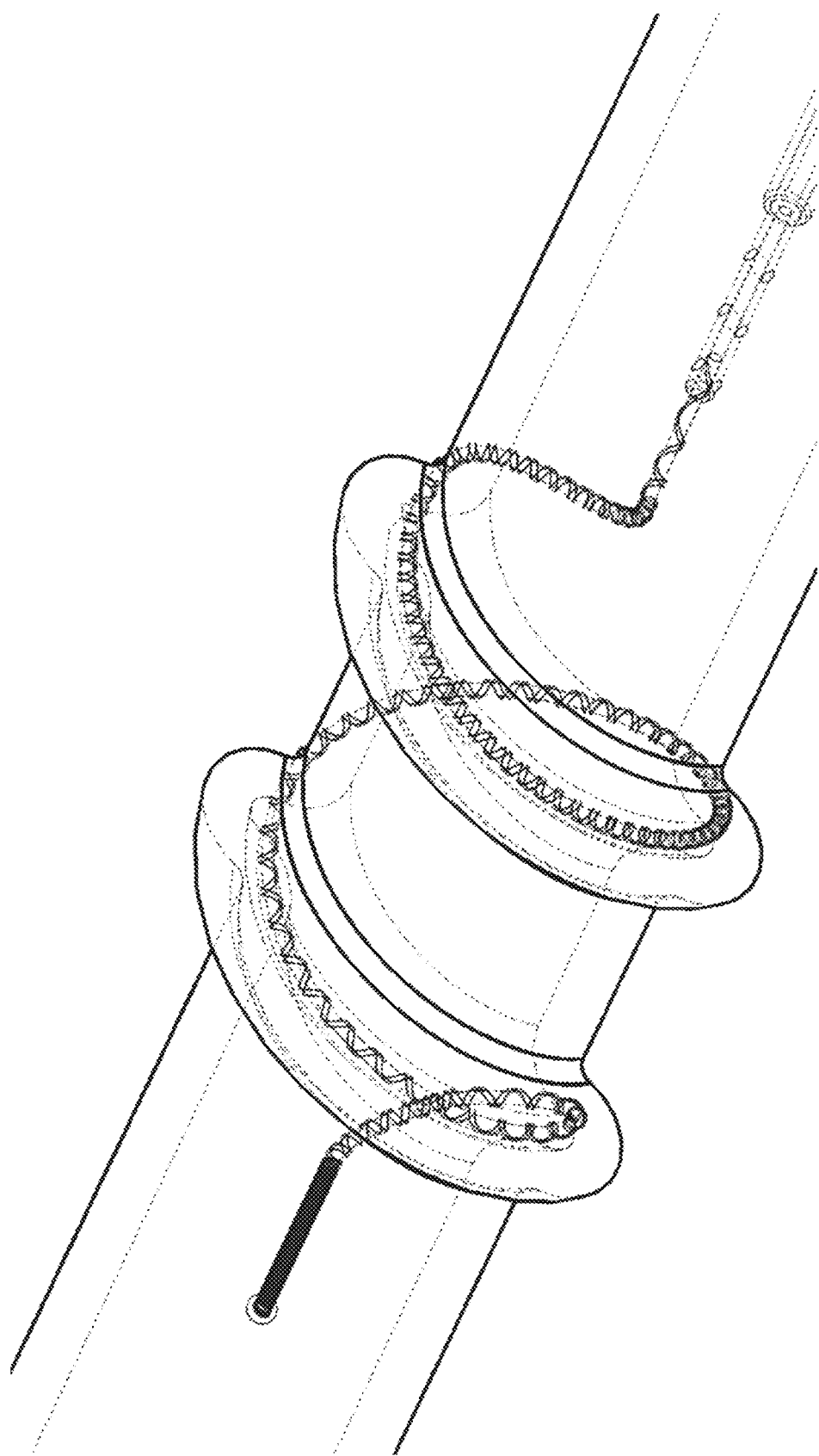
FIG. 15 is a perspective view of the device deployed in a view outside the vein, showing how the radial forces exerted by the deployed coil deform the vein.
Figure 16:
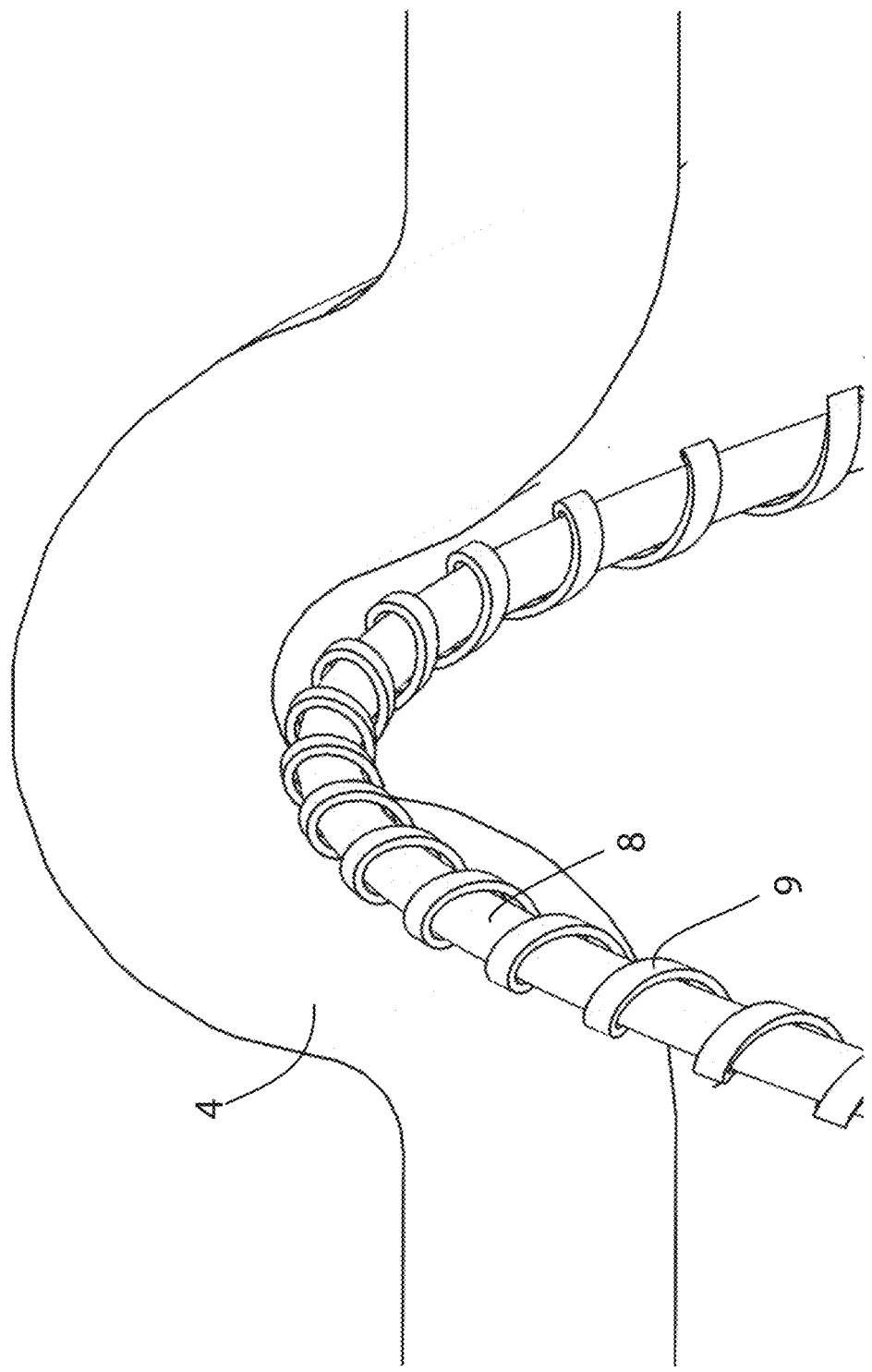
FIG. 16 is a detailed view of the abrasive surface of the helical coil engaging the inner lumen of a vein.
Figure 17:
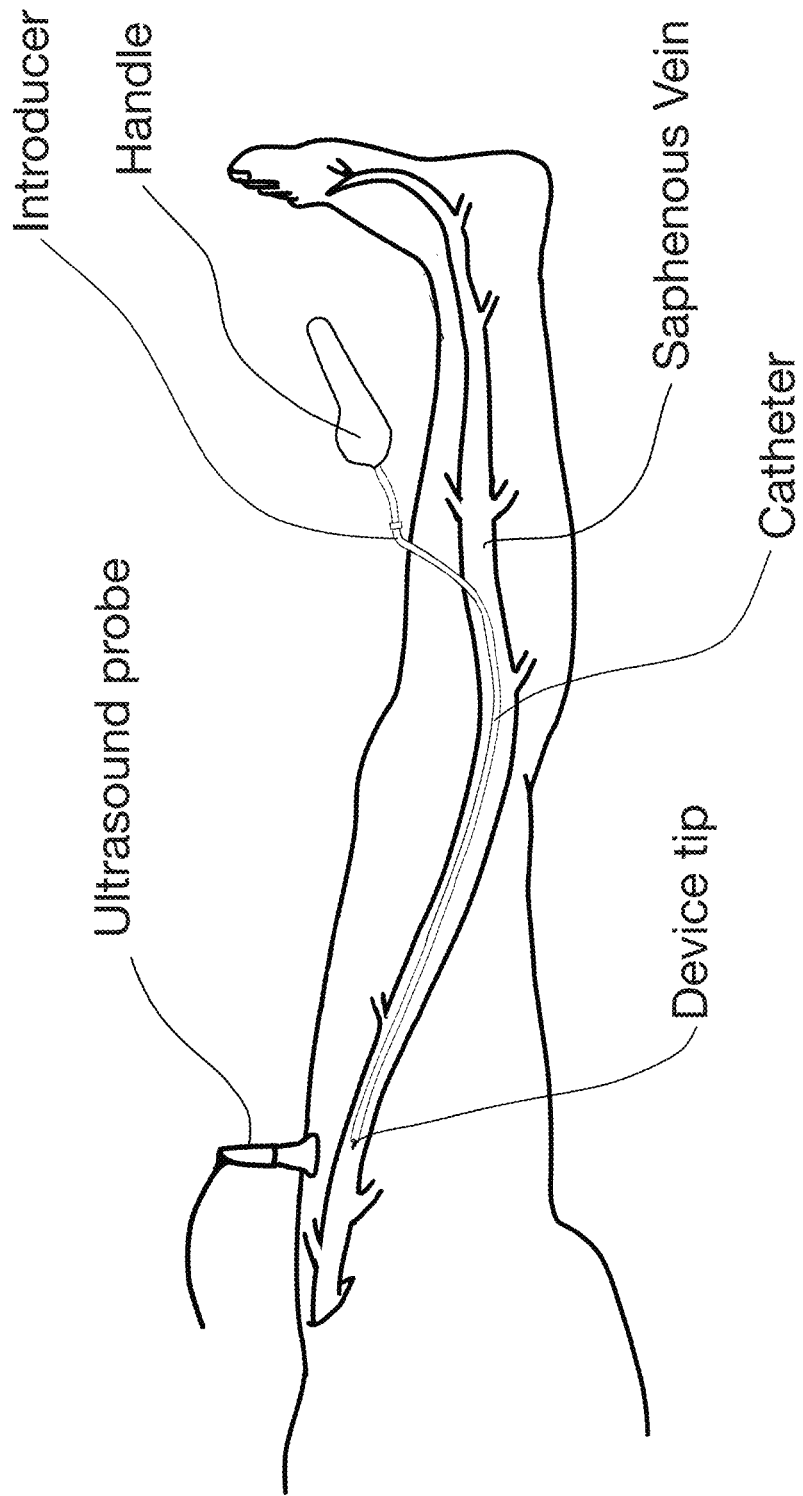
FIG. 17 illustrates the procedure of endovenous mechanical denudation of a lower limb vein to cause occlusion and prevent reflux in the treatment of superficial venous disease. The undeployed device within the outer catheter is shown near the Sapheno-femoral junction following ultrasound guided navigation.
Figure 18:
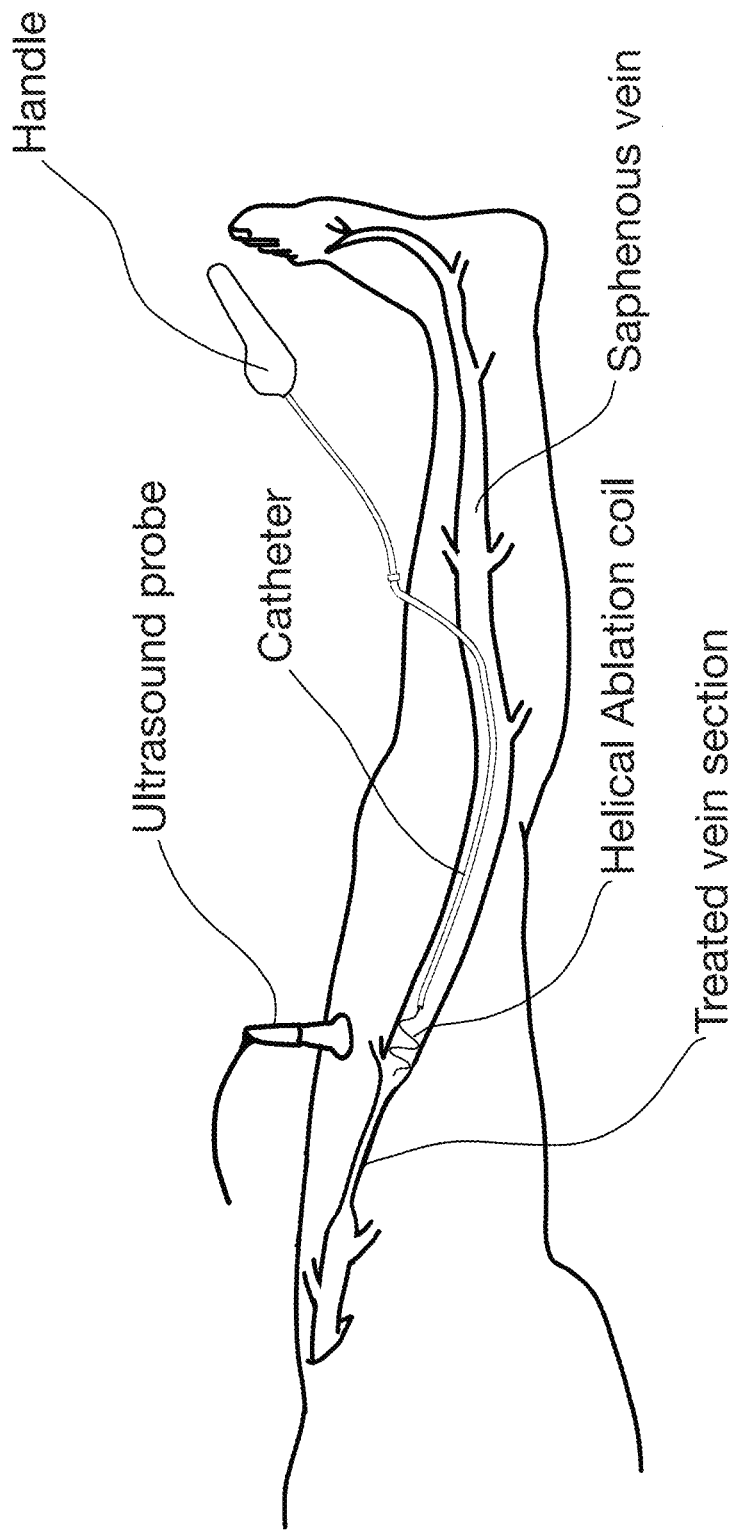
FIG. 18 illustrates the deployed radially expansive coil during treatment causing vasospasm of the treated section.

The outer catheter 2 is axially withdrawn exposing the helical coil 4 and hypotube 12, to a deployed coiled configuration shown in FIG. 13. In some embodiments, the helical coil is deployed using a handle with a thumbwheel-controlled element. Using a single handed, intuitive movement the operator can deploy the coil by turning the thumbwheel with the thumb of the hand which holds the handle. This allows simultaneous visualisation by positioning of an ultrasound probe using the opposite hand. This enables the physician to perform the procedure without an assistant if required.

The coil in both its undeployed and deployed configuration must be easily visualised on ultrasound to prevent inadvertent placement. This is achieved by incorporation of an echogenic section of material onto the tip of the catheter. In the deployed state the coil with its abrasive surface is inherently echogenic.

As the coil is oversized with respect to the vein being treated, it exerts an outward radial force against the lumen of the vein along at least one full circumference of the vein.

Unlike current treatment options, the action of the device on the vein wall to cause long term occlusion only occurs following withdrawal of the device in the vein section to be treated. This can only occur in the proximal direction which protects the more distal structure which may include veins in the deep system.

If the device is inadvertently placed in the wrong position of the target vessel it can be recaptured into the outer catheter and repositioned without causing vessel trauma.

Figure 19:
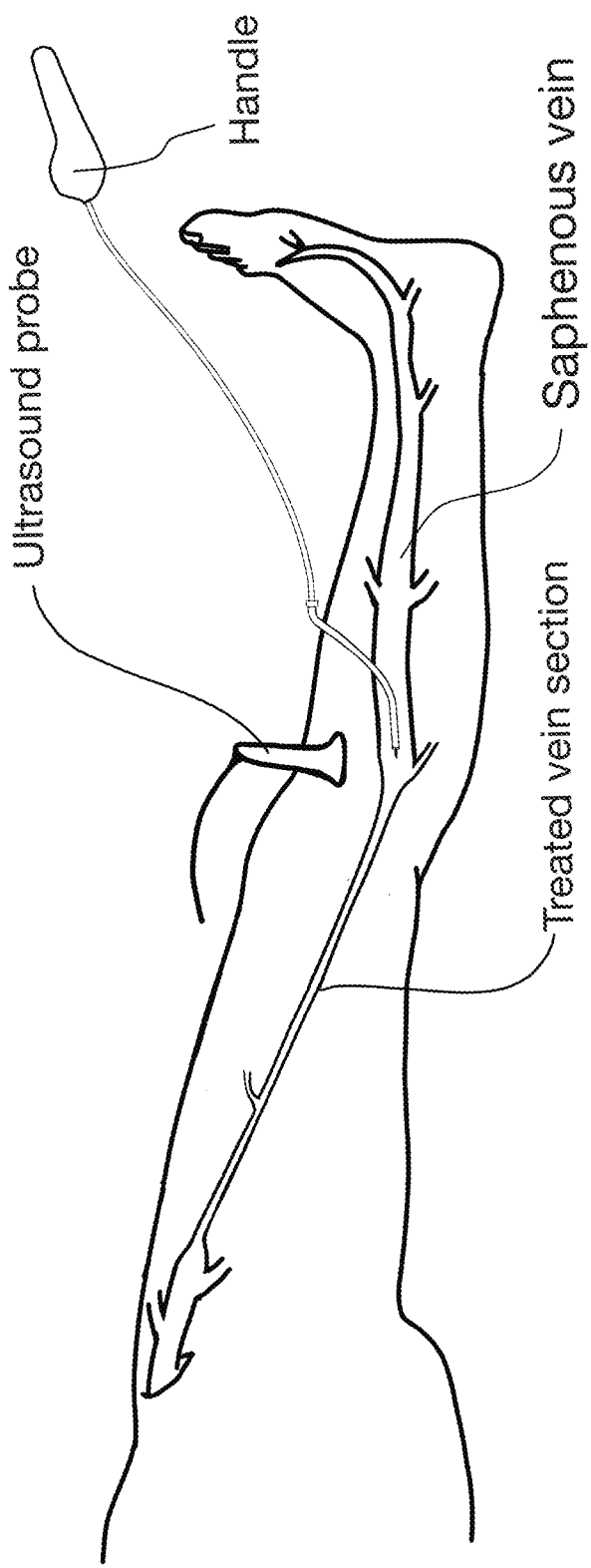
FIG. 19 illustrates recapture of the radially expansive element prior to withdrawal of the catheter.
Figure 20:
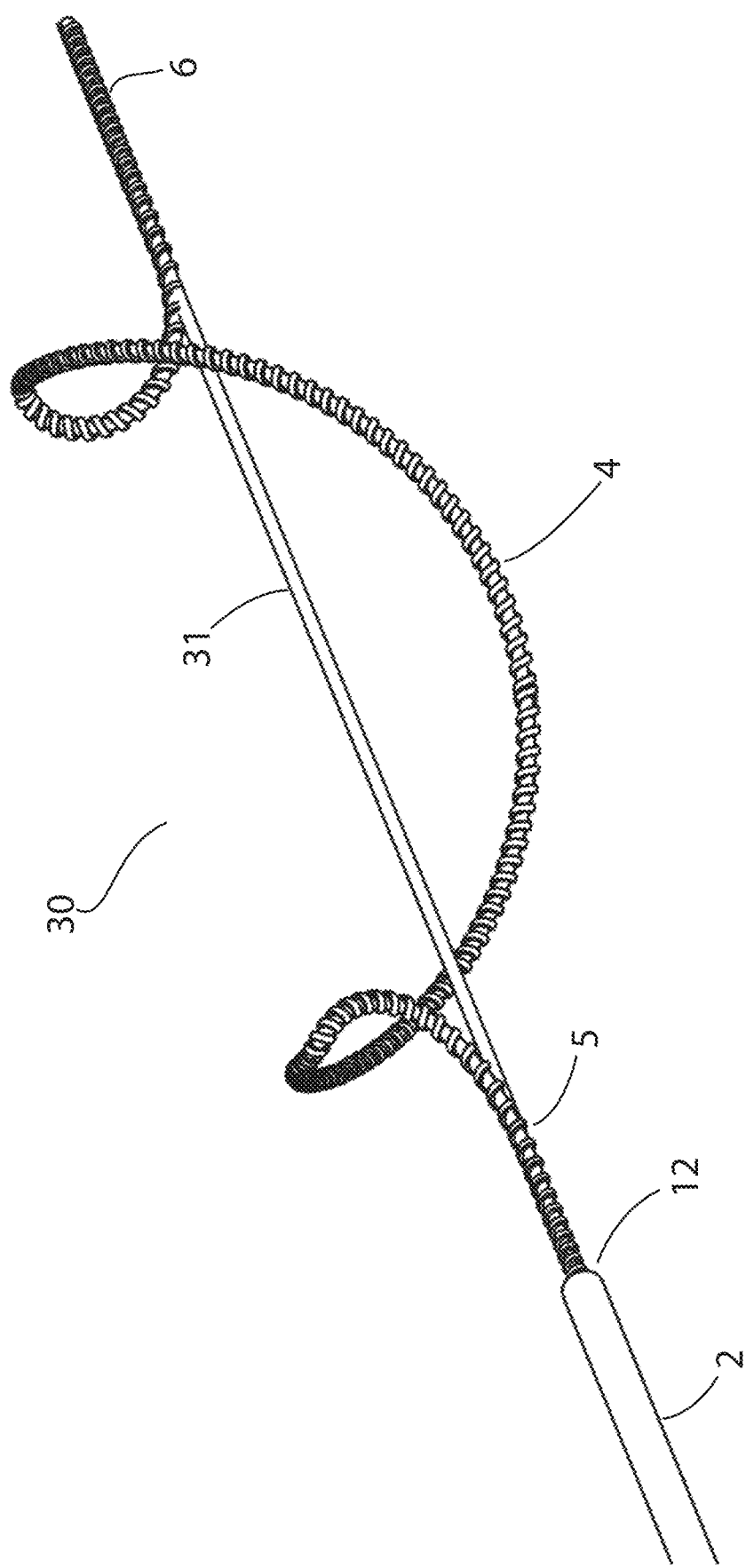
FIG. 20 is a perspective view of a device for denuding a body lumen according to a further embodiment of the disclosure.
Figure 21:
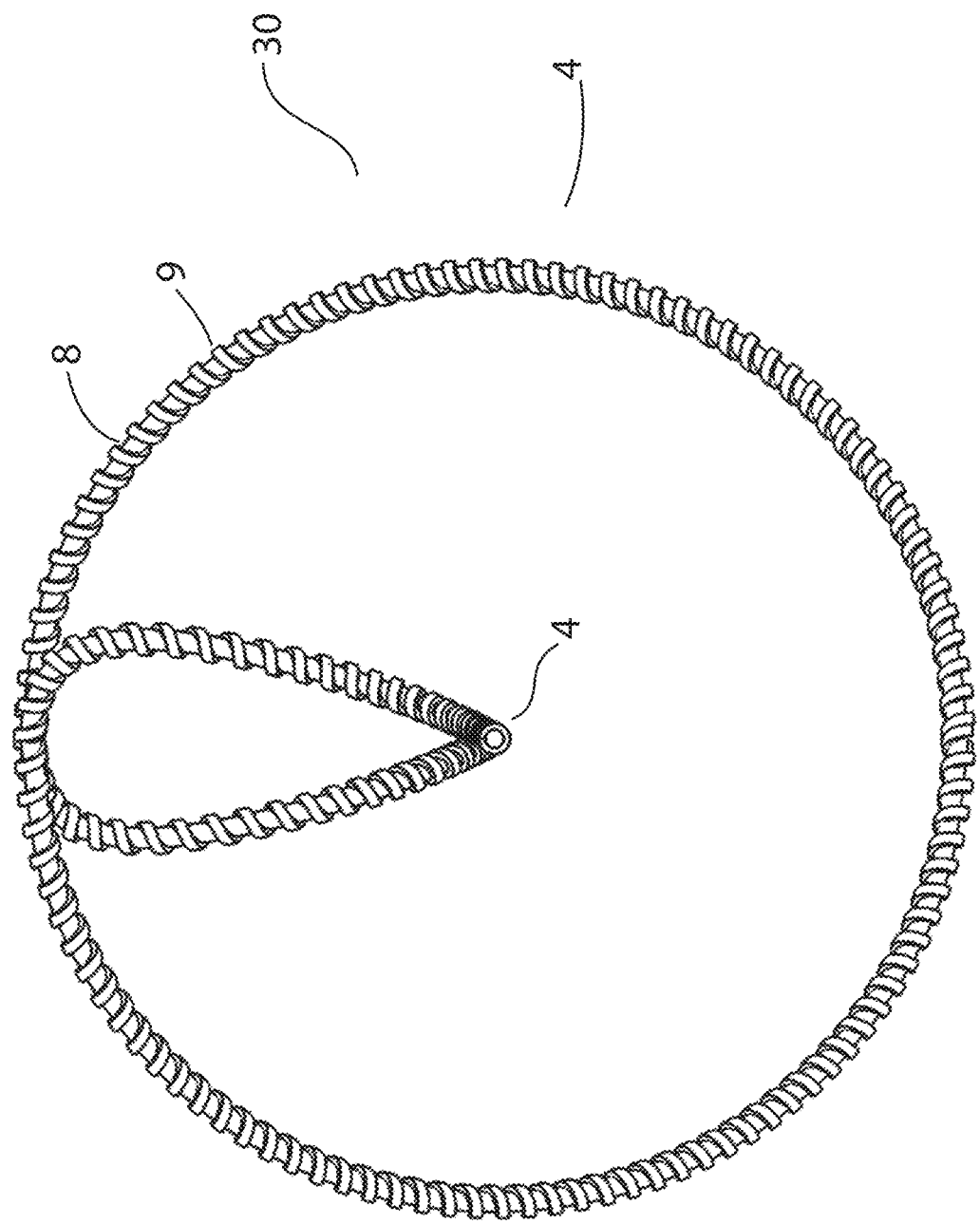
FIG. 21 is an end view of the device of FIG. 20.

The device is then moved proximally along the section of the vein to be treated (generally a segment of vein of about 10 to 70 cm), where the radial force of the abrasive surface of coil against the inner lumen of the vein, and the axial movement, causes the helical coil to remove, destroy or disrupt the superficial layers of the inside of the inner lumen of the vein. These layers consist of the glycocalyx, endothelium, sub endothelial connective tissue and superficial layers of the media layer. Stretch receptors in the vein wall respond to the devices outward radial force leading to vasospasm. This is further enhanced by release of chemical agents stored within endothelial cell bodies, mainly endothelin-1, a powerful vasoconstrictor. Exposure of subendothelial collagen leads to platelet adhesion and triggers a cascade activation of prothrombotic factors leading to thrombotic occlusion of the vessel. This thrombotic occlusion is further enhanced by significant vasospasm as shown in FIG. 19 where the treated vein section is significantly contracted in the acute stage. This results in a complete termination of blood flow in the vessel. This was demonstrated during a pre-clinical study on a goat lateral saphenous vein in which high pressure manual injection of contrast material did not enter the vein 45 minutes post treatment.

Not to be limited by theory, circumferential endothelial layer destruction allows intraluminal thrombosis to adhere directly to the vessel wall and causes recruitment of cells involved in the inflammatory healing response to migrate from the adventitia across the lumen and into the thrombus. These cells include fibroblasts which create collagen in the thrombotic occlusion converting the vessel into a fibrotic cord over time. This leads to long-term closure of the vessel and resolution of venous disease symptoms.

Contrary to the previous belief that complete vein wall transmural cell damage is required, the inventors have demonstrated that superficial denudation alone can cause a sufficient inflammatory reaction to induce fibroblasts on the outer adventitia layer to migrate inwards. This is advantageous as it provides a mechanism of action that a device can utilise which doesn't cause the patient pain or require tumescent needle stick preparation injections to prevent pain. This is because the sensory pain nerve fibres are located on the adventitial layer of the vessel which is not directly affected by the device.

Results from the authors pre-clinical studies have also proven the importance of full circumferential endothelial disruption in achieving long term successful occlusion. Thrombotic occlusion without endothelial disruption will lead to recanalisation even if the endothelium is partially disrupted as shown in FIG. 2. This is because the endothelium prevents thrombus adherence which causes thrombus shrinkage away from the vessel wall. This is further enhanced by nitric oxide secretion from the endothelial cells, promoting vasodilation thus counteracting the effect of venospasm. This may be the primary factor involved in the low efficacy rates of chemical sclerosant based techniques. As the sclerosant is deactivated by blood and removed by the velocity of circulation it can only cause incomplete endothelial disruption especially in larger vessels which have more blood and a greater surface area even in a collapsed state.

Figure 22:
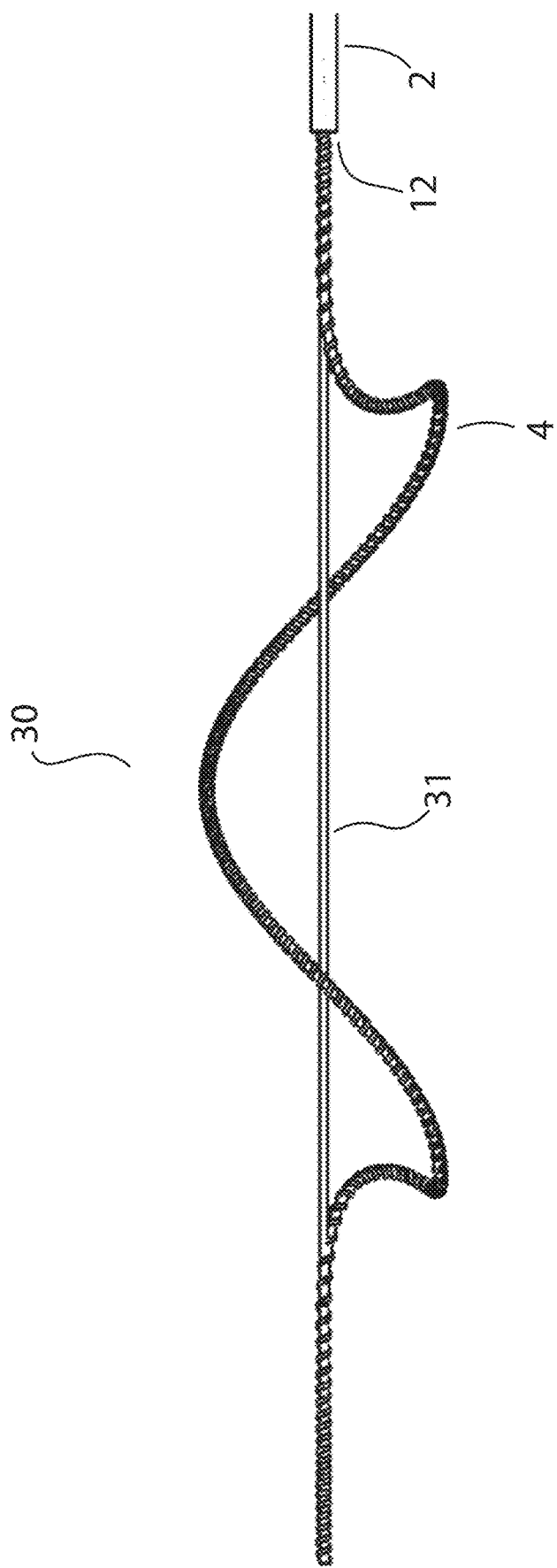
FIG. 22 is a side elevational view of the device of FIG. 20 in a partially deployed configuration.
Figure 23:
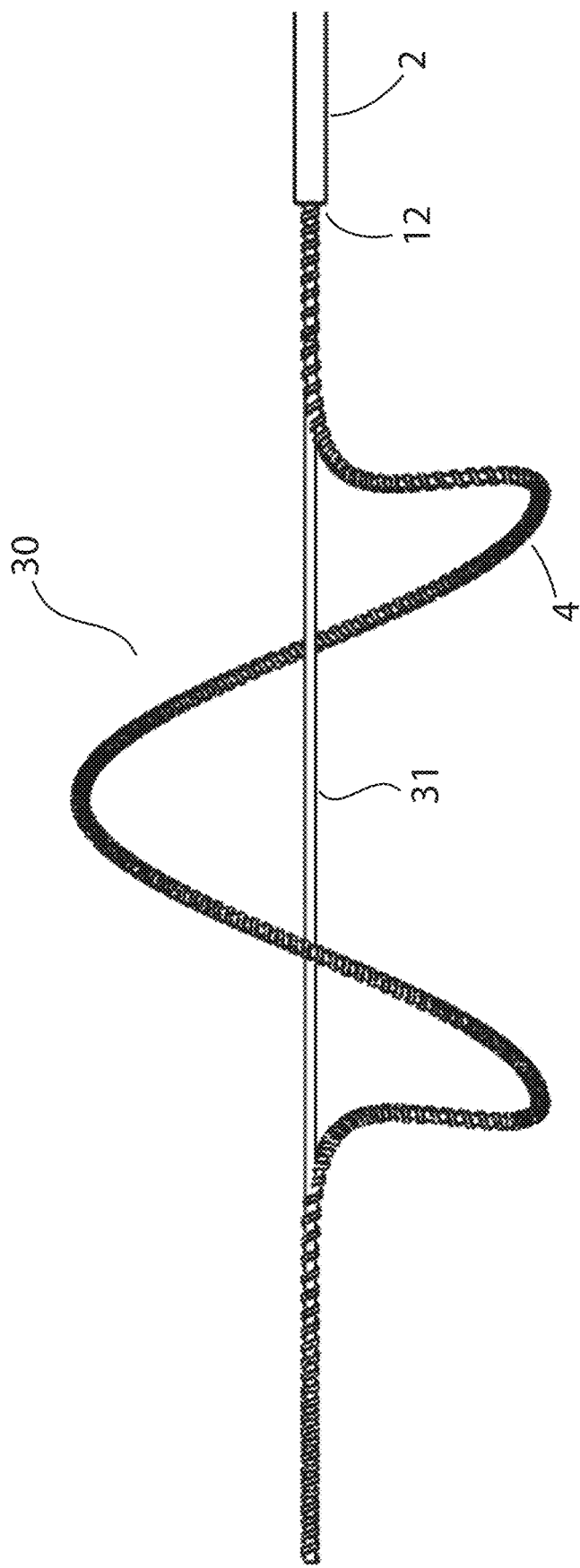
FIG. 23 is a side elevational view of the device of FIG. 20 in a fully deployed configuration.
Figure 24:
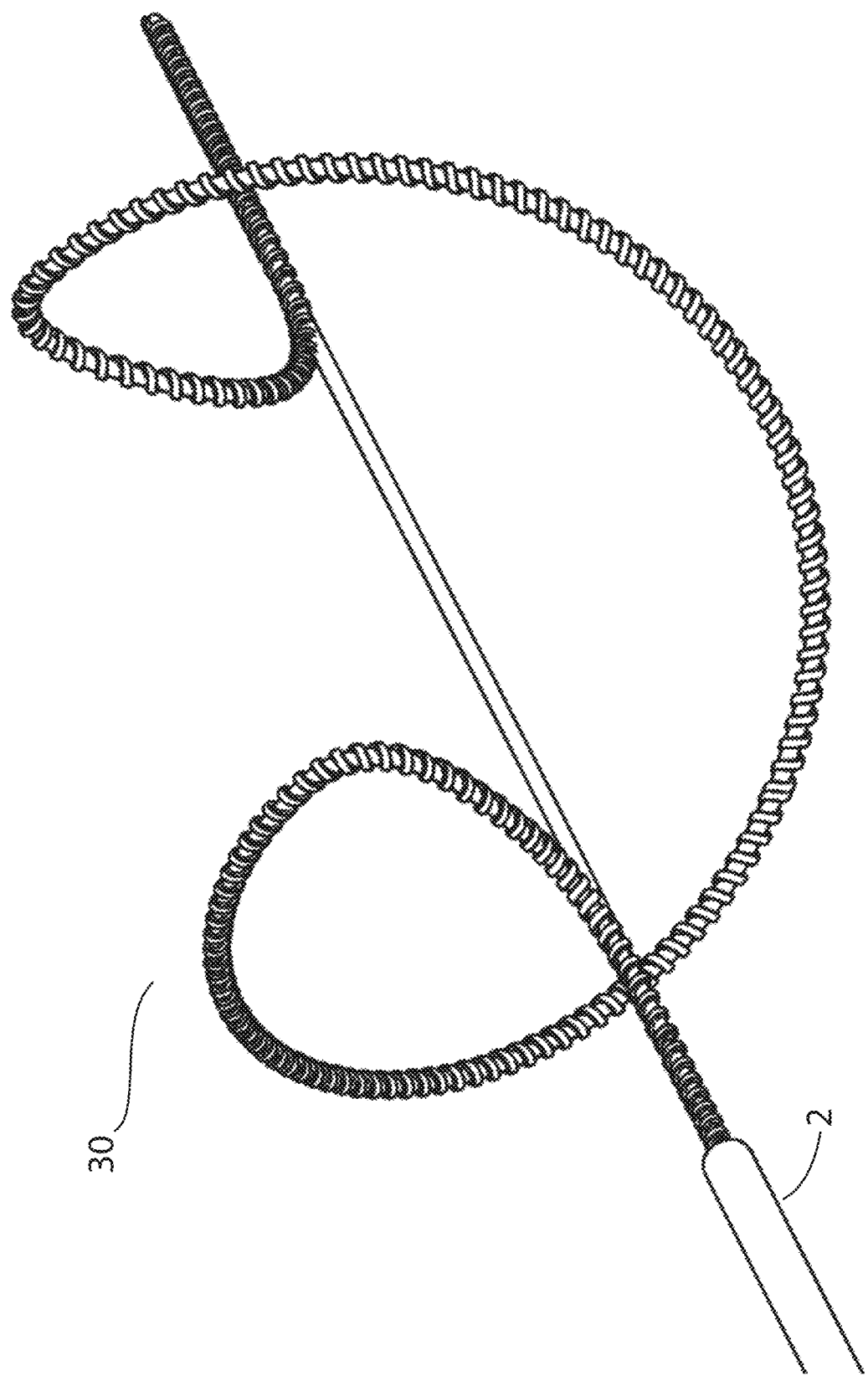
FIG. 24 is another side elevational view of the device of FIG. 20 in a fully deployed configuration.

The embodiments of FIGS. 4 to 16 all have a body lumen denuding head formed from a single coil element that in a deployed configuration comprises one full helical turn and in use circumferentially denudes an inner lumen of a body lumen. Referring to FIGS. 20 to 24, an alternative embodiment of the device of the present disclosure is described, indicated generally by the reference numeral 30, and in which parts described with reference to the previous embodiments are assigned the same reference numerals. In this embodiment, the device includes an elongated control arm 31 that passes through the catheter member 2 and is operatively connected to a distal end 6 of the coil 4, and the proximal end 5 of the coil is attached to the stainless steel hypotube 12. Axial movement of the control arm 31 relative to the hypotube 12 effects deployment or uncoiling of the coil—FIG. 22 shows the coil is a partly coiled configuration, and 23 shows the coil is a fully coiled configuration. The use of this embodiment is substantially the same as that described previously, with the exception that the deployment of the coil can be controlled by adjusting the axial position of the control arm 31 and hypotube 12.

Figure 25:
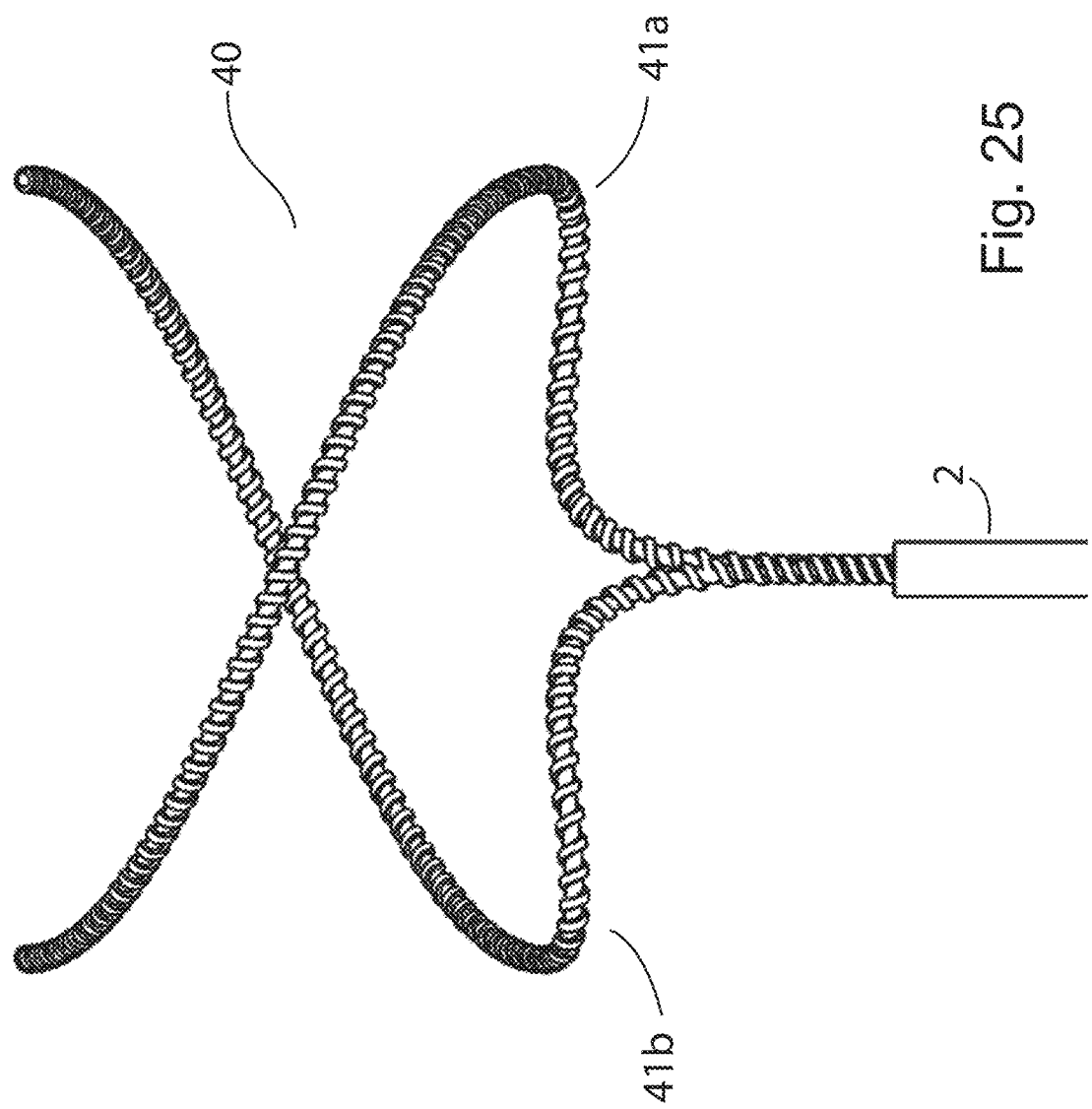
FIG. 25 illustrates a device for denuding a body lumen according to a further embodiment of the disclosure, in which the coil is made up of two co-axial helical coil elements.
Figure 26:
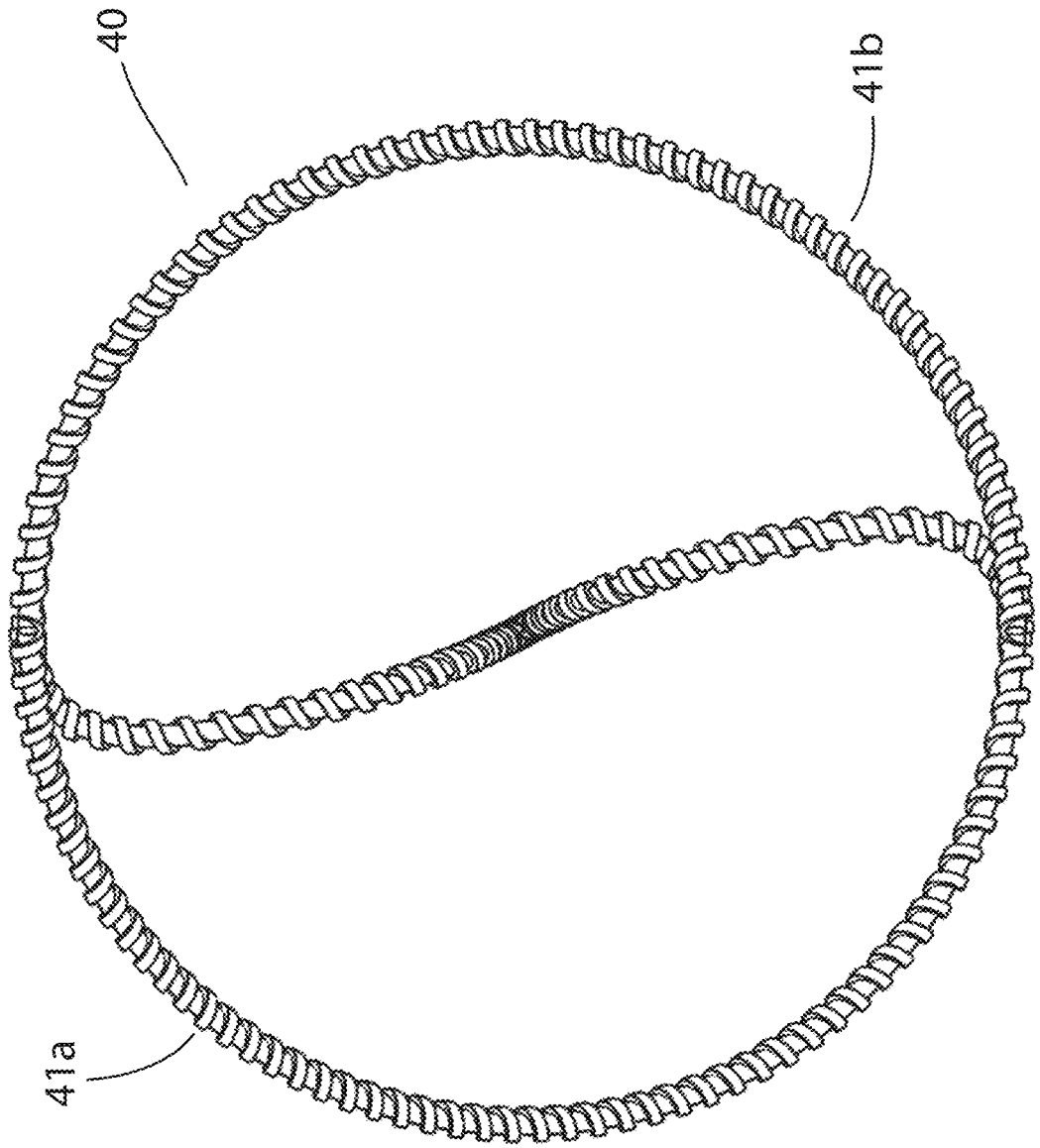
FIG. 26 is an end view of the device of FIG. 25.
Figure 27:
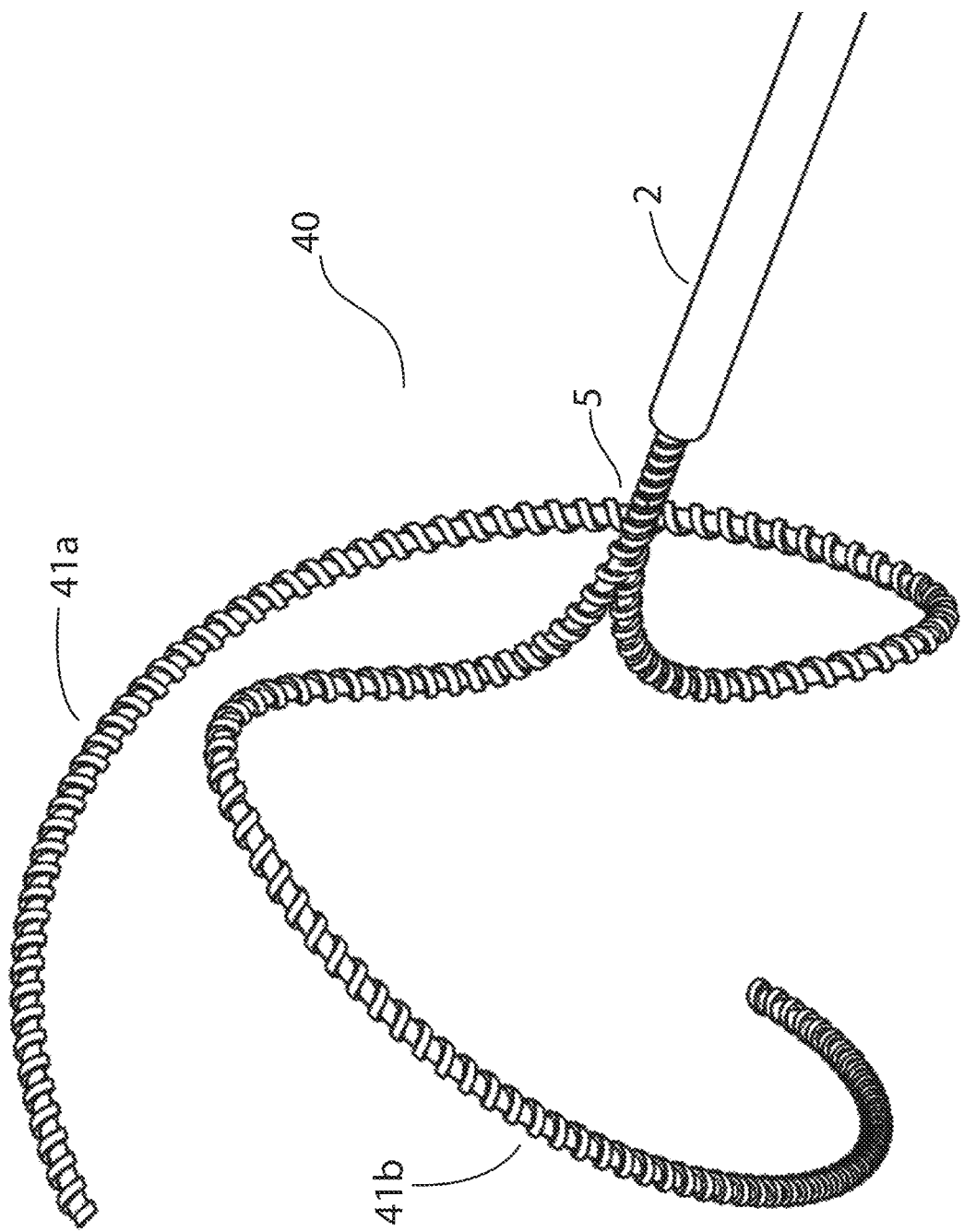
FIG. 27 is a side elevational view of the device of FIG. 25.

Referring to FIGS. 25 to 27, an alternative embodiment of the device of the present disclosure is described, indicated generally by the reference numeral 40, and in which parts described with reference to the previous embodiments are assigned the same reference numerals. In this embodiment, the coil 4 is composed of two coil elements 41*a* and 41*b* that work in tandem to circumferentially denude an inner lumen of the body lumen, each of which is adjustable from an uncoiled configuration suitable for disposal within the catheter member and transluminal delivery through a body lumen, and coiled configuration shown in the Figures. Each coil element 41*a*, 41*b* has a proximal part that is generally coaxial with the catheter member, and a coiled part that in its deployed configuration comprises less than one full turn such the coil elements together adapt a double helix conformation that in use circumferentially engages the body lumen to be treated. As with previous embodiments, each coil element comprises a core wire 8 having a second wire 9 wrapped around the core wire to provide a serrated body lumen denuding surface. The use of this embodiment, is the same as that described with reference to the previous embodiments.

Figure 28:
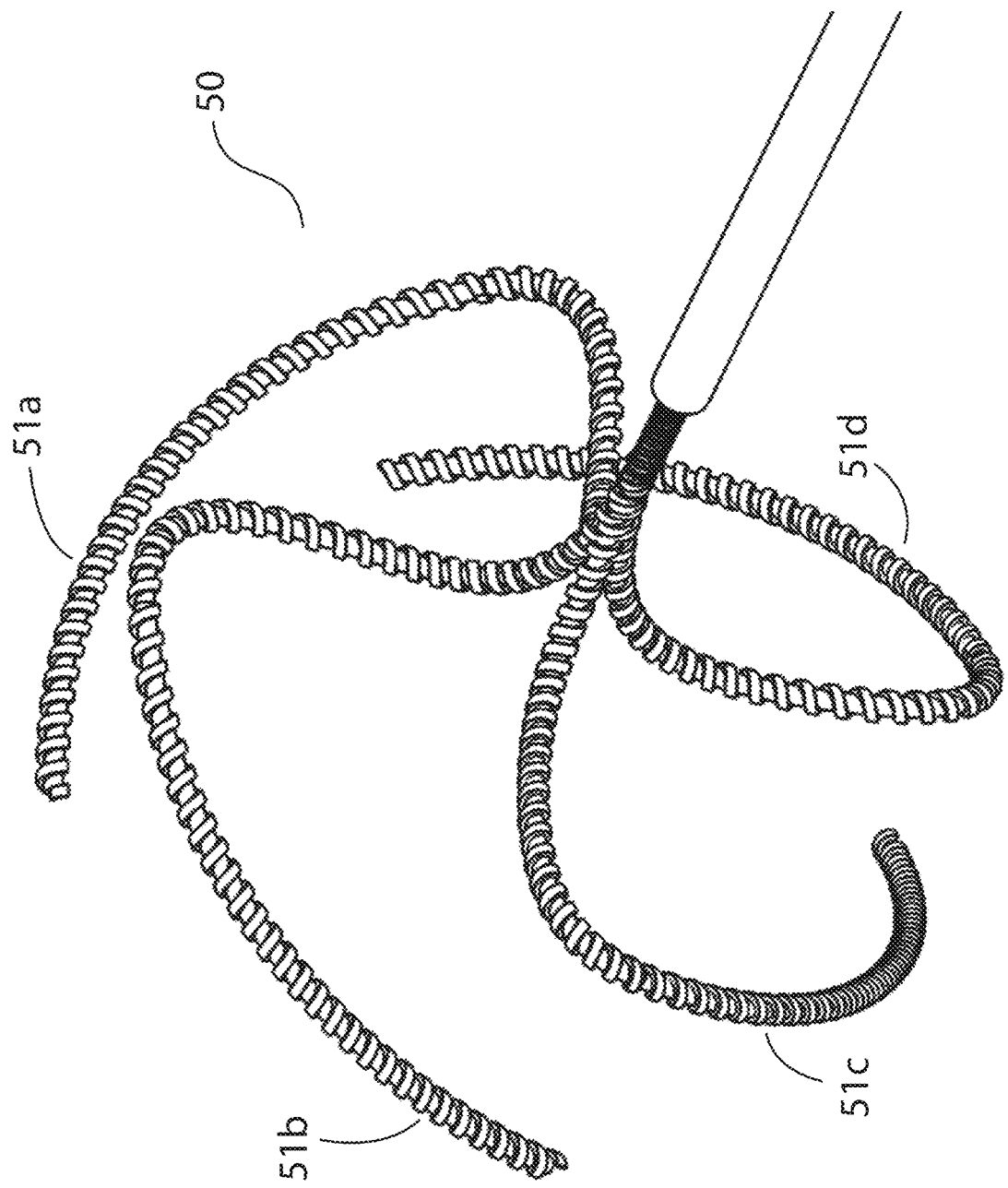
FIG. 28 illustrates a device for denuding a body lumen according to a further embodiment of the disclosure, in which the coil is made up of four co-axial helical coil elements.
Figure 29:
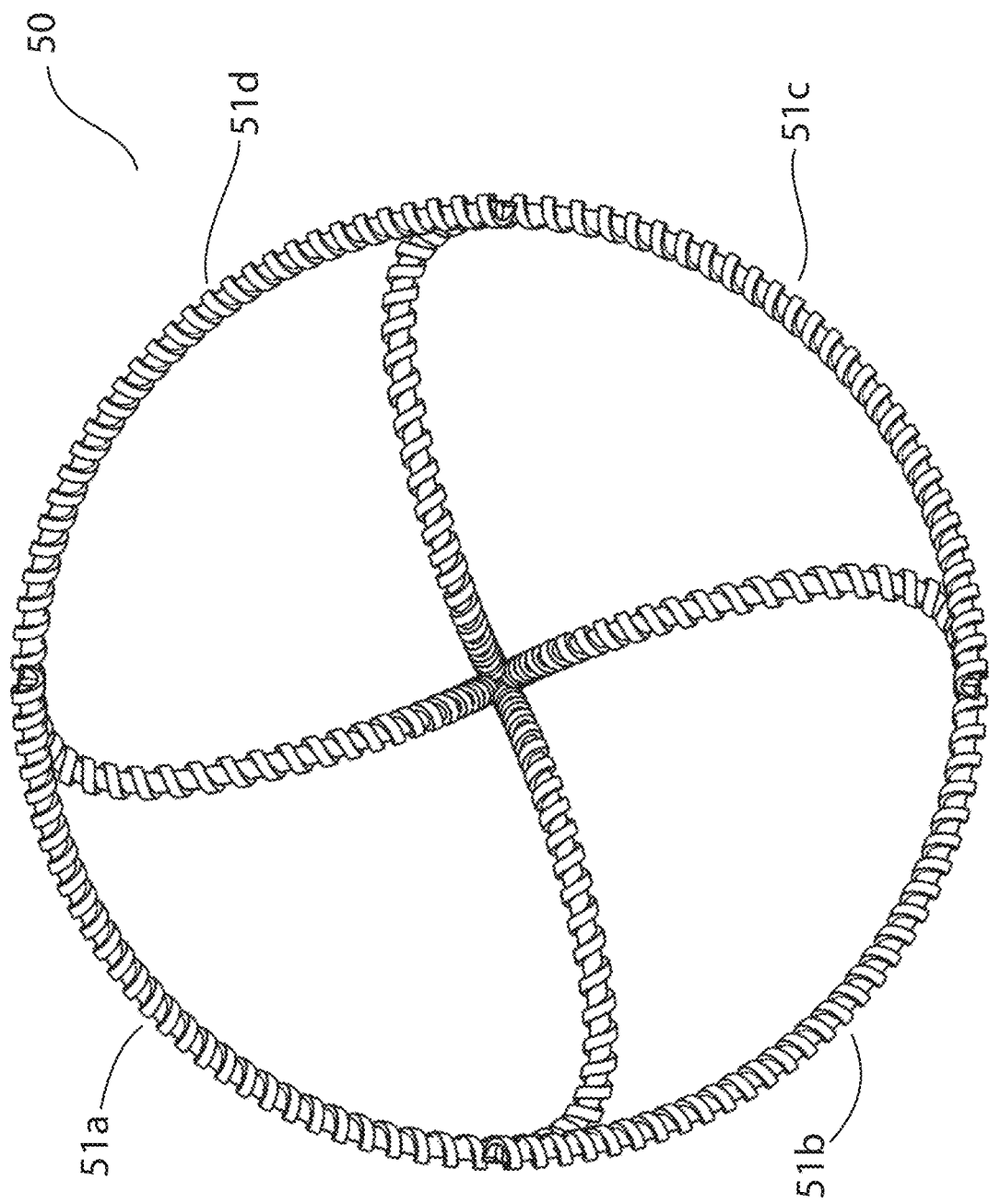
FIG. 29 is an end view of the device of FIG. 28.
Figure 30:
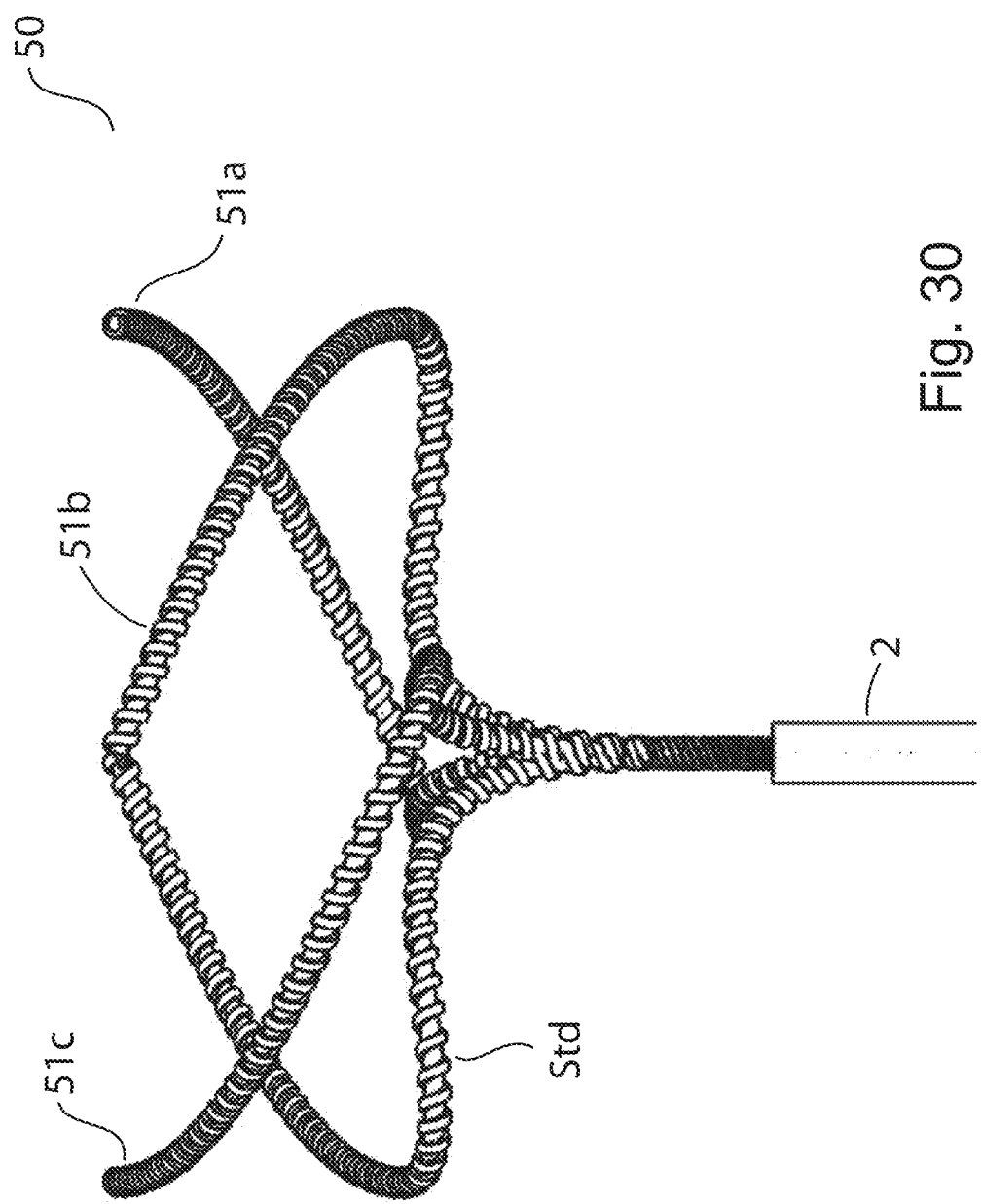
FIG. 30 is a side elevational view of the device of FIG. 28.

Referring to FIGS. 28 to 30, an alternative embodiment of the device of the present disclosure is described, indicated generally by the reference numeral 50, and in which parts described with reference to the previous embodiments are assigned the same reference numerals. In this embodiment, the coil 4 is composed of four coil elements 51*a*-51*d* that work in tandem to circumferentially denude an inner lumen of the body lumen, each of which is adjustable from an uncoiled configuration suitable for disposal within the catheter member and transluminal delivery through a body lumen, and coiled configuration shown in the Figures. Each coil element 51*a* to 51*d* in its deployed configuration comprises about one quarter of a full turn and the four coil elements together adapt a quadruple helix conformation, such that the four coil elements together circumferentially engage the body lumen to be treated. As with previous embodiments, each coil element comprises a core wire 8 having a second wire 9 wrapped around the core wire to provide a serrated body lumen denuding surface. The use of this embodiment, is the as that described with reference to the previous embodiments.

Figure 31:
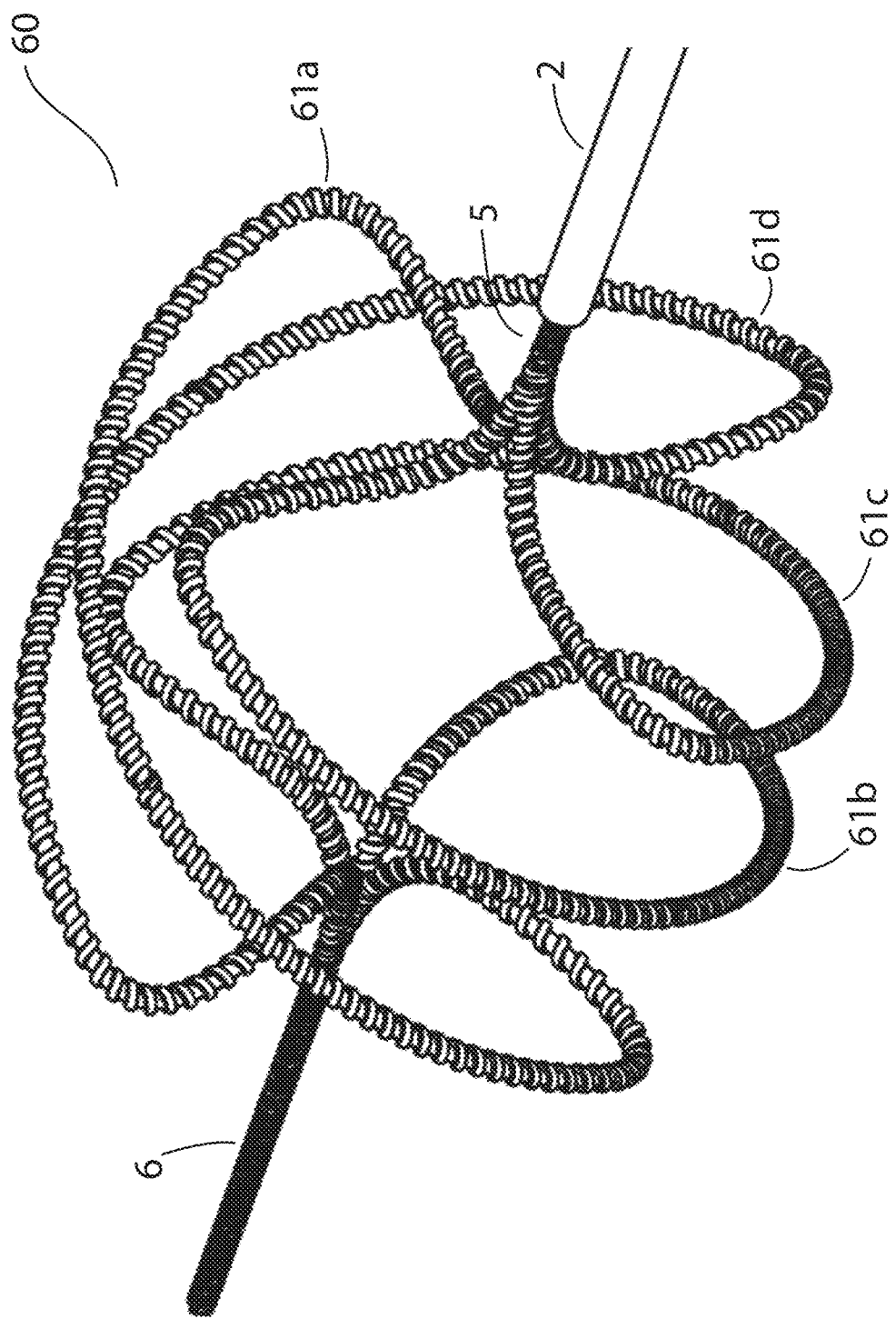
FIG. 31 illustrates a device for denuding a body lumen according to a further embodiment of the disclosure, in which the coil is made up of four co-axial helical coil elements which are joined at their distal ends.
Figure 32:
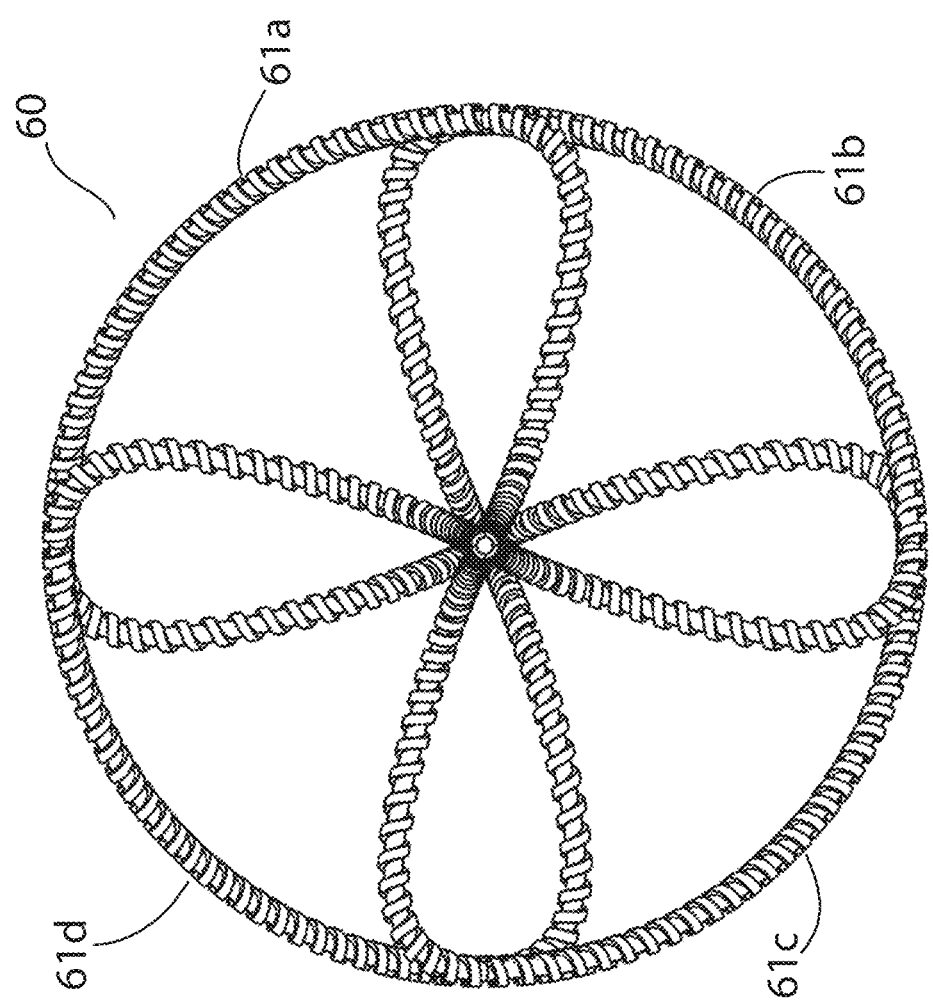
FIG. 32 is an end view of the device of FIG. 31.

In the embodiments described above that comprise more than one coil element, the coil elements are joined at their proximal ends and have free distal ends (i.e. open coils). It will be appreciated however that the coil may be a closed coil, where the coil elements are joined together at the proximal and distal ends. Such an embodiment is described in FIGS. 31-33, in which parts described with reference to the previous embodiments are assigned the same reference numerals. In this embodiment, the device 60 comprises a coil formed of four helical coil elements 61*a*-61*d* that are joined together at their proximal and distal ends 5, 6, with each coil having about one half of a full turn. As with previous embodiments, each coil element comprises a core wire 8 having a second wire 9 wrapped around the core wire to provide a serrated body lumen denuding surface. The use of this embodiment, is the as that described with reference to the previous embodiments.

FIGS. 34A to 41B illustrate helical coils forming part of devices of the present disclosure, and in particular different types of wires forming the coils, and different types of indentations/formations on a surface of the coil forming the roughened surface. The coils are formed from nitinol wire, and the indentations are cut using a knurling process.

Figure 34A:
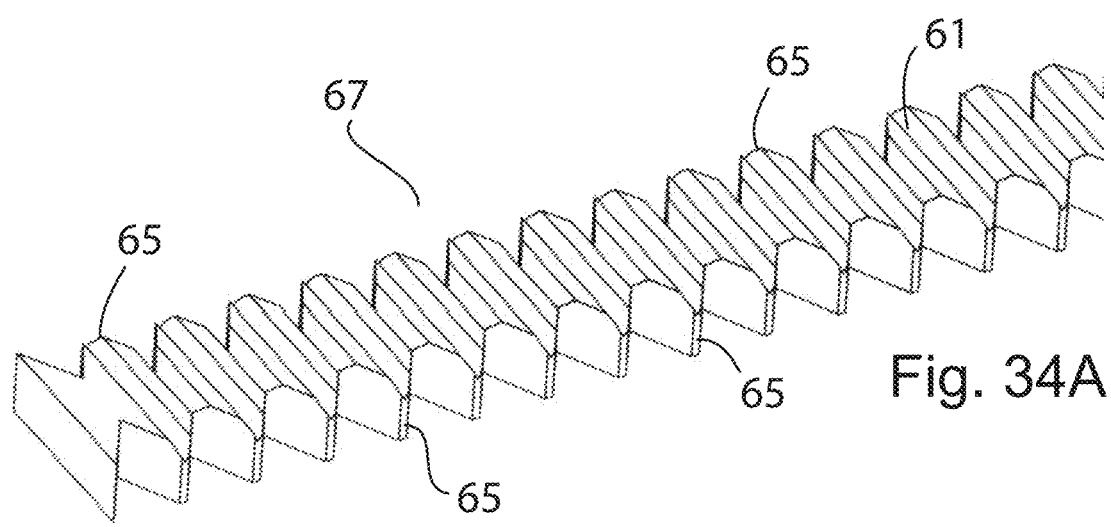
FIG. 34A and FIG. 34B are perspective and side elevational views of a section of a helical coil according to the disclosure.
Figure 34B:
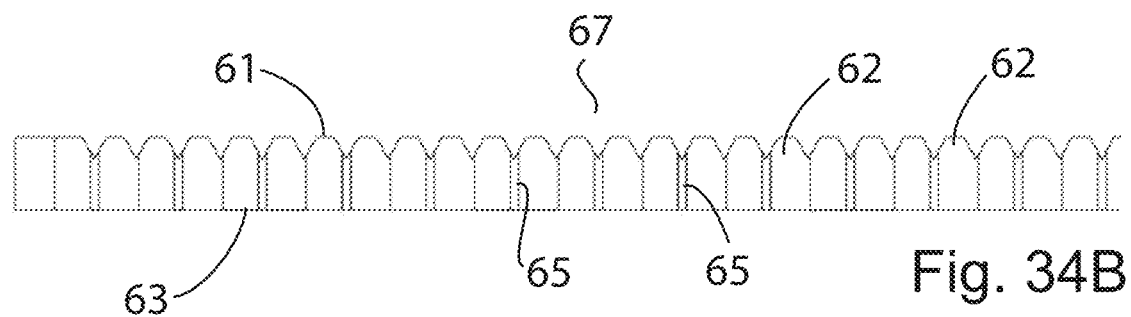

Referring to FIGS. 34A and 34B, a section of a helical coil 67 is illustrated having a generally flat profile with an external lumen-engaging surface 61 with transverse indentations forming teeth 62 having a truncated triangle profile, a flat internal surface 63, and sides cut in a zig-zag formation providing a multiplicity of lateral teeth 65.

Figure 35A:
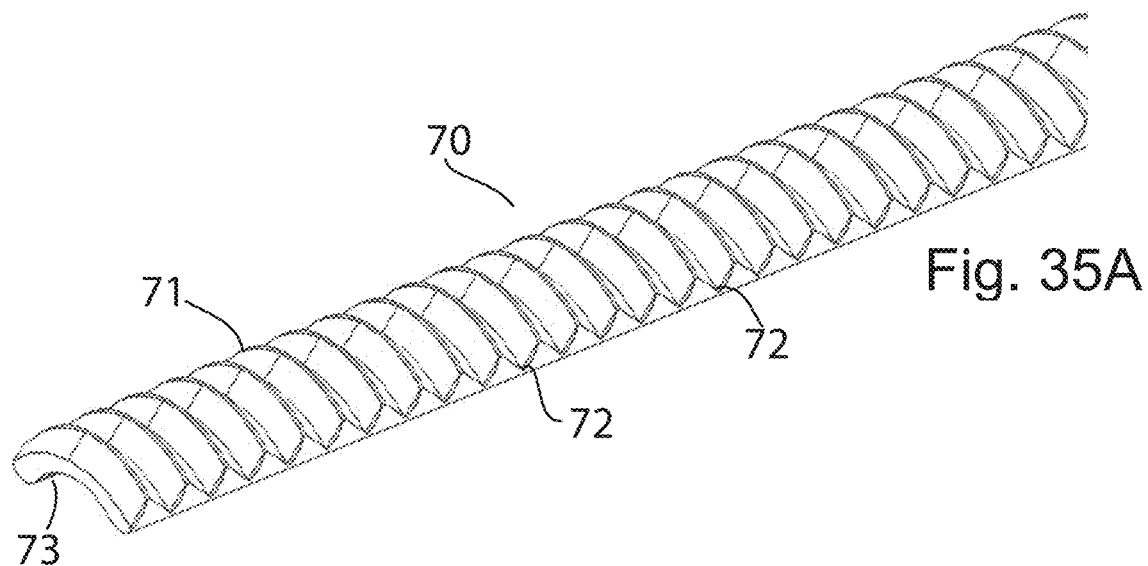
FIG. 35A and FIG. 35B are perspective and side elevational views of a section of a further helical coil according to the disclosure.
Figure 35B:
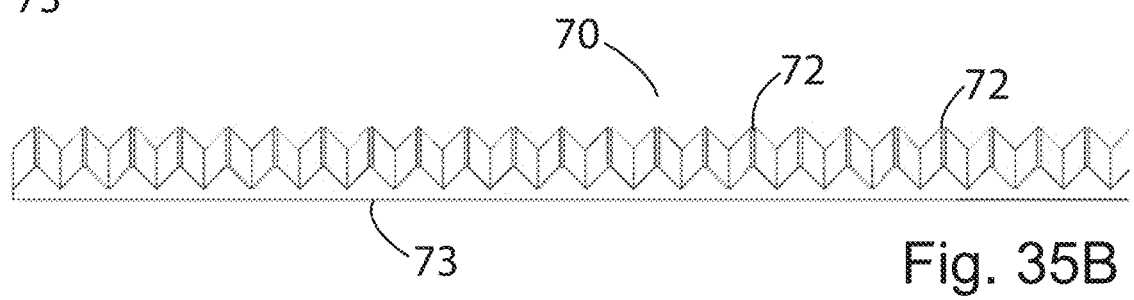

Referring to FIGS. 35A and 35B, a section of a helical coil 70 is illustrated having a generally convex profile with an external lumen-engaging surface 71 with curved transverse indentations forming teeth 72 having a triangular profile, and a smooth convex internal surface 73.

Figure 36A:
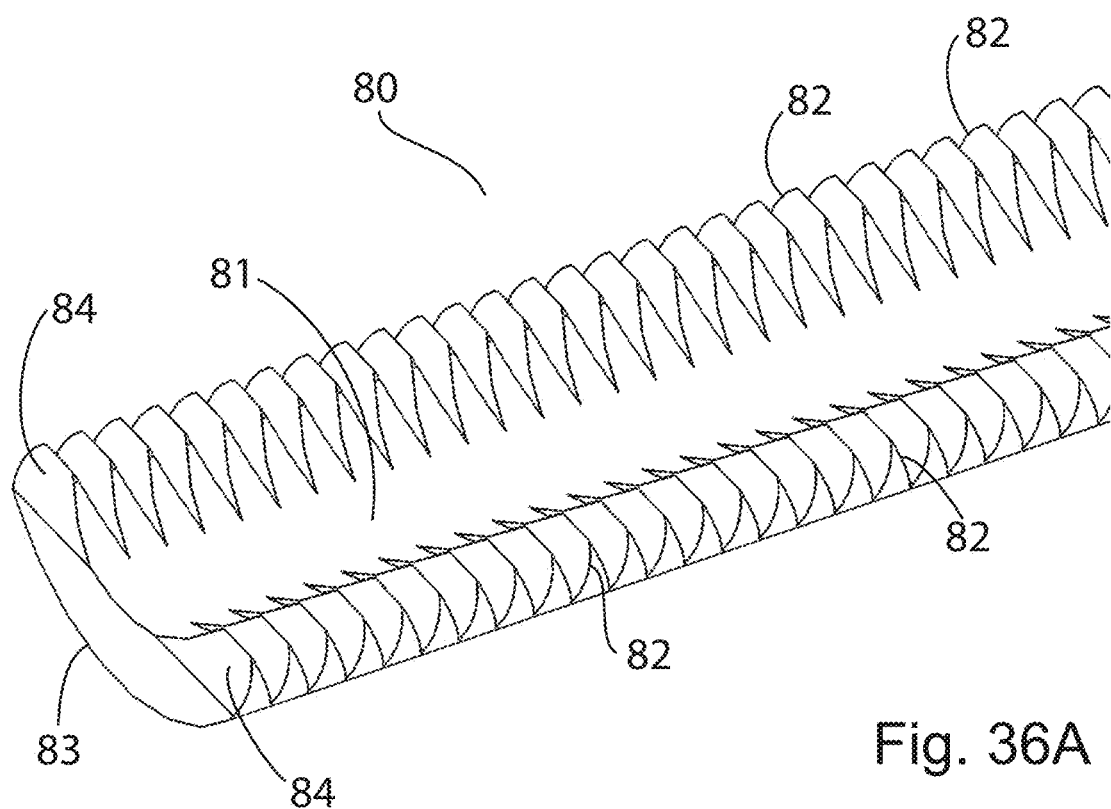
FIG. 36A and FIG. 36B are perspective and side elevational views of a section of a further helical coil according to the disclosure.
Figure 36B:
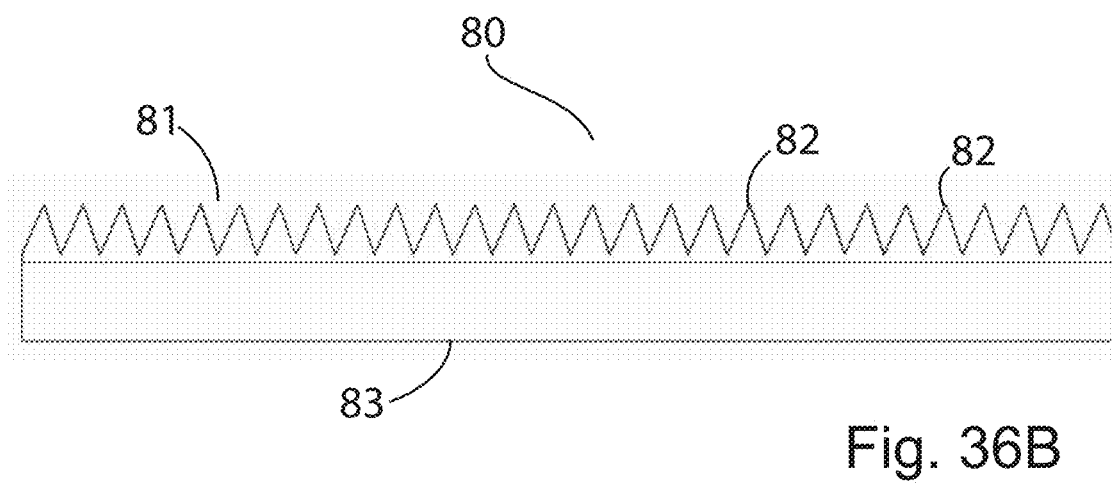

Referring to FIGS. 36A and 36B, a section of a helical coil 80 is illustrated having a generally flat profile with an external lumen-engaging surface 81 with transverse indentations formed on each side 84 of the surface 81 providing two series of teeth 82 having a truncated triangle profile, and a smooth concave internal surface 83.

Referring to FIGS. 37A and 37B, a section of a helical coil 90 is illustrated having a generally convex profile with a convex external lumen-engaging surface 91 with indentations formed on the surface 91 providing diamond-shaped teeth 92 some with flat tips and some with pointed tips, and a smooth flat internal surface 93.

Referring to FIGS. 38A and 38B, a section of a helical coil 100 is illustrated having a generally crescent-shaped profile with a convex external lumen-engaging surface 101 with curved indentations formed on the surface 101 providing transverse teeth 102 having a scalene triangular profile, and a smooth flat internal surface 103.

Figure 39A:
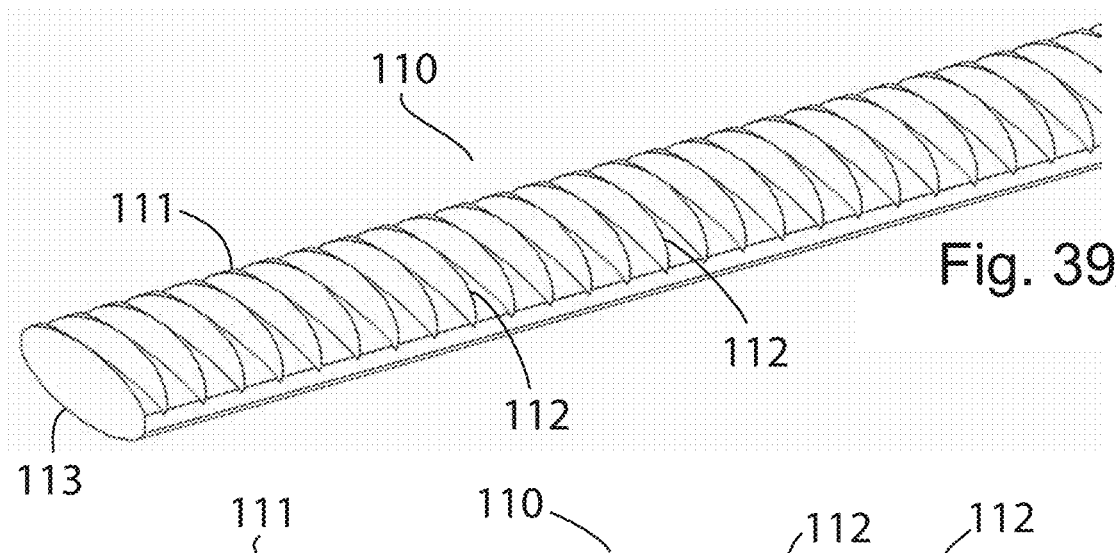
FIG. 39A and FIG. 39B are perspective and side elevational views of a section of a further helical coil according to the disclosure.
Figure 39B:
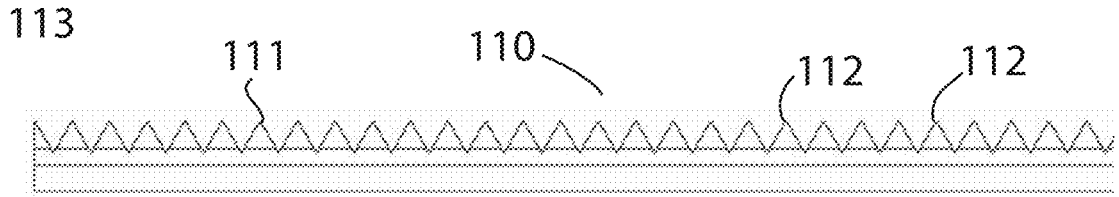

Referring to FIGS. 39A and 39B, a section of a helical coil 110 is illustrated having a generally oval-shaped profile with a convex external lumen-engaging surface 111 with curved V-profile indentations formed on the surface 111 providing transverse teeth 102 having a triangular profile, and a smooth flat internal surface 113.

Figure 40A:
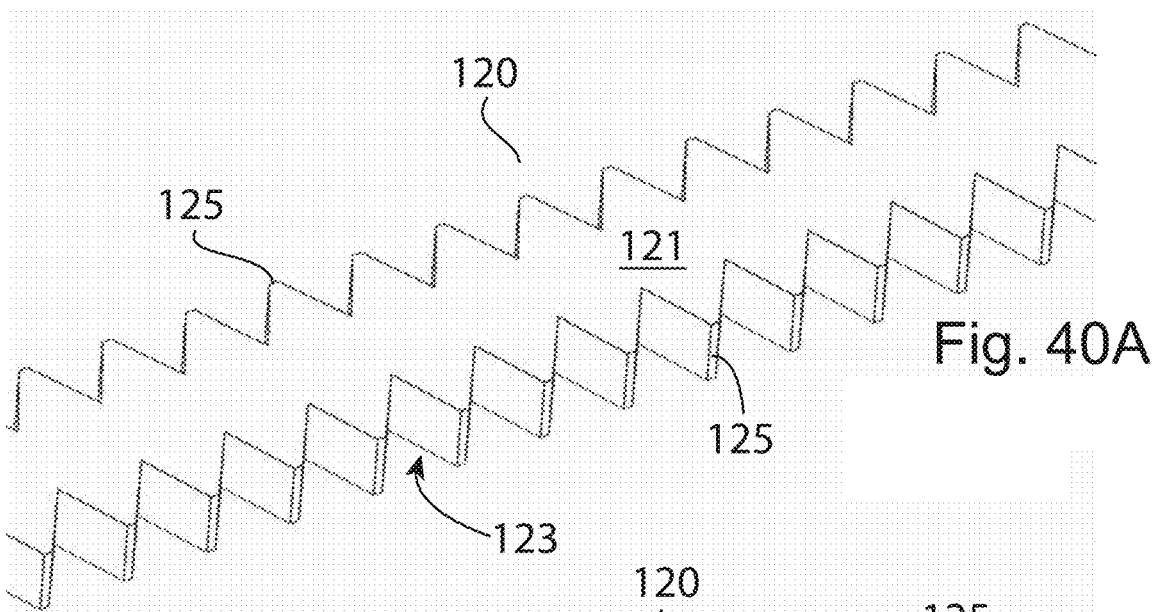
FIG. 40A and FIG. 40B are perspective and side elevational views of a section of a further helical coil according to the disclosure.
Figure 40B:
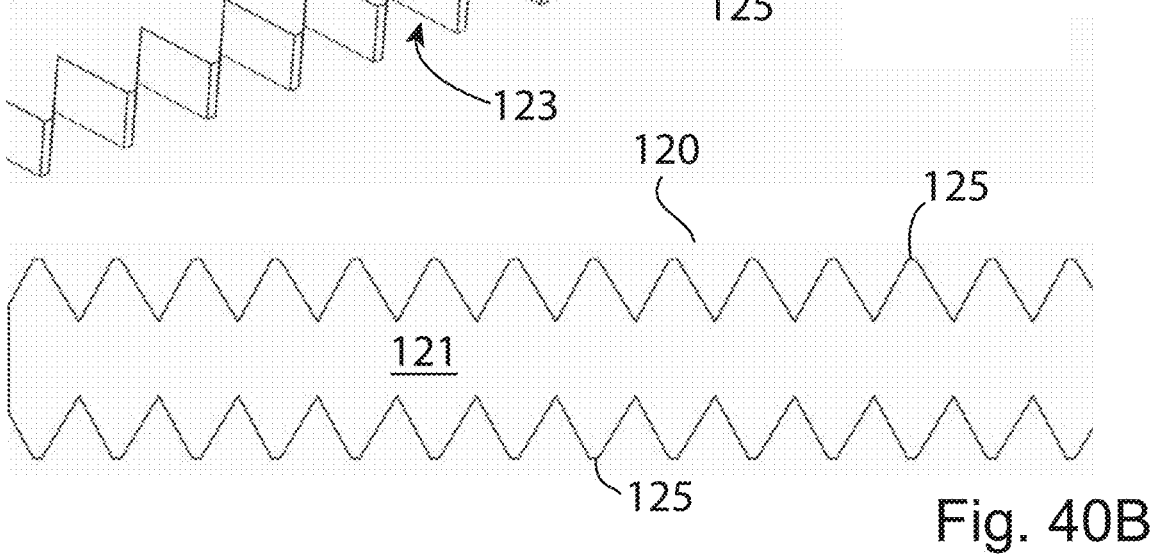

Referring to FIGS. 40A and 40B, a section of a helical coil 120 is illustrated having a generally flat profile with a flat external lumen-engaging surface 121, a flat internal surface 123, and sides cut in a zig-zag formation providing a multiplicity of lateral teeth 125.

Figure 41A:
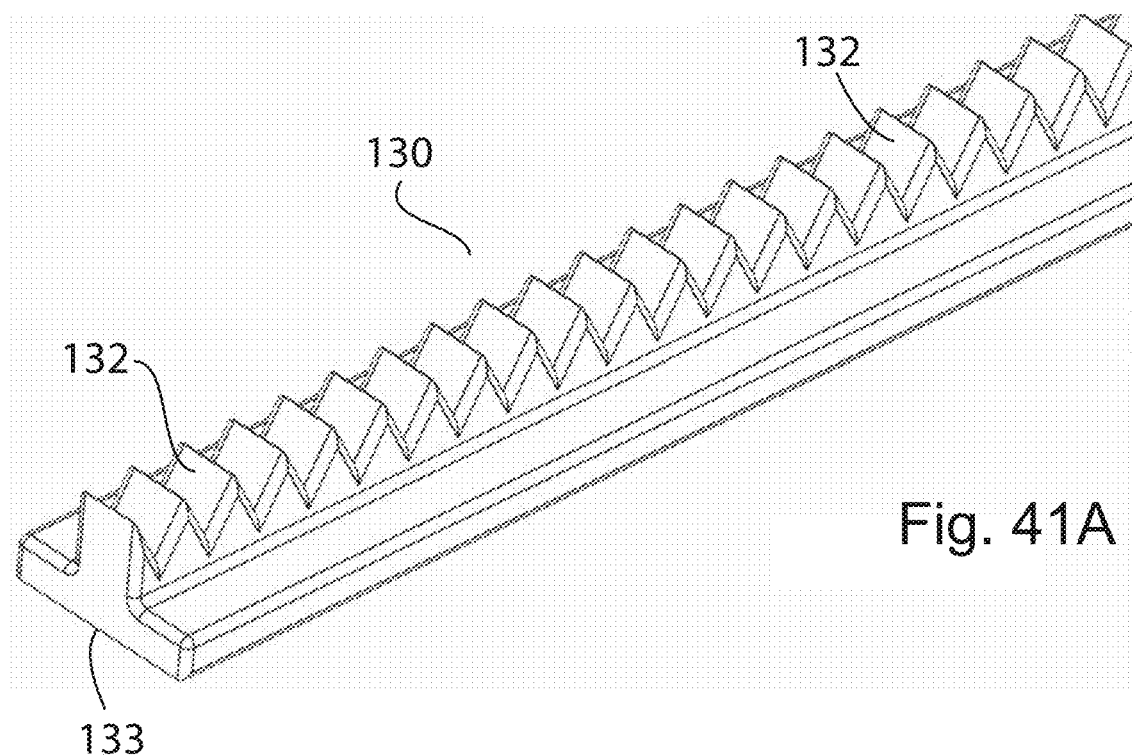
FIG. 41A and FIG. 41B are perspective and end elevational views of a section of a further helical coil according to the disclosure.
Figure 41B:
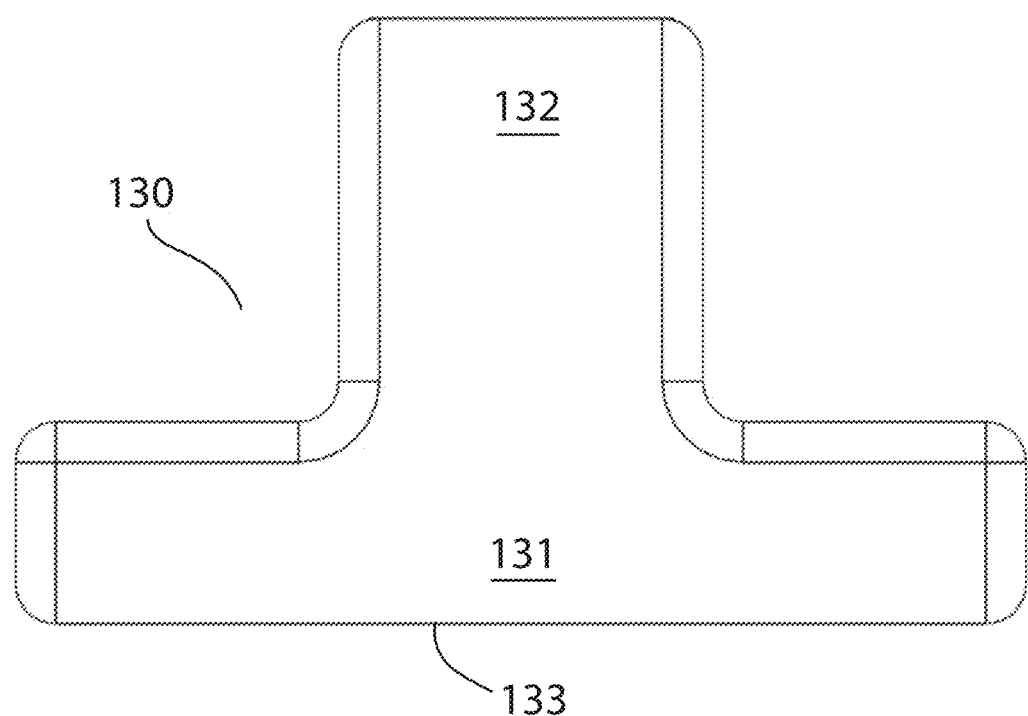

Referring to FIGS. 41A and 41B, a section of a helical coil 130 is illustrated having a generally inverted T-shaped profile with a base 131, teeth 132 disposed on the base, and a smooth flat internal surface 133.

The above described surface patterns and shapes are advantageous as they allow both the correct angle, depth, and level of cellular disruption to be delivered during axial treatment of the body lumen wherein the deployed device is automatically deformed in response to changes in the body lumen diameter. As previously described the macro-abrasive surface should ideally contact the vessel wall perpendicularly during withdrawal to have the greatest effect.

FIGS. 42A to 48C illustrate a number of vein denuding heads forming part of devices of the present disclosure, and in particular vein denuding heads having a single helical coil, and in which parts described with reference to previous embodiments are assigned the same reference numerals.

Figure 42A:
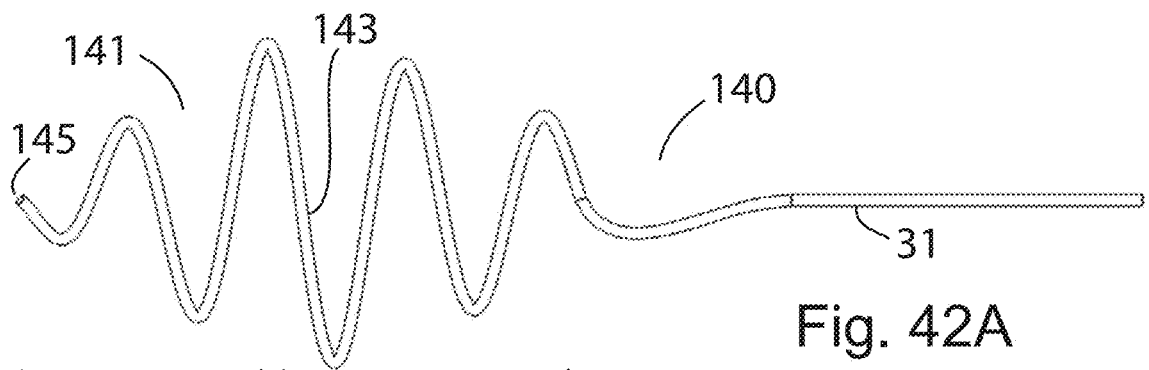
FIG. 42A and FIG. 42B are side elevational and perspective views of a further embodiment of a helical coil forming part of device according to the disclosure.
Figure 42B:
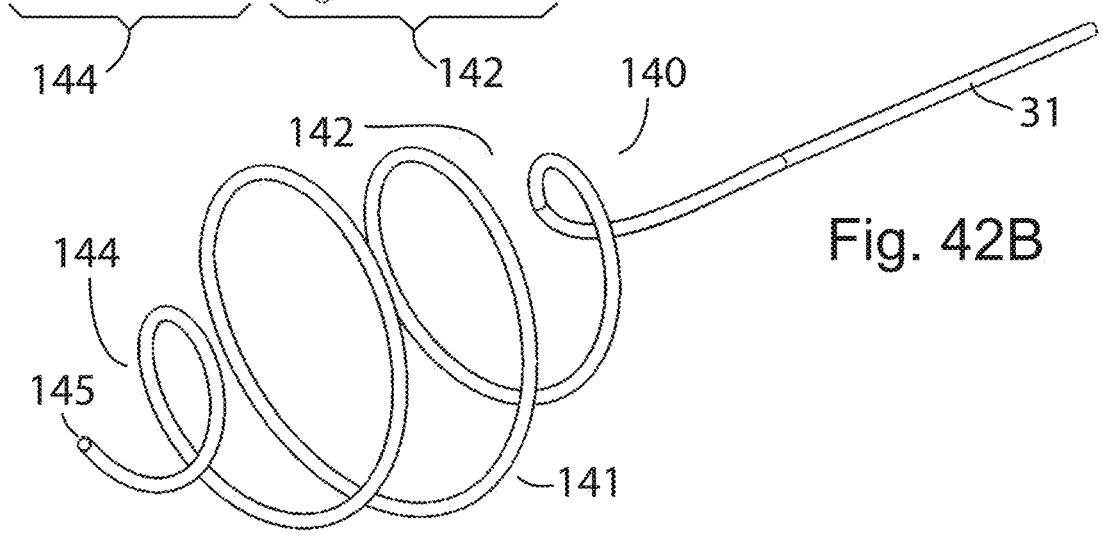

FIGS. 42A and 42B illustrate a vein denuding head forming part of a device of the present disclosure, and indicated generally by the reference numeral 140, and comprising a control arm 31 and helical coil 141 having approximately three turns and a proximal section 142 where the coil increases in diameter towards a mid-point 143 and a distal section 144 where the diameter of the coil decreases in diameter towards a distal tip 145 which is disposed on an axis of the helical coil.

Figure 43A:
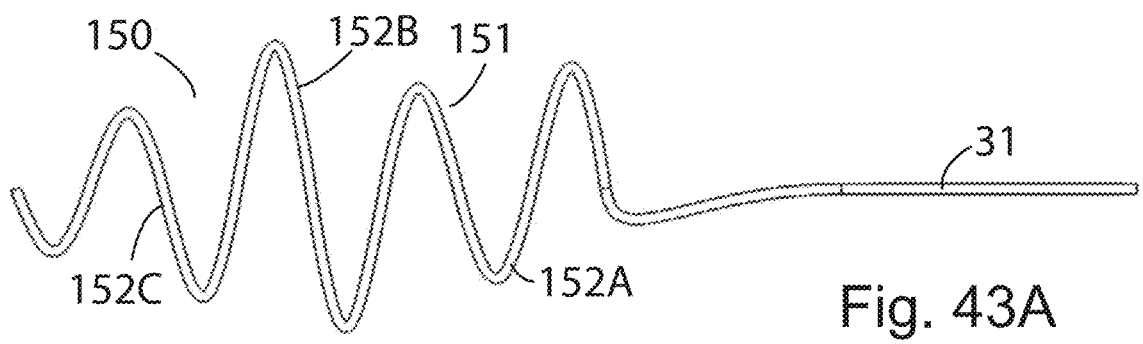
FIG. 43A and FIG. 43B are side elevational and perspective views of a further embodiment of a helical coil forming part of device according to the disclosure.
Figure 43B:
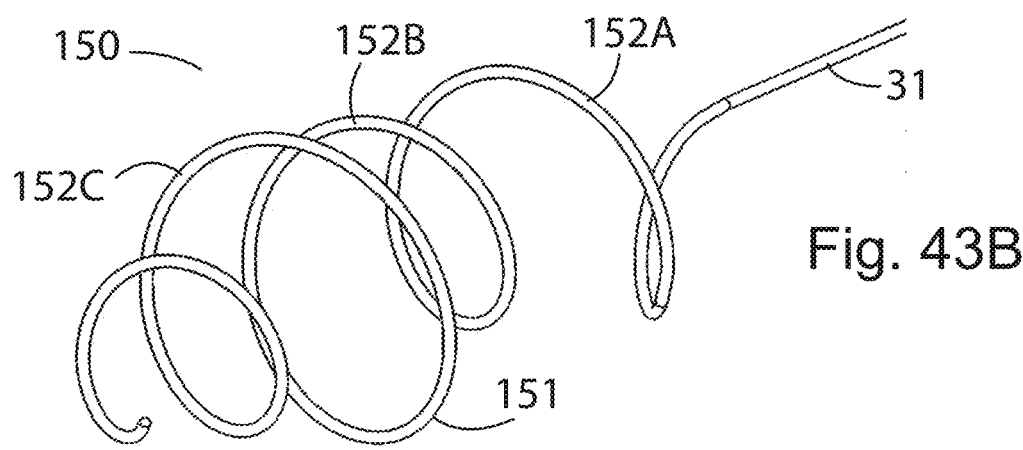

FIGS. 43A and 43B illustrate a vein denuding head forming part of a device of the present disclosure, and indicated generally by the reference numeral 150, and comprising a control arm 31 and helical coil 151 having approximately three turns (coils) 152A, 152B, 152C each of which has a slightly different diameter and is slightly offset, axially, relative to the preceding turn.

Figure 44A:
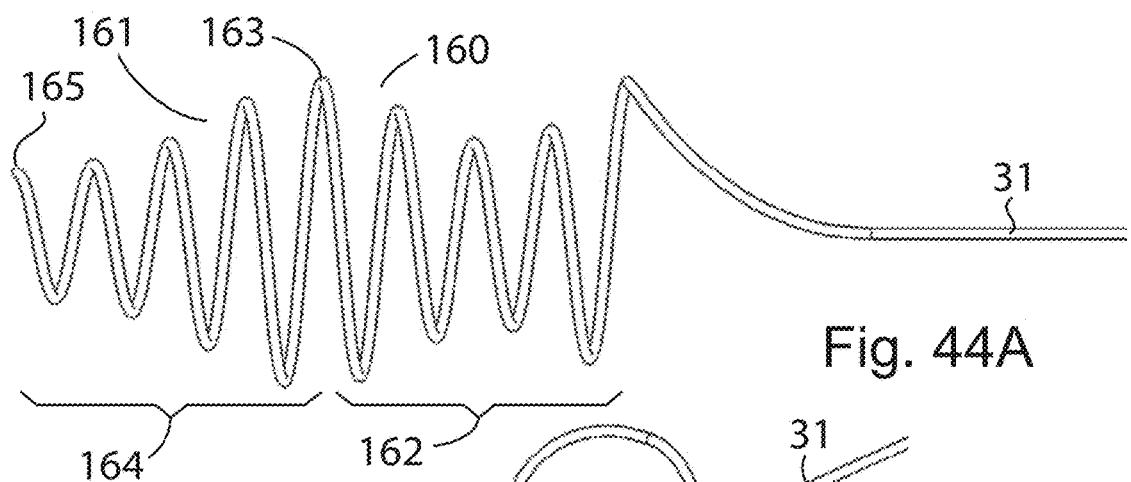
FIG. 44A and FIG. 44B are side elevational and perspective views of a further embodiment of a helical coil forming part of device according to the disclosure.
Figure 44B:
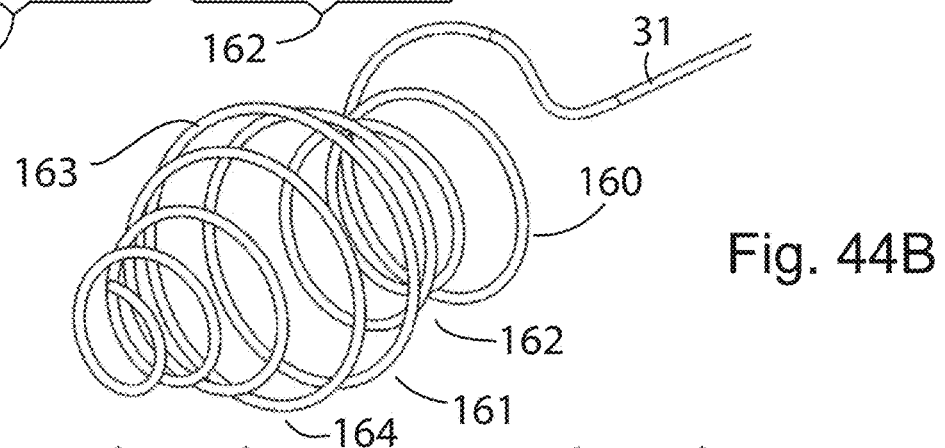

FIGS. 44A and 44B illustrate a vein denuding head forming part of a device of the present disclosure, and indicated generally by the reference numeral 160, and comprising a control arm 31 and helical coil 161 having approximately seven turns (coils) with varying diameter and including a proximal section 162 where the coil initially decreases and then increases in diameter towards a mid-point 163 and a distal section 164 where the diameter of the coil decreases in diameter towards a distal tip 165.

Figure 45A:
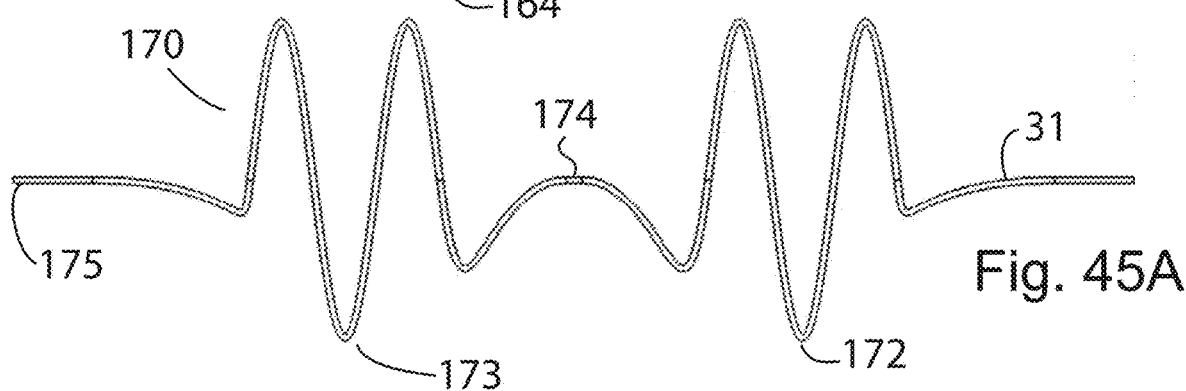
FIG. 45A and FIG. 45B are side elevational and perspective views of a further embodiment of a helical coil forming part of device according to the disclosure.
Figure 45B:
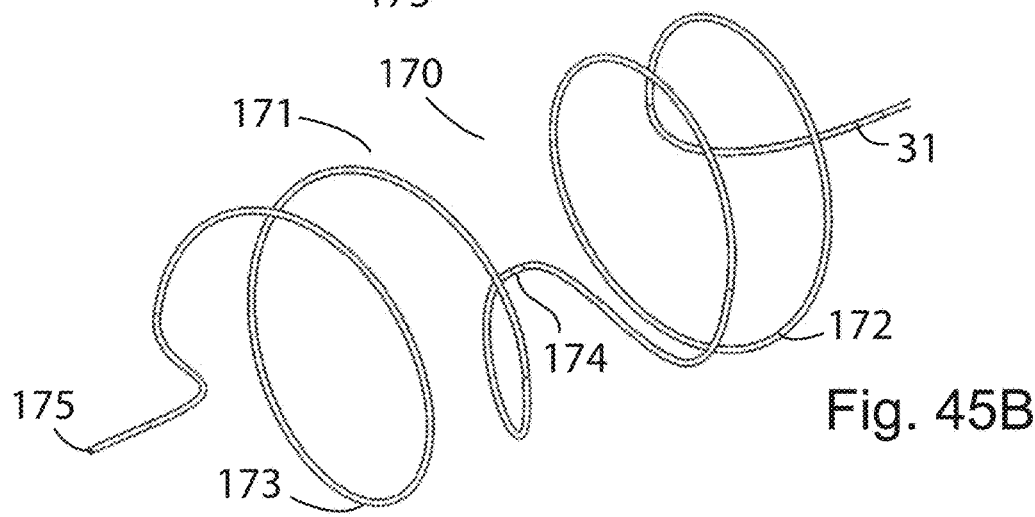

FIGS. 45A and 45B illustrate a vein denuding head forming part of a device of the present disclosure, and indicated generally by the reference numeral 170, and comprising a control arm 31 and helical coil 171 having approximately four turns (coils) and comprising a proximal coil element 172, distal coil element 173, and transition member 174 connecting the coil elements, and a distal tip 175.

Figure 46A:
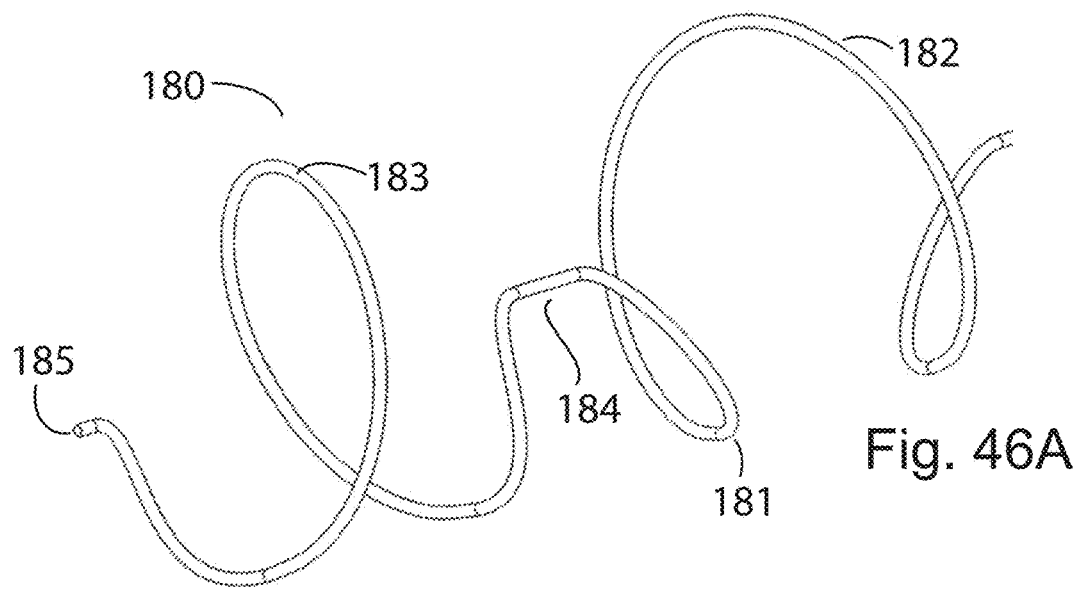
FIG. 46A and FIG. 46B are perspective and side elevational views of a further embodiment of a helical coil forming part of device according to the disclosure.
Figure 46B:
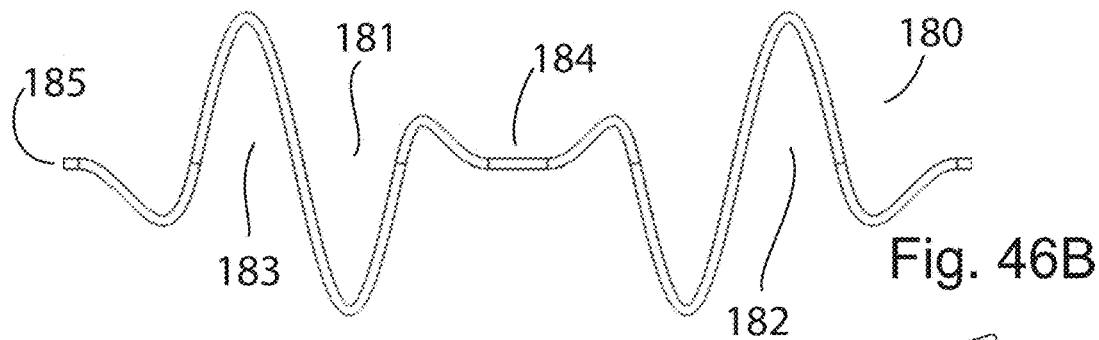

FIGS. 46A and 46B illustrate a vein denuding head forming part of a device of the present disclosure, and indicated generally by the reference numeral 180, and comprising a helical coil 181 having approximately two turns (coils) and comprising a proximal coil element 182, distal coil element 183, and transition member 184 including a straight section connecting the coil elements, and a distal tip 185.

Figure 47A:
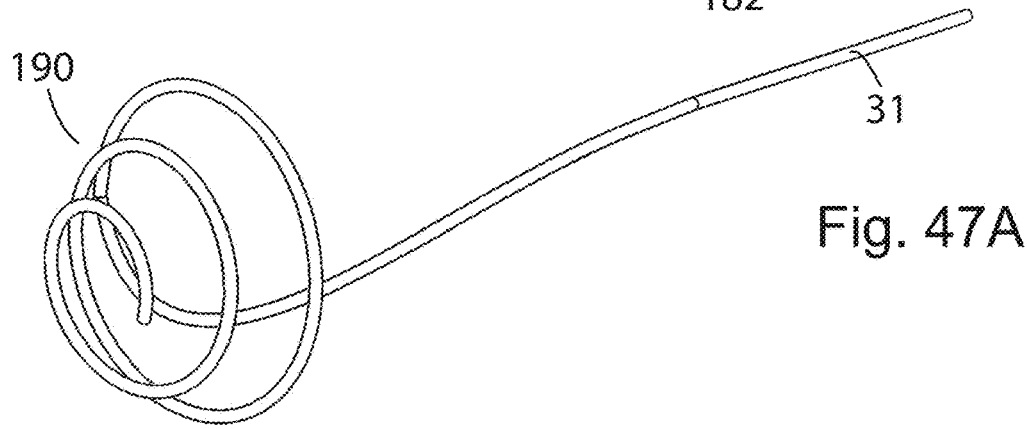
FIG. 47A and FIG. 47B are perspective and side elevational views of a further embodiment of a helical coil forming part of device according to the disclosure.
Figure 47B:
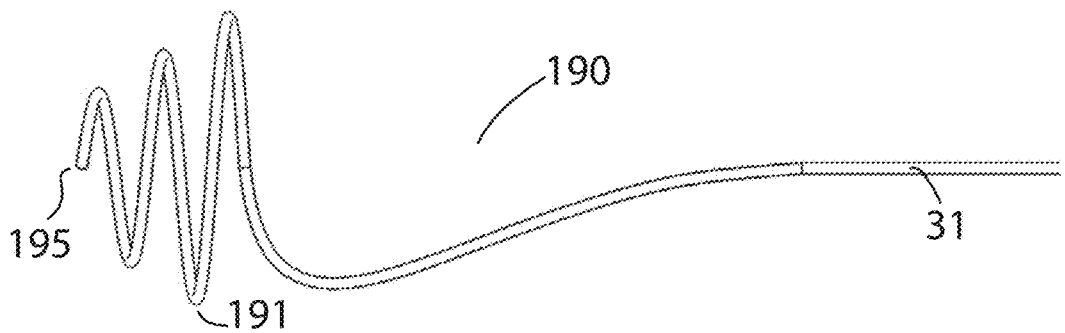

FIGS. 47A and 47B illustrate a vein denuding head forming part of a device of the present disclosure, and indicated generally by the reference numeral 190, and comprising a control arm 31 and helical coil 191 having approximately three turns (coils) that decrease in diameter distally towards the distal tip 195.

Figure 48A:
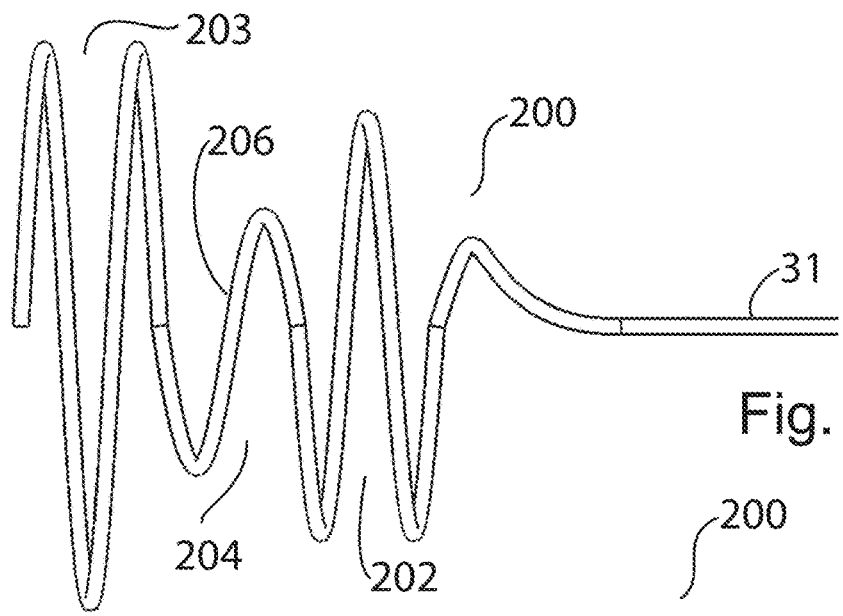
FIGS. 48A to 48C are side elevational views, and a perspective view, of a further embodiment of a helical coil forming part of device according to the disclosure.
Figure 48B:
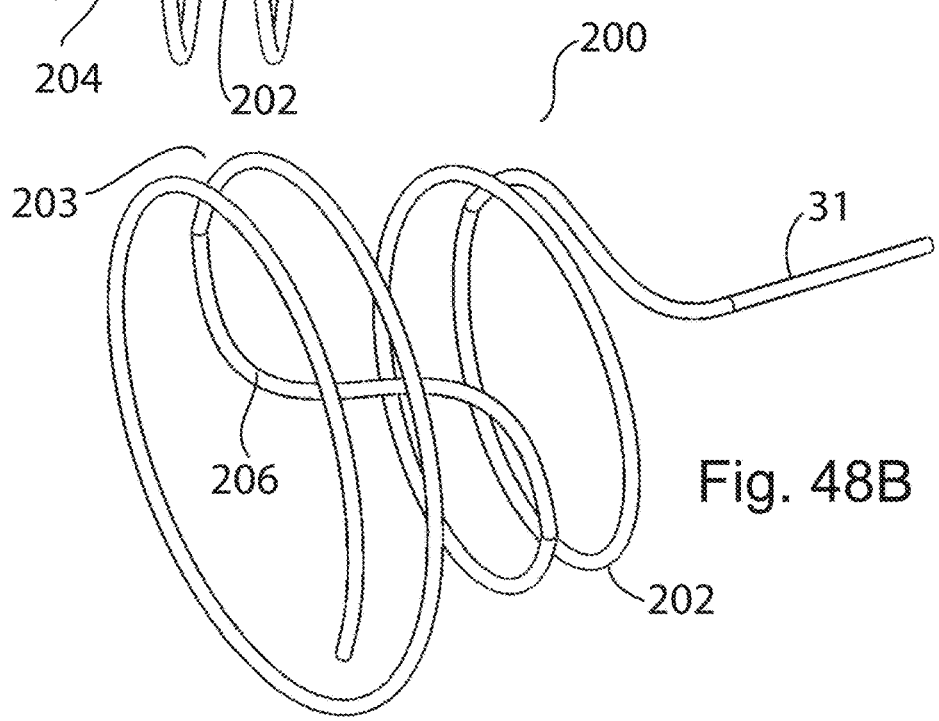
Figure 48C:
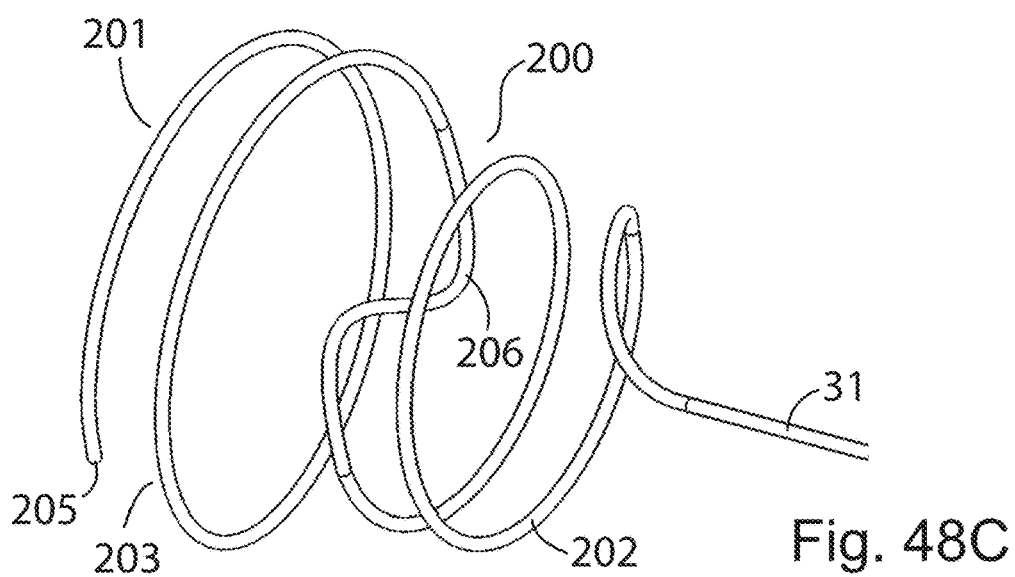

FIGS. 48A, 48B and 48C illustrate a vein denuding head forming part of a device of the present disclosure, and indicated generally by the reference numeral 200, and comprising a control arm 31 and helical coil 201 having approximately three turns (coils) and comprising a proximal right-handed coil element 202 of about two turns, a distal left-handed coil element 203 with about 1.5 turns, and transition member 204 with a turn section 206, and a distal tip 205. The turn section 206 allows the smaller diameter right-handed proximal coil 202 transition to a larger diameter left-handed distal coil 203.

FIGS. 49A to 51A illustrate a number of vein denuding heads forming part of devices of the present disclosure, and in particular vein denuding heads have two unconnected helical coils axially spaced apart, in which parts described with reference to previous embodiments are assigned the same reference numerals.

Figure 49A:
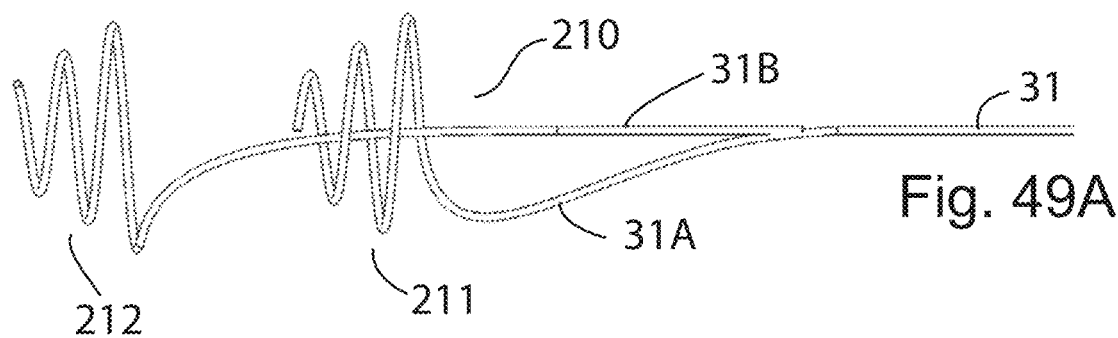
FIG. 49A and FIG. 49B are side elevational and perspective views of a vein-denuding head forming part of a device according to the disclosure, having two axially spaced-apart helical coils.
Figure 49B:
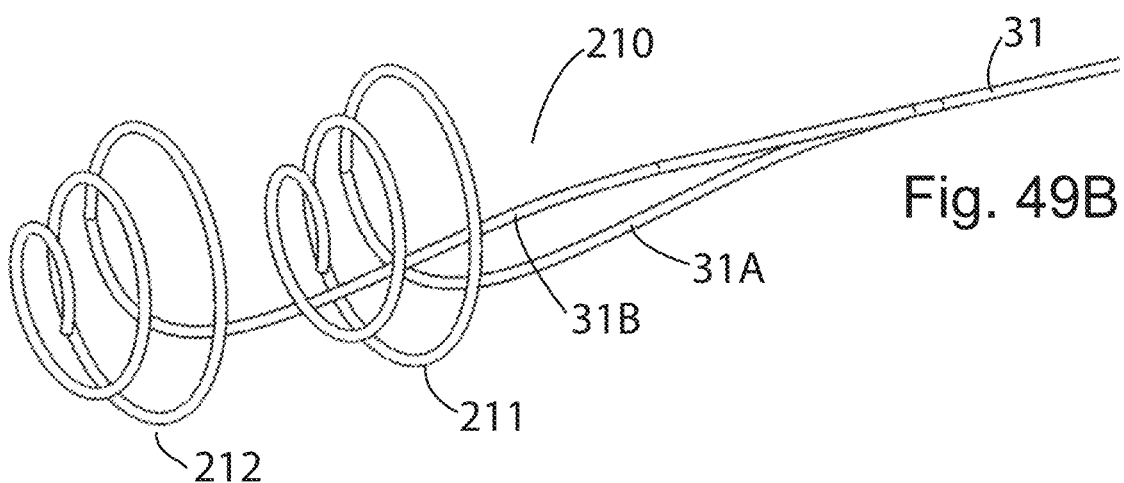

FIGS. 49A and 49B illustrate a vein denuding head forming part of a device according to the present disclosure, indicated generally by the reference numeral 210, and comprising a control arm 31 which is bifurcated at a distal end to provide control elements 31A and 31B, a proximal helical coil 211 operatively attached to control element 31A and a distal helical coil 212, axially spaced apart from the proximal helical coil, and operatively attached to control element 31B that passes through the proximal helical coil. Each helical coil has slightly more than two turns (coils) and is generally conical with a diameter that increases proximally.

Figure 50A:
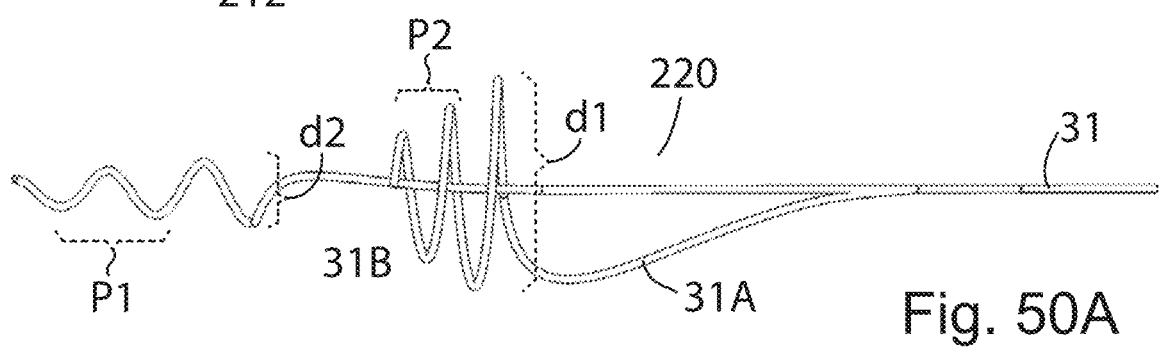
FIG. 50A and FIG. 50B are side elevational and perspective views of a vein-denuding head forming part of a further device according to the disclosure, having two axially spaced-apart helical coils.
Figure 50B:
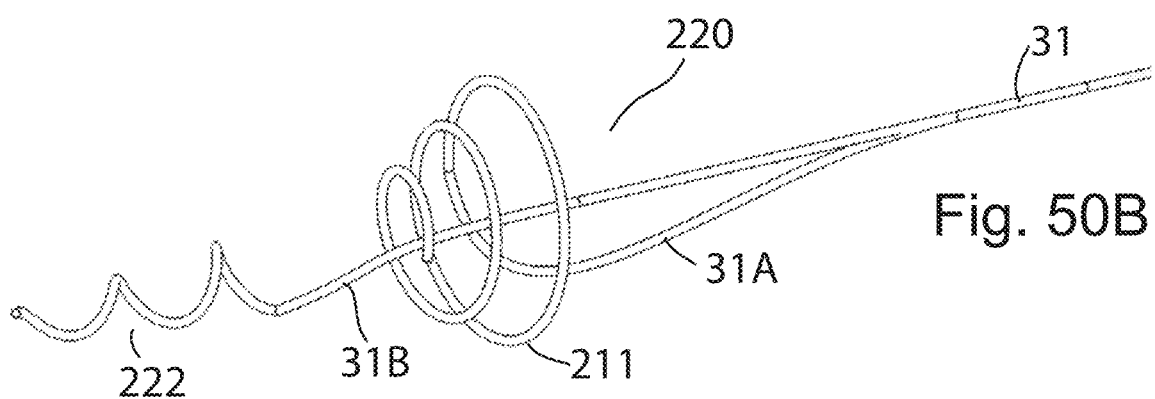

FIGS. 50A and 50B illustrate a vein denuding head forming part of a device according to the present disclosure, indicated generally by the reference numeral 220, and comprising a control arm 31 which is bifurcated at a distal end to provide control elements 31A and 31B, a proximal helical coil 221 operatively attached to control element 31A and a distal helical coil 222, axially spaced apart from the proximal helical coil, and operatively attached to control element 31B that passes through the proximal helical coil. Each helical coil has slightly more than two turns (coils) and is generally conical with a diameter that increases proximally. In addition, the maximal diameter of the proximal coil d1 is approximately three times the maximal diameter of the distal coil d2, and the pitch of the distal helical coil p1 is about two times that of the proximal helical coil p2.

Figure 51A:
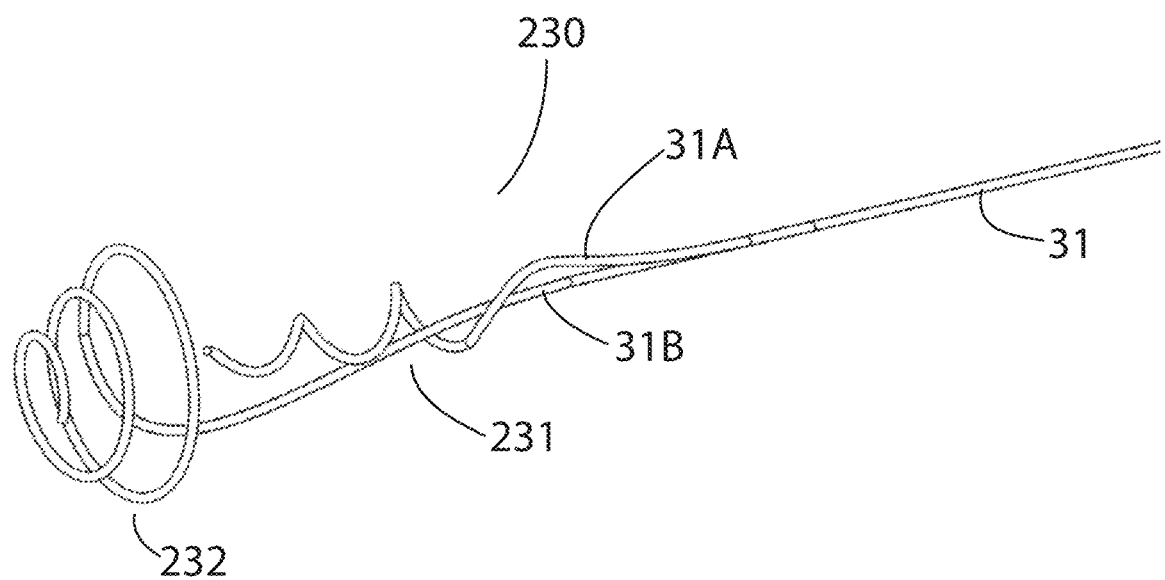
FIG. 51A is a perspective view of a vein-denuding head forming part of a further device according to the disclosure, having two axially spaced-apart helical coils.

FIG. 51A illustrates a vein denuding head forming part of a device according to the present disclosure, indicated generally by the reference numeral 230, and comprising a control arm 31 which is bifurcated at a distal end to provide control elements 31A and 31B, a proximal helical coil 231 operatively attached to control element 31A and a distal helical coil 232, axially spaced apart from the proximal helical coil, and operatively attached to control element 31B that passes through part of the proximal helical coil. Each helical coil has slightly more than two turns (coils) and is generally conical with a diameter that increases proximally. In addition, the maximal diameter of the proximal coil is approximately one third of the maximal diameter of the distal coil, and the pitch of the distal helical coil is about half that of the proximal helical coil.

Figure 61A:
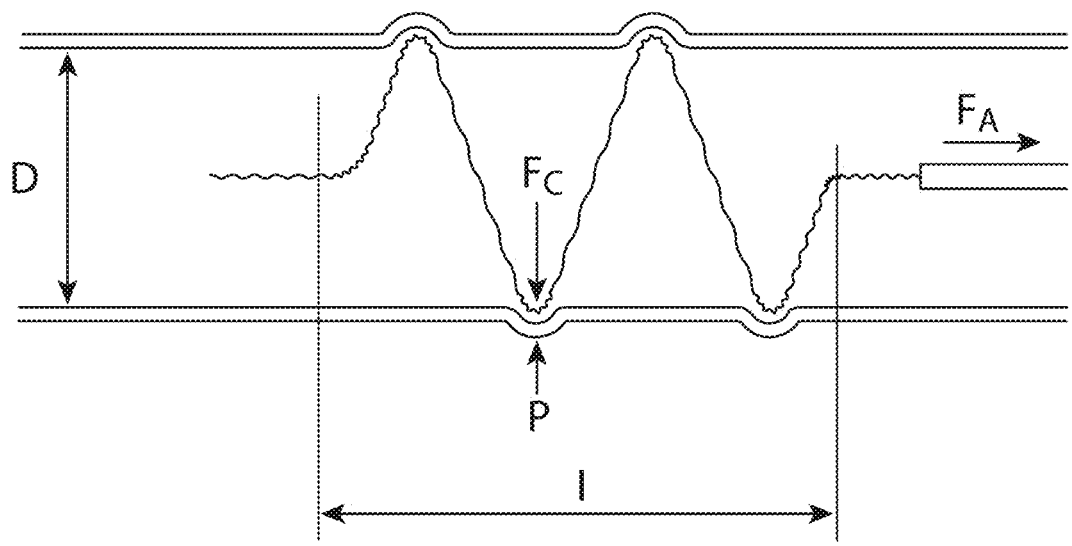
FIGS. 61A to 61C illustrate the static force variables on the deployed coil as it comes under an axial Force FA; (A) prior to movement at the beginning of withdrawal in a vessel of diameter D with contact force of the coil outwards FC and constraint force of the vessel P; (B) lengthened to a length of L in a narrowed vessel of diameter d; (C) In a significantly narrowed vessel of diameter e with the coil lengthened to S. There is loss of vessel wall contact over proximal section of coil to reduce static friction and allow atraumatic passage of the coil.

Referring to FIG. 61A when the coil is deployed and engages the internal surface of the vessel lumen there is static friction between the device and the vessel wall. At rest there is an outward radial force at the coil contact points (FC) which is proportional to the stiffness and diameter of the coil and the diameter of the vessel. This is counterbalanced by a constraint force of the vessel P. As the user withdraws the device the axial force, FA, increases to overcome static friction. In sliding systems between solid objects the friction force is proportional to the loading contact force (FC) and surface roughness, described by Amontons' law of friction. It has also been shown that contact surface area is a factor which increases friction [11].

Figure 61B:
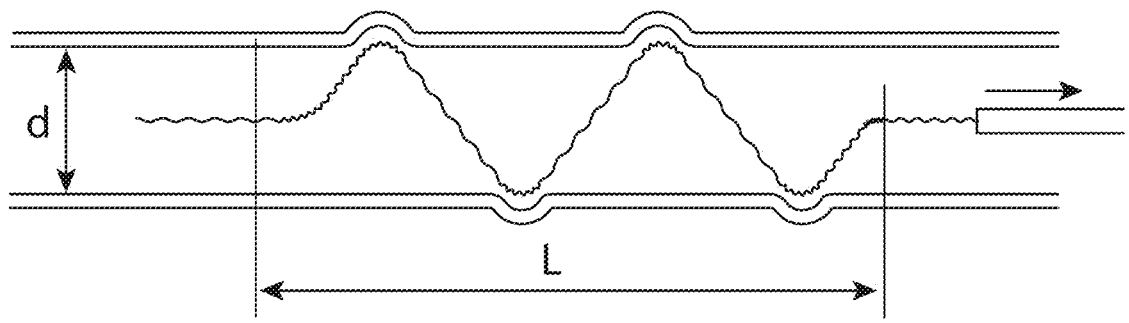

Ideally as the axial force (FA) increases, static friction is overcome before the coil begins to lengthen. Static friction in veins and arteries is generally low due to the presence of the gel like glycocalyx layer which has been shown to reduce static friction [12]. When the vessel constraint force is increased as in venospasm, a greater axial force is required which leads to lengthening of the coil while still remaining in contact with the vessel wall due to its resilient deformability as illustrated in FIG. 61B. The axial force required to cause coil lengthening is proportional to the wire stiffness and is also affected by the wire profile (flat vs round).

Figure 61C:
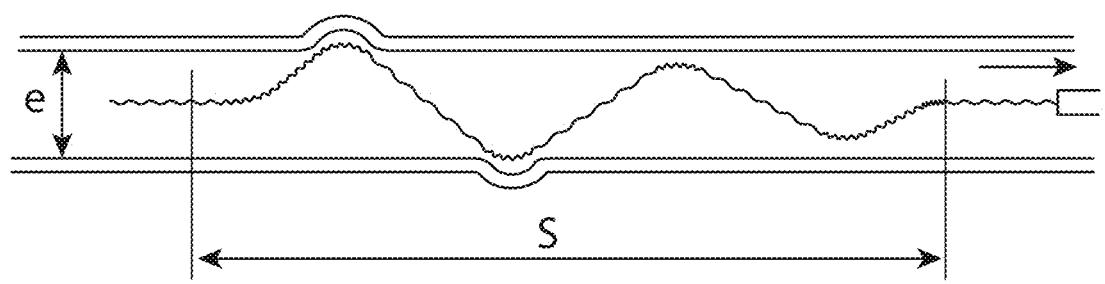

In some instances, as illustrated in FIG. 61C, there is significant constraint force on the device due to excessive venospasm or natural obstructions due to vein valves. The increased constraint force is usually focused on a distal portion of the coil in this situation. As the axial force increases further the coil reduces its diameter enough to lose contact with the vessel wall as illustrated in FIG. 61C. This dramatically reduces static friction and can narrow the distal end to allow it to overcome static friction and/or an obstruction. When this occurs the coil jumps or skips proximally during recoiling to adopt its natural configuration. This can cause small sections of vein wall to be missed by the abrasive surface. In some instances, such as passing through very narrow constrictions or vein valves, some coil deformation causing loss of contact is desirable to allow the coil to reduce static friction before the axial force becomes too high as to cause vessel wall damage or vein stripping. Vein stripping occurs when the distal tip of an intraluminal device acts like an anchor to transmit axial forces which are great enough to strip or remove an entire vein segment from the surrounding tissue. This has been documented with previous devices for vein ablation that have a non-deformable less elastic designs and causes significant pain and bruising for the patient as well as complicating the procedure [6].

To overcome excessive coil lengthening and resultant skipping, variables related to static friction and coil deformability can be modified by altering the thickness, shape, diameter and/or stiffness of the device element. The surface roughness should remain constant to achieve sufficient mechanical ablation.

The use of other coil configurations can also limit the effect of skipping on endothelial coverage. Such embodiments of the device are illustrated in FIGS. 42A to 51A. FIGS. 45A-45B and 46A-46B incorporate a coupling segment (174, 184) which can act to prevent excessive lengthening across the entire coil. FIGS. 48A-48C illustrate a coupling segment between coils with opposing clockwise and anti-clockwise configurations to resist excessive lengthening. FIGS. 49A to 51A illustrate separate coil elements to provide coverage should either coil element be exposed to excessive static friction and lose contact during lengthening.

Figure 63:
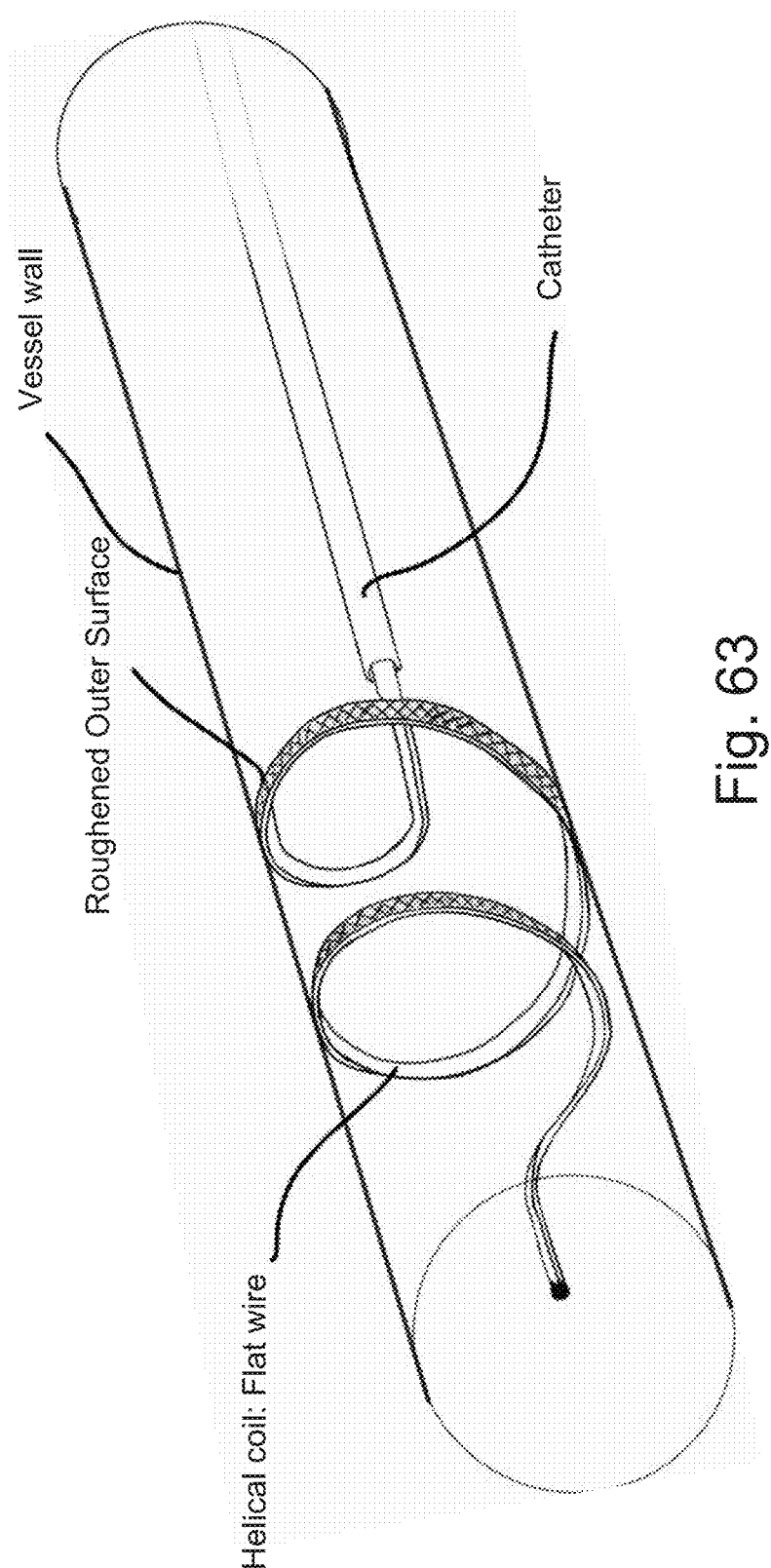
FIG. 63 illustrates an oblique view of an embodiment with a flattened wire having a smooth inner surface and roughened outer surface with a diamond pattern in a typical vessel.

Referring to FIG. 63, in another embodiment there is a single flat wire option. This flat wire is formed from Nitinol. The outer surface of this wire is textured (roughened) using a knurling process that presses a shape into the wire, similarly the texture can be applied by other means for example stamping or micro machining. This creates abrasive features in the wire. Reference FIG. 37A which shows a diamond knurl pattern pressed into the Nitinol wire. The wire outer surface can also be shot blasted to create a micro-abrasive surface on the wire. This flat wire is subsequently held in a heat setting fixture and shape set in a helical profile. The helical coil with its abrasive outer surface is configured to shear the inner lining of the vein (primarily but not limited to the endothelial cell layer) when the helical coil is moved axially along the vein in a deployed configuration.

Venous Disease

The device and method of the present disclosure may be employed to treat or prevent venous disease. A combination of vein valve failure and vein wall weakness leads to the reflux of blood with subsequent complications of blood pooling in the lower limbs. The goal of superficial venous reflux treatment is to remove or occlude the refluxing vein allowing blood to divert to healthy veins and circulate effectively back to the heart. The Great Saphenous Vein (GSV) is the longest vein in the body and the most commonly treated vein for venous reflux disease. It's pathway runs from the foot to the groin where it has a junction with the deep femoral vein. The GSV is most commonly the cause of venous reflux. Other veins include the Small Saphenous Vein (SSV), Anterior Accessory Saphenous Vein (AASV) and numerous tributary veins which can also be targets of treatment.

The venous network of the lower limbs is divided into three components: 1) superficial veins located in the superficial compartment superficial to the muscular fascia, draining the skin and subcutaneous tissue 2) deep veins that lie deep to the muscular fascia and drain the muscles of the lower limb, and 3) the perforating veins that penetrate the muscular fascia and connect the superficial and deep veins.

Understanding the fascial layers and compartments of the leg that these veins are located in is important in understanding the risks involved in current treatment approaches. The GSV typically follows a course close to the skin at a depth of 2 to 5 cms in persons of normal body habitus. It is bounded from the lower leg to the groin in an enclosed fascial space by the muscular fascia below it and the saphenous fascia above. The latter being a portion of the membranous layer of the subcutaneous tissue. The two fascial layers, with the saphenous fascia above and muscular fascia below, merge at each end to form a closed space, which is called the saphenous compartment. The saphenous compartment contains the saphenous vein and the accompanying arteries and nerves. The saphenous nerve is usually far from the great saphenous vein (GSV) and not in the saphenous fascia above the knee. However, the saphenous nerve lies in close proximity to GSV and is located within the saphenous fascia below the knee. The only truncal vein located in the saphenous compartment is the GSV or its duplicate. All of the tributary veins and accessory veins are located in the subcutaneous compartment, external to the saphenous fascia and the saphenous compartment.

Segmental hypoplasia of the GSV occurs in 25% of patients with superficial venous disease [13]. This hypoplastic segment in the thigh is often bridged by an accessory vein which runs outside the saphenous compartment closer to the skin. If this or any other part of the GSV runs in very close proximity to the skin it may be difficult to create a plane of tumescence anaesthesia around the vein to protect the skin in preparation for thermal venous disease treatment. In some instances only non-thermal methods or stripping of the vein can be performed. Tributary veins in the thigh run outside the saphenous compartment and may become varicose in appearance if reflux develops. These are also less amenable to thermal treatment due to their more superficial position. The primary two tributary veins in the thigh are the anterior and posterior thigh circumflex veins. The Anterior Accessory saphenous vein in the thigh runs within the saphenous compartment in parallel to the GSV but is not consistent, present in approximately 14% of patients with varicose veins. The small saphenous vein (SSV) begins at the lateral malleolus and drains into the deep vein in the popliteal space behind the knee. It is close to the sural nerve which is vulnerable to injury using thermal methods [14]. The fascial relationships of the SSV are more consistent than the GSV.

Perforating veins connect the superficial veins with the deep veins by perforating the muscular fascia. There are up to 150 perforating veins in the lower extremity with variable size and distribution. The medial calf perforators are the most clinically significant and can lead to high velocity blood flow into the superficial system and venous hypertension. They are difficult to treat with surgical, thermal, glue and/or sclerosant methods due to their short length and close proximity to the deep venous system. Inadvertent propagation of heat, glue or chemical sclerosant directly into the deep venous system can lead to DVT and subsequent PE, a potentially fatal complication. Open surgical ligation is technically difficult and leads to significant morbidity from the incision. The junction of the GSV and SSV with the deep femoral veins, in the groin and posterior knee respectively, are also junctional points between the superficial and deep systems and treatment of the incompetent superficial vein close to these regions carries a risk of thromboembolic complications.

In view of these anatomical considerations, the use of thermal energy is limited due to the inherent risk of injury to adjacent skin and nerves. Furthermore, forward propagation of heat energy into non-target tissues in the deep venous system is a potential cause of DVT and subsequent PE. Current non-thermal methods are also limited by the risk of damaging adjacent non-target tissues. Cyanoacrylate glue can be inadvertently placed in the deep venous system without the ability to retrieve or recapture it. Chemical sclerosants by their nature are effectively circulated into the deep venous system as they flow from the target site. Foam sclerosant preparations can propagate in clumped emulsions of sclerosant and air traveling into the deep venous system potentially damaging the endothelium and leading to DVT. Chemical sclerosants can also be inadvertently injected into subcutaneous tissue, nerves or arteries causing significant skin necrosis.

To counteract these limitations, an effective non-thermal device should have the ability to be accurately and precisely deployed using standard ultrasound techniques. It should also be possible to retrieve and recapture the device if mal-positioned prior to treatment. No currently marketed device has this dual capability.

A mechanical ablation device, with the ability to be accurately deployed at a target site without the risk of uncontrolled forward propagation or damage to surrounding tissues is preferable for the treatment of lower limb venous reflux. The ability to recapture and reposition further reduces the risk of user related error.

The method provided of vein occlusion without the use of a permanent implant or toxic agent is preferable as it avoids the risk of infection, immune mediated inflammatory response, neurological side effects, debris migration secondary to implant mechanical fatigue and patient discomfort due to mass effect.

Bioabsorbable implant techniques have also previously failed to provide long term venous occlusion with recanalisation occurring following absorption [15].

Surprisingly, the authors have discovered that by using a purely mechanical non implantable solution, the natural thrombotic occlusion acts like an "implant" and is converted by the bodies natural healing mechanisms into a permanent occlusion in a process known as fibrotic transformation of thrombus.

Further to the method of occluding the GSV, SSV, AASV or large superficial tributary veins there is provided a method for treating smaller length incompetent tribuatry veins which commonly exist below the knee. These are currently treated with a procedure known as phlebectomy. This involves making a stab skin incision under local anaesthetic and using a vein hook device to manually extract the short vein segment. This procedure is often performed on multiple vein segments in the leg. It can be painful and uncomfortable for patients due to the requirement for multiple needlestick injections of local anaesthetic and the difficulty in fully anaesthetising each vein segment. Often due to unacceptable patient discomfort or physician preference, chemical sclerosant is used instead. The increased number of injections of chemical sclerosant can increase the risk of systemic toxic side effects and local complications including skin necrosis from inadvertent injection of sclerosant into the subcutaneous tissue or arterial system.

Figure 66:
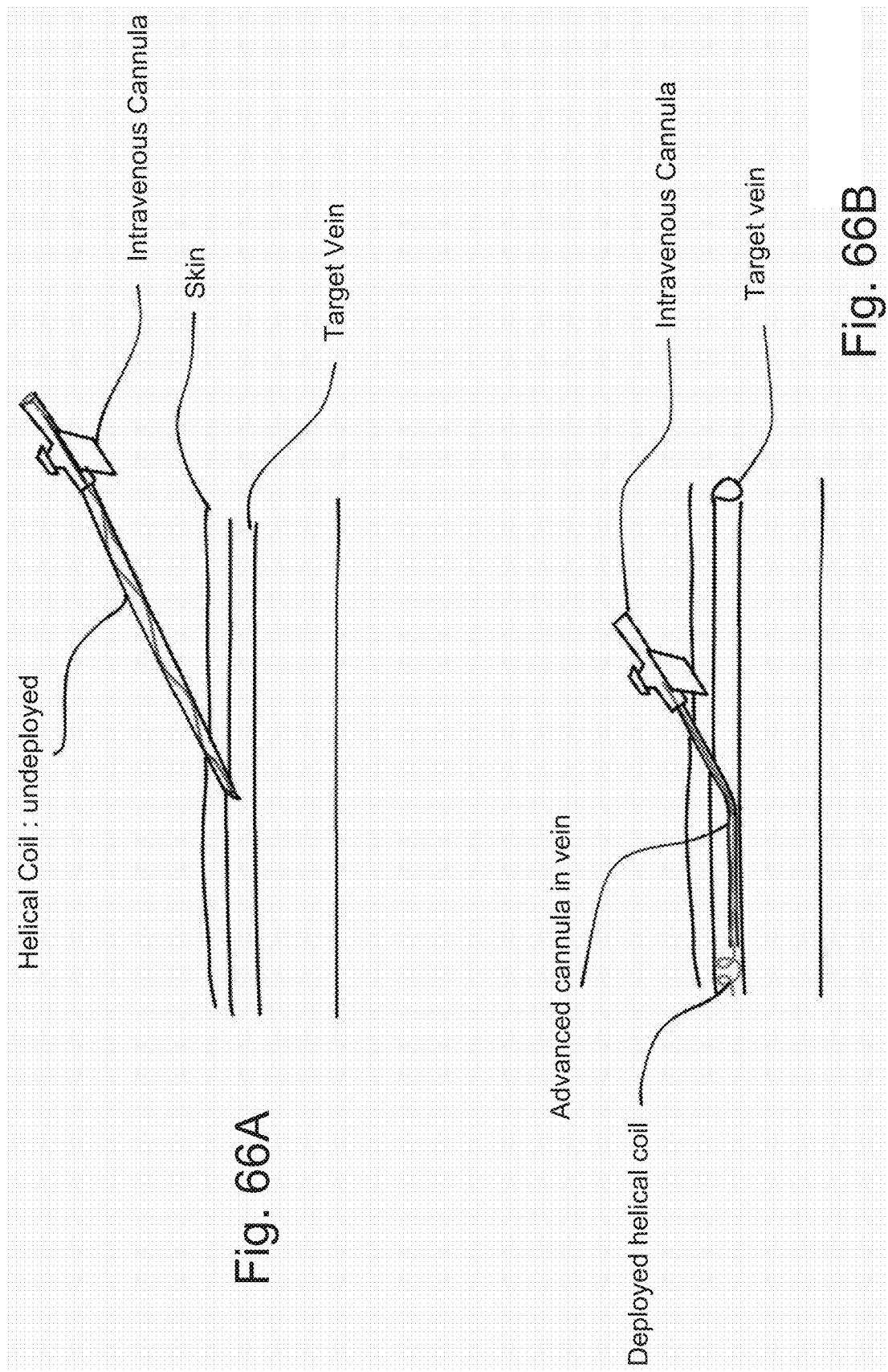
FIG. 66A and FIG. 66B illustrate the use of a modified cannula as shown in FIG. 65, to access a target vein and deploy a helical coil following withdrawal of the outer sheath.
Figure 67:
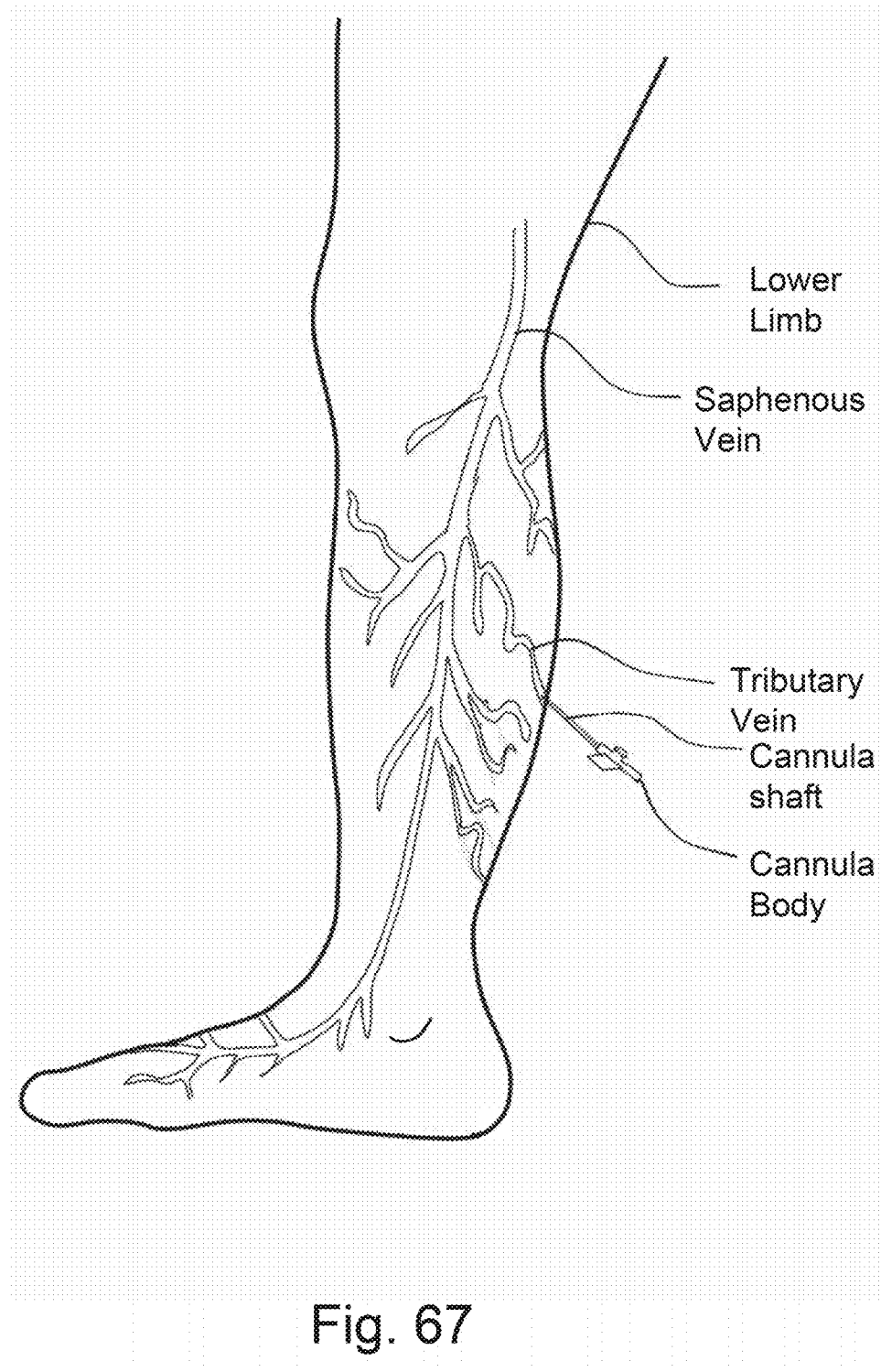
FIG. 67 illustrates the access of superficial leg tributary veins with the cannula device of FIG. 65.
Figure 68A:
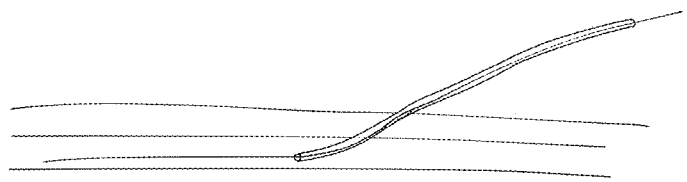
FIGS. 68A to 68D illustrate a method of deploying a miniaturised coil in tributary veins. (A) Intravenous access with a guidewire is achieved and a sheath is inserted over the guidewire; (B) The sheath is advanced in the vein and the guidewire is removed; (C) The sheat is withdrawn to expose the stored helical abrasive coil element; (D) The sheath and coil are withdrawn together to treat the vein section.
Figure 68B:
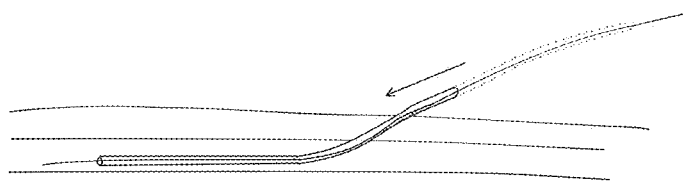
Figure 68C:
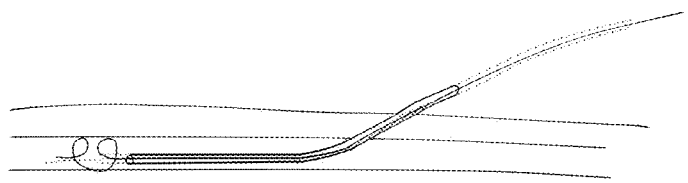
Figure 68D:
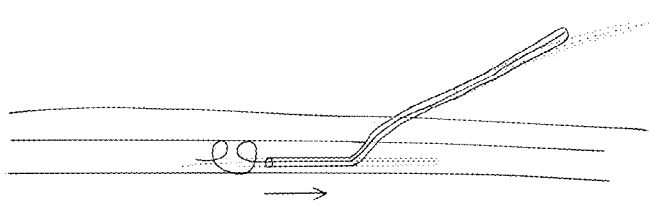

In one embodiment the method of treating small tributary veins is performed with a miniaturised helical coil as illustrated in FIGS. 66A-66B and 67. The mechanism of action provided by this embodiment is the same as previously described for the treatment of large veins such as the GSV. Following insertion into the target vein, a miniaturised coil with abrasive outer surface is deployed exerting a radial force on the vein wall. This surface denudes the inner layer upon withdrawal.

Figure 65:
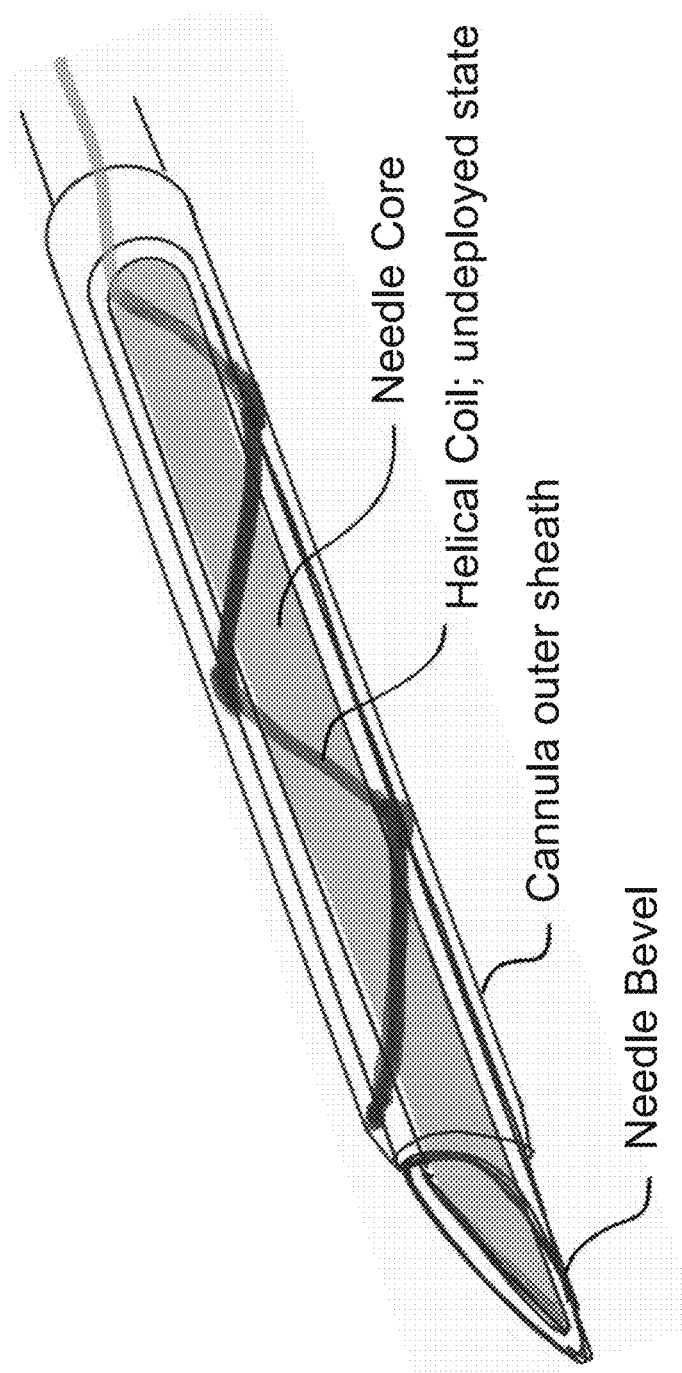
FIG. 65 illustrates the tip of a modified intravenous cannula modified to store a miniaturised helical coil in an undeployed state.

Referring to FIG. 65 in one embodiment the helical coil is loaded around the needle as part of an intravenous cannula. Modifying the current arrangement of an intravenous 14G cannula to decrease the size of the needle used for entering the vein while maintaining the outer diameter of the sheath at 2.1 mm allows accommodation of the helical coil as illustrated in FIG. 65. Creating a more tapered tip with the polyurethane outer catheter would allow skin access. Using current intravenous access techniques of vein access, needle withdrawal and cannulae advancement as shown in FIG. 67. The miniaturised coil section could be deployed by partial withdrawal of the outer polyurethane cannulae (FIGS. 66A and 66B). When the end of the treatment zone is reached the outer cannula can be used for recapture and atraumatic removal of the coil. This proposed technique reduces the need for local anaesthesia as stab skin incisions are not required nor is any traction on the vein required to pull out the vein as in hook phlebectomy procedures. There is also no requirement for chemical sclerosant reducing the associated risks of skin necrosis.

Referring to FIGS. 68A-68D in another embodiment the vein is accessed with a small gauge needle and a guidewire is passed into the vein. An outer sheath similar to an introducer sheath, is passed over the guidewire as illustrated in FIGS. 69A-69B. This outer sheath is manufactured to contain the coil adherent to its inner lining just below the aperture at the tip.

Figure 70A:
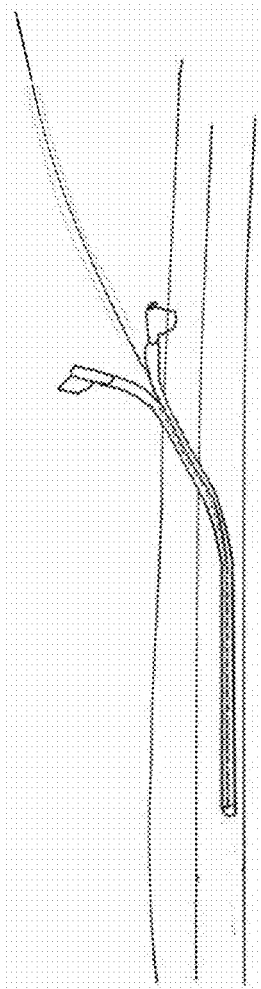
FIGS. 70A and 70B illustrate a method using a peel away introducer sheath to deploy a helical coil in a target vein.
Figure 70B:
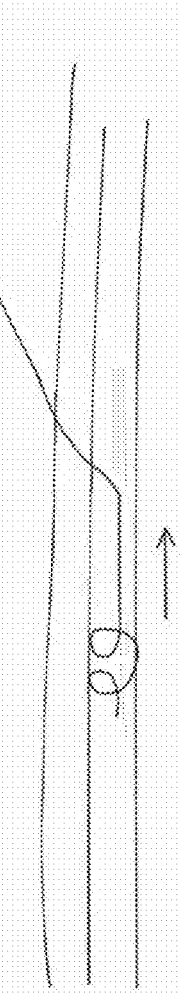

This allows the guidewire to pass through and past the coil within the introducer. The coil is then deployed by partial withdrawal of the outer sheath FIGS. 68A-68D. In another embodiment the coil is deployed by using a peel-away introducer sheath as shown in FIGS. 70A and 70B. In one embodiment, the coil can be reloaded into the sheath and used on separate veins.

There follows a description of some indications associated with body lumen that may be treated with the device and methods of the present disclosure:

Pelvic Vein Reflux

Abnormal reflux of blood in pelvic veins has been shown to be an important but often previously unrecognised cause of recurrent varicose veins in the leg, vulval/vaginal varicose veins and a condition known as Pelvic Congestion Syndrome (PCS). It is also thought to be linked to haemorrhoids. Reflux in the internal iliac veins and ovarian veins in females are usually responsible for the development of these conditions.

PCS is characterized by visible congestion of the pelvic veins on venography in women with a history of chronic pelvic pain for more than six months. Most commonly the left ovarian vein is the cause of reflux and pelvic varicosities. Morbidity associated with PCS can be severe leading to a significant reduction in quality of life and patient discomfort. PCS manifests with different intra-pelvic symptoms including non-cyclical pain, urinary frequency and dyspareunia. Current treatment is generally performed using catheter access via the jugular or femoral vein, following which the ovarian veins and/or the internal iliac veins are occluded using metal embolization coils, chemical sclerosants such as 3% sodium tetradecyl sulfate (STS), or a combination of both. Disadvantages of coil embolization include the high cost of treatment related to coil devices and the risk of complications including coil migration and vein rupture. Coil migration occurs when coils travel inadvertently to non-target sites such as the renal vein or via the inferior vena cava to the pulmonary veins causing pulmonary embolism. Coil migration has been reported to occur in up to 4% of cases and can lead to significant morbidity [16]. Some patients report persistent pelvic discomfort or flu like symptoms which is of unknown cause but could be related to the coil implants. The use of endothermal laser or radiofrequency vein ablation has not been adopted for the treatment of pelvic venous insufficiency. This is primarily due to the risk of thermal damage to important surrounding pelvic structures adjacent to the vessel wall. While transmural vessel perforation and damage to surrounding tissues is rare with endothermal techniques, the consequences during treatment within the pelvis are far greater than in the lower limb. Furthermore, large volumes of tumescent anaesthesia are injected around lower limb veins during treatment to shield surrounding tissues and prevent thermal injury and pain. This is obviously not possible within the pelvis. Accordingly, a safe and cost-effective device is still required for the treatment of pelvic vein reflux by occlusion. An optimal solution would be provided by a non-implantable, non-thermal method to reduce these risks.

Figure 71:
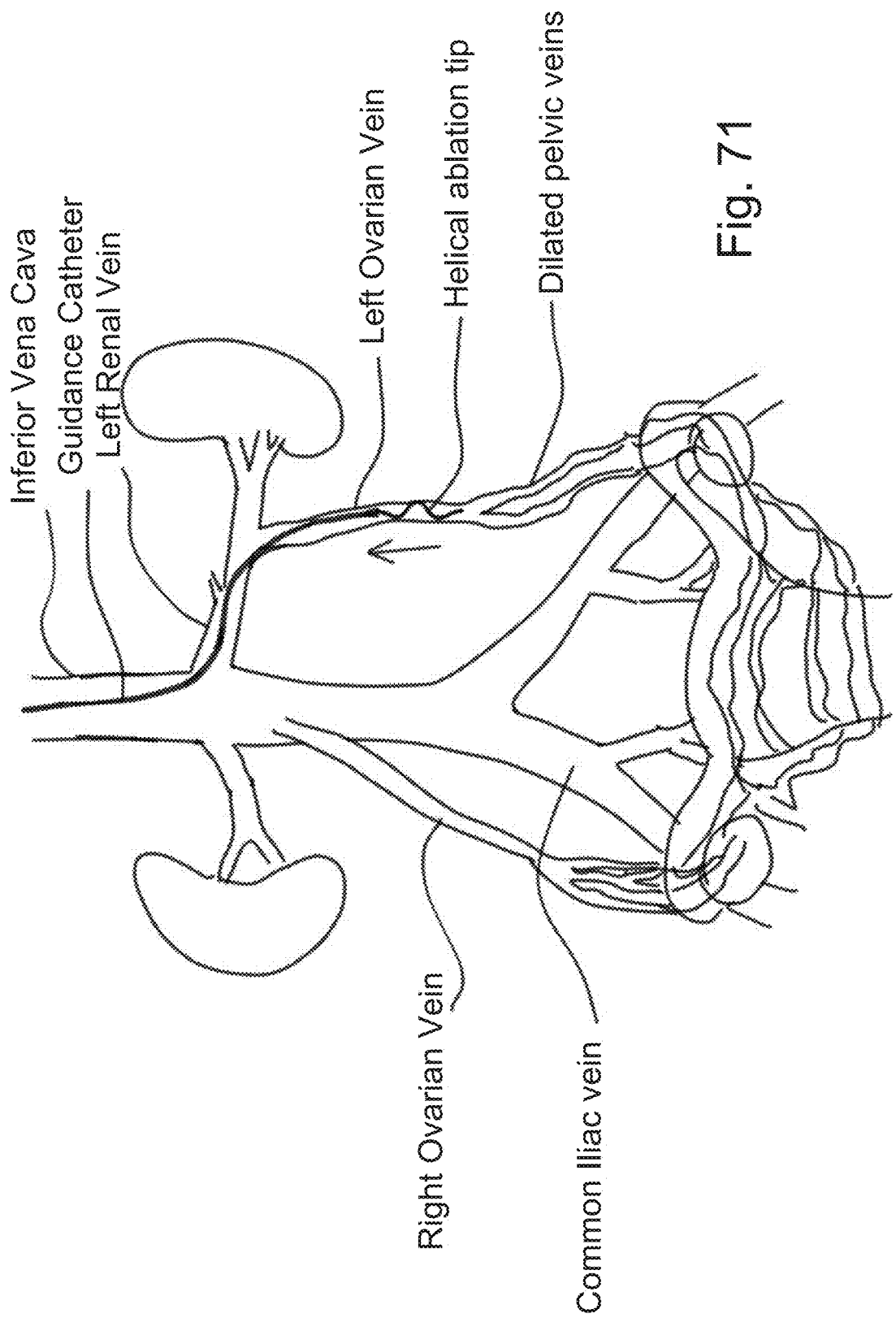
FIG. 71 illustrates the use of a helical ablation coil to treat pelvic vein reflux in the left ovarian vein.

In one aspect, the method of the present disclosure may be employed for the treatment of pelvic vein reflux in which a helical coil device is used to mechanically denude the internal iliac and or ovarian veins to cause permanent occlusion. This occlusion will prevent venous reflux to the leg veins which causes recurrent varicose veins, the venous territories supplying the vagina/vulva and venous territories involved in PCS. In another embodiment the denudation procedure can be combined with temporary balloon occlusion to reduce blood flow and promote adherence of thrombus to the treated section of vein. This could be especially beneficial in pelvic veins with higher volume reflux and velocity. In one embodiment the procedure could be enhanced by the combined use of chemical sclerosant and/or embolisation particles. FIG. 71 is a schematic showing the venous anatomy relating to the pelvic vein reflux and the use of a helical coil to denude the internal iliac veins and prevent refluxing flow to the venous territories involved thus curing symptoms.

Deep Vein Reflux

Deep vein reflux caused by incompetent venous valves involving the femoral vein in the lower limb cannot be treated by ablation and occlusion as it is vital for circulatory return of blood from the limb to the heart. Some incompetent venous valves have been obliterated by DVT but other are maintain normal valve leaflets but due to wall laxity they no longer oppposle correctly to prevent reflux. Current methods of treatment involve invasive surgical procedures to create neovalves. Accordingly, there is a need for a less invasive procedure to restore venous valve function. In one aspect, the method of the present disclosure may be employed for the treatment of deep vein reflux in which the helical coil device is deployed and withdrawn across an existing valve. The outer surface is mildly abrasive to reduce the risk of thrombotic occlusion while maintaining the ability to disrupt the endothelial layer. This causes hypertrophy of the valve leaflets and surrounding tissue with the effect of bringing the valve leaflets closer together and restoring the one-way valve function to prevent reflux.

Haemorrhoids

As mentioned previously haemorrhoids can be treated with pelvic vein embolisation. Newer techniques also target the specific occlusion of the superior rectal artery to prevent filling of the dilated venous plexus causing the internal haemorrhoids [17]. This artery is between 3 and 5 mm in diameter in most instances. To avoid the placement of a permanent implant and offer a more cost-effective solution for this common condition, improved treatments are required. In one aspect the method of the present disclosure is for treating hemorrhoids in which a helical coil device is used to mechanically denude the superior rectal artery to cause permanent occlusion and prevent filling of the venous plexus thus curing the condition.

Varicocele

A varicocele is an abnormal dilation of veins surrounding the testes in men. Clinically significant varicoceles are present in up to 15% of adult men leading to pain, discomfort and reduced fertility. Treatment is recommended in young men with testicular atrophy or reduced fertility. Current treatment involves occluding the testicular vein which supplies the abnormal dilated veins around the testes. Current methods of occlusion include permanent coil embolisation, glue, chemical sclerosant or a combination of techniques. Accordingly, a less invasive, more cost-effective method is still required for the occlusion the testicular vein which supplies the dilated veins in a varicocele. In one aspect, the method of the present disclosure may be employed for the treatment of varicoceles in which a single use helical coil is used to mechanically denude the testicular vein to cause permanent occlusion. FIG. 55 is a schematic showing the venous anatomy and the related procedure to cause permanent vein occlusion.

Portal Vein Occlusion

Preoperative portal vein embolisation (PVE) is an elective procedure to terminate portal blood flow to a selected portion of the liver prior to major liver resection. PVE, initiates hypertrophy of the liver tissue that is to remain following the planned major resection and may allow a more aggressive resection. It is used as an adjunctive step in the treatment of primary and secondary liver metastases from colorectal cancer. Current techniques involve access to the portal venous system using direct image guided transhepatic access with subsequent injection of embolisation agents including glue, polyvinyl alcohol (PVA) and metallic spheres or coils. Many of these techniques are costly and the patient may be inoperable during the course leading up to the planned resection. Accordingly, a more cost-effective approach is required. Due to the pro-coagulative state of most patients undergoing portal vein procedures as an adjunct to tumour resection, a non-implant method relying on thrombotic occlusion of selected portal veins could be effective. In one aspect, the method of the present disclosure may be employed for the preoperative occlusion of portal veins is proposed in which a helical coil device is used to mechanically denude the portal veins to cause occlusion. This occlusion will promote hypertrophy of the remaining liver segments and improve the likelihood of patient survival post planned resection. FIG. 53A is a schematic representation of portal vein occlusion using a non-implant mechanical denudation method.

Vein Grafts

Coronary artery bypass graft (CABG) surgery is the standard of care for patients with left main coronary artery disease (CAD) and three-vessel CAD. Peripheral artery bypass grafting (PABG) surgery is performed in patients with late-stage peripheral artery occlusive disease. The internal mammary artery is commonly used for revascularization in coronary bypass surgery, however, veins (almost exclusively the great saphenous vein) remain the most commonly used grafts, especially for PABG surgery. The interposition of vein grafts into the arterial system exposes the vein to higher stretch forces and shear stress which may result in excessive inflammatory changes within the venous wall known as intimal hyperplasia leading to occlusion and vein graft failure. The patency rate at 10 years following vein graft surgery is only 60% [18]. It is not well understood why some vein grafts remain patent while others become occluded in the long term. All veins undergo some remodelling or "arterialisation" when transferred to the arterial system. However, an excessive and persistent inflammatory response causes graft failure in the long term. New research indicates that the condition of the vein prior to grafting may be an important predictor of graft failure. Veins with already hypertrophic, synthetic predisposed smooth muscle cells in the media layer have a worse prognosis. Accordingly, a way to increase the long-term success rates of vein grafts for arterial disease is an important clinical need and may be achieved by preconditioning or modifying the vein graft prior to use as a conduit in the arterial system. In one aspect of the present disclosure a method for the pre-treatment of veins to be used as grafts in the arterial system for the treatment of CAD and PAD is proposed. A helical coil with a less abrasive surface or partially abrasive surface is provided to cause vein wall thickening without complete thrombotic occlusion and subsequent fibrosis. The depth of vein wall disruption must be specific to develop the correct inflammatory response which does not predispose the vein to graft failure. This adjunctive procedure is performed ideally 4 to 12 weeks prior to graft implantation to allow the cellular changes involved in vein remodelling to occur and subside. This may improve the ability of the vein to adapt to the arterial environment of greater pressure and higher shear forces because the inflammatory changes have already taken place and stopped following a once-off mechanical disruption by the treatment. The uncontrolled excessive inflammatory and hypertrophic changes will then be less likely to occur when placed into the arterial system. This could prevent excessive uncontrolled media hypertrophy and intimal hyperplasia occurring and reduce the risk of mural atheroma formation which is a major cause of cardiac graft failure. FIGS. 72A-72O show the histological differences between a normal vein, an arterialised vein and a failed vein graft.

Aterio-Venous (AV) Fistula

AV Fistulae are surgically created anastomosis between the arterial and venous circulation to enable the treatment of end stage kidney disease (ESKD) with dialysis. Patients with a working AVE have lower morbidity and mortality rates, and lower treatment costs compared to patients who rely on central venous catheters for dialysis. There is an unacceptable high rate of primary failure with AVF creation ranging from 20 to 60%. The failure rate had risen in recent years due to the ageing population dependent on AVE for dialysis and the higher pump speeds used in dialysis [19].

The main cause of failure is stenosis at the venous segment of the anastomosis. The underlying mechanisms involved in AVF creation are poorly understood but insufficient outward remodelling and excessive intimal hyperplasia are thought to be involved. Accordingly, an improved way of forming an AVE for use in ESKD patients is urgently needed. In one aspect of the present disclosure a helical coil with reduced abrasiveness or partially abrasive is used prior to the surgery for creation of the anastomosis to produce a vein with a healthy pattern of remodelling. This procedure should ideally be performed 4 to 12 weeks in advance of AVE creation to allow cellular changes to occur and subside. This preconditioning of the vein could reduce the inflammatory response and uncontrolled remodelling which leads to AVE primary failure when a normal vein is acutely exposed to arterial pressures and flow rates. This could increase the success rate of AVE procedures. This technique may also prevent AVF Steal syndrome whereby the venous side of the anastomosis becomes overly enlarged and leads to ischaemia in the territories supplied by the arterial side.

Thrombectomy

Thrombotic occlusions can occur anywhere in the arterial or venous system and are typically composed of red blood cells, activated clotting factors, platelets and inflammatory cells. Over time from minutes to days the thrombotic mass becomes organised and adherent to the vessel wall especially if there is vessel wall damage. Previously described embodiments of the present disclosure were designed to promote this event when vessel occlusion is required, primarily in the setting of the superficial venous reflux.

The authors have also discovered that a radially expansive helical coil can also be used to remove adherent thrombus to the vessel wall if the abrasive surface is modified to be only present on the leading edge and inner surface of the coil while the outer surface remains smooth to prevent vein wall trauma.

Acute deep vein thrombosis (DVT) is a potentially life-threatening condition if embolisation to the lungs occurs known as pulmonary embolism (PE). Significantly large DVTs remaining in the peripheral veins can also lead to significant morbidity from chronic venous hypertension in the lower limb. Anticoagulation is the cornerstone of treatment to help dissolve clots and prevent embolisation. New methods to treat patients in the acute setting by removal of the clot using mechanical, chemical lysis or ultrasound techniques have emerged in the past 10 years and shown to improve outcomes in certain patient groups. Removing clot which has become adherent to the vein wall is technically difficult and failure can lead to poorer outcomes. Some newer technologies which use complex mechanical systems, aspiration or ultrasound are not reimbursed due to their high cost. A fogarty balloon is a low-cost alternative to thrombus removal but is ineffective for adherent thrombi.

Figure 73:
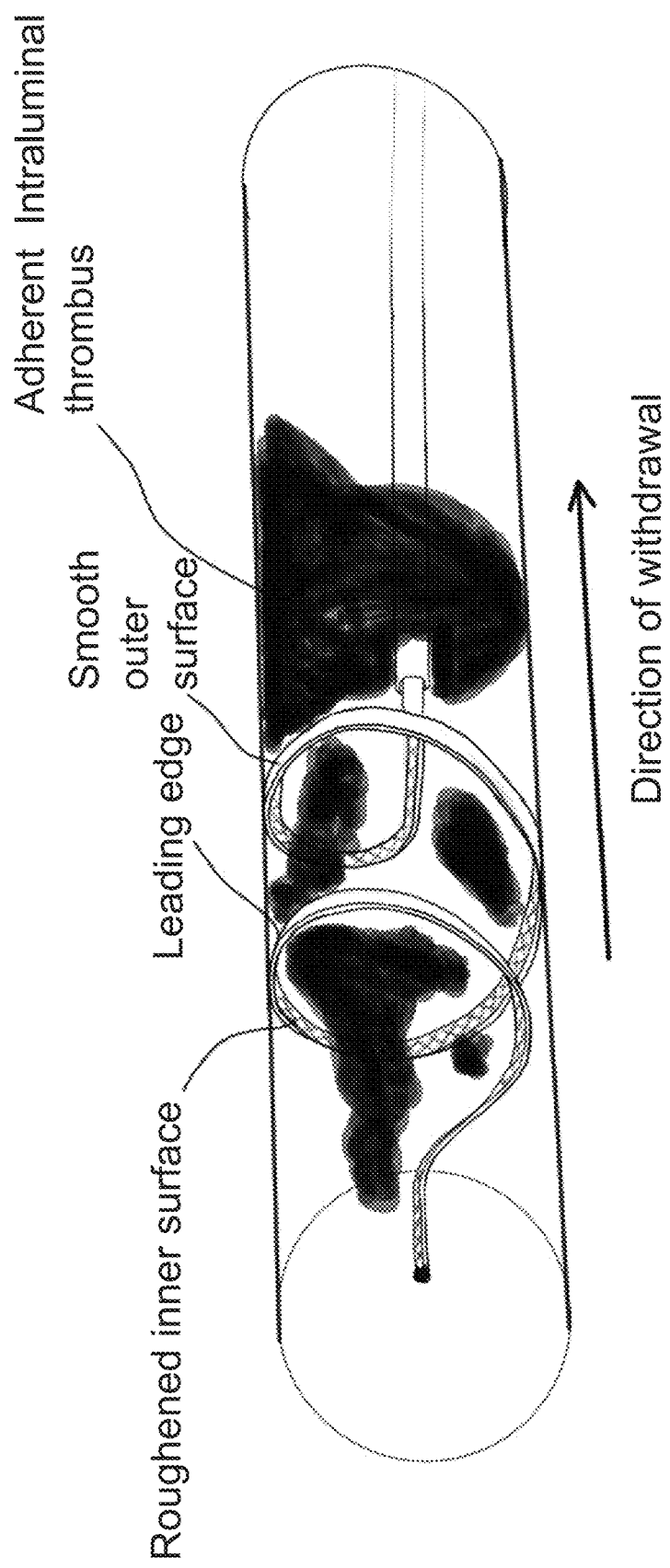
FIG. 73 illustrates the use of helical coil with roughened inner surface and smooth outer surface to remove an adherent thrombus in a blood vessel.

In the arterial system a similar need exists for the removal of an organised thrombus causing acute limb ischaemia. In the neurovascular system stent recapture systems are used to retrieve thrombus and prevent stroke. In both these settings more organised, adherent thrombus represents a technical challenge. There is therefore a need to develop improved solutions for removal of adherent clot or thrombus on vessel walls. In one embodiment a method is provided for using a helical coil with abrasive inner and leading-edge surfaces to dislodge thrombus from the vessel wall without causing endothelial trauma. FIG. 73 shows how such a device can remove thrombus while leaving the endothelial surface intact and less likely to re-thrombose.

The device is deployed distal to the thrombotic occlusion and withdrawn proximally towards the access site. Following dislodgement of the thrombus a fogarty balloon, recapturing basket or aspiration catheter can be used to remove the thrombus from the circulation. This will restore blood flow and prevent the sequelae of vessel occlusion occuring.

In-Stent Occlusion

Figure 74:
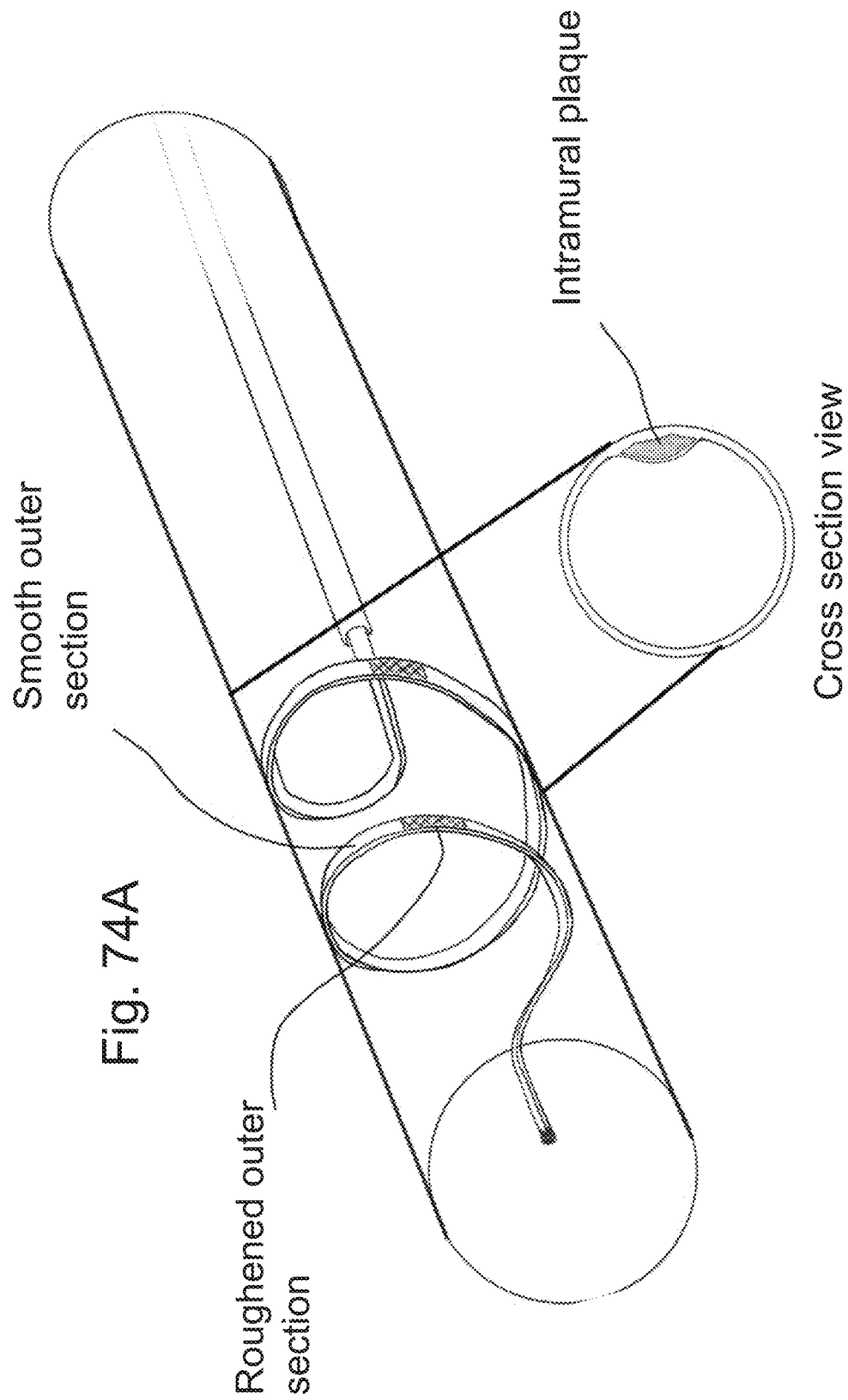
FIG. 74A and FIG. 74B illustrate the use of a helical coil with a partially textured outer surface allowing selective treatment of a vessel wall with or without rotational force in addition to axial withdrawal

Percutaneous stenting of the vasculature is commonly performed to reinstate blood flow in partially stenosed or occluded arterial or venous circulation. In-stent thrombosis is a relatively uncommon but potentially life threatening complication occurring after approximately 1% of cardiac stent procedures. Stents placed in diseased arteries may have struts overlying calcified or atheromatous plaques. Elevated stents struts in these situations can lead to a failure of coverage by the neointima especially in drug eluting stents [20]. This typically manifests as late or very late onset stent thrombosis over 1 year following implantation. There is a need to reduce the rate of in-stent thrombosis following such procedures. In one aspect of the present disclosure a helical coil with an outer abrasive surface that covers part of the coil circumference is provided. This allows selective treatment of a section of arterial surface which is likely to remain uncovered following statement. FIGS. 74A and 74B illustrate the method of using a partial abrasive coil to selectively pre-treat a section of artery prior to stent placement. This increases the likelihood of stent strut coverage by the neointima and reduces the risk of late stent restenosis. Imaging technologies such as intravascular ultrasound (IVUS) can be used to orientate the device and allow the operator to selectively target a desired section of vessel wall.

Arterial Occlusion

Selective occlusion of arteries and in general the arterial supply to specific tissues is an effective treatment for a variety of disease states. Tumour embolisation is a technique in which arteries supplying either benign or malignant tumours are occluded using a variety of methods via a percutaneous approach including synthetic or bioabsorbable beads, metallic spheres, glue or metallic coils. Common complications with the use of these agents include migration to non-target vessels, excessive occlusion causing necrosis of normal tissues, pain, infection related to combination of foreign body with necrotic tissue [21]. Accordingly, there is a need for a less invasive, non-implantable treatment with lower complication rates for the embolisation of arteries supplying benign or malignant tumours.

Referring to FIGS. 52A and 52B, these is illustrated a tumour 240 and an arterial blood supply to the tumour comprising small arteries 241. The device of the present disclosure may be employed to occlude one of the small arteries and starve the tumor of blood supply. FIG. 52B shows the vein denuding head 242 of a device of the present disclosure shown deployed in a small artery, where the helical coil circumferentially engages a lumen of the artery. Referring to FIG. 52A, the device is advanced along the artery feeding the tumor, and deployed at the point 243, and then retracted proximally. The retraction of the helical coil along the artery, coupled with the circumferential contact between the roughened surface of the helical coil and the lumen of the artery, causes a section of the lumen of the artery to be denuded with removal of the epithelial layer of cells, and consequent thrombus formation at point 243 resulting in occlusion of the artery.

Uterine Fibroids

Uterine fibroids are benign lesions which can cause significant pelvic pain and dysmenorrhea. They can be treated by hysterectomy or with minimally invasive embolisation of the uterine arteries supplying the fibroid. The most commonly used embolic agents for uterine artery embolisation (UAE) are polyvinyl alcohol (PVA), tris-acryl gelatin microspheres, and polyzene-F hydrogel microspheres. Complications include migration of embolic material to non-target tissues, excessive necrosis causing pain and infection. Accordingly, there is a need for a less invasive, non-implantable treatment with lower complication rates for the treatment of uterine fibroids. In one embodiment a method is provided for the use of a helical coil with abrasive outer surface to cause partial or full occlusion of the uterine artery or distal branches supplying a uterine fibroid. Reducing or eliminating blood flow decreases the size and relieves symptoms caused by the fibroid. Causing sufficient stenosis of the vessel using this method by inducing intimal hyperplasia may reduce the risk of necrotic complications while preserving the size reduction effect on the fibroid. This method could also be used to treat the following conditions which include but are not limited to; arteriovenous malformations (AVMs) in the pulmonary, cerebral or hepatic circulation, malignant tumours, benign prostatic hypertrophy (by prostatic artery occlusion).

Patent Foramen Ovale

Patent foramen ovale (PFO) is a common cardiac wall abnormality found in approximately 30% of the adult population. While usually a benign finding in some the PFO can open enabling a paradoxical embolus to travel from the venous to arterial circulation potentially causing stroke and systemic embolisation. The treatment in individuals with a history of cryptogenic stroke is percutaneous closure using septal occluders. These devices are permanent implants deployed across the defect. The anatomy of a PFO involves the overlapping of the primum and secundum atrial septa which form a flap valve that can open when the right atrial pressure exceeds the left atrial pressure such as in coughing or sneezing. These devices are expensive and can cause complication including thrombosis and stroke. There is a need for a less invasive treatment with lower risk of complications. In one embodiment a method is provided for the use of a coil or hooped shaped abrasive device to denude the contacting surface of the atrial septal flaps involved. This leads to an inflammatory response which cause adhesion formation between the flap surfaces leading to permanent closure of the PFO and elimination of stroke risk. A similar method could be used within the heart to create scar tissue and thickening to block nerve conduction at points of aberrant conduction which cause arrhythmias.

Patent Ductus Arteriosus

The ductus arteriosus (DA) is a fetal vascular connection between the main pulmonary artery and the aorta that diverts blood away from the pulmonary bed. After birth, the DA undergoes active constriction and eventual obliteration. A patent ductus arteriosus (PDA) occurs when the DA fails to completely close postnatally. Histologically, ductal tissue differs from that of the adjacent aorta and pulmonary artery. The intima of the ductus is thicker, and the media contains more smooth muscle fibers arranged in a characteristic spiral fashion. The DA may take a variety of shapes and forms. Small PDAs are typically <3 mm in diameter. The optimal treatment method for infants with a PDA necessitating closure remains a subject of controversy and debate. Current percutaneous treatment options include coils and occlusion devices. Limitations of these treatments include the high cost and risk of coil migration causing embolic complications. Occlusion devices can lead to serious complications such as coarctation of the aorta as the child grows if not sized correctly [22]. Accordingly, there is a need for less invasive effective percutaneous treatments for PDA. In one embodiment a helical coil with an outer abrasive surface is used to denude the DA causing thrombosis and fibrotic occlusion over time. This would relieve symptoms associated with shunting and reduce the risk of endocarditis by closing the DA. This technique could also be used to treat small diameter atrial septal defects in a similar manner.

Aortic Aneurysms

Abdominal aortic aneurysms (AAAs) are abnormal dilatations of the aorta which can be complicated by rupture causing significant morbidity and mortality. Treatment for large aneurysms is aimed at reducing the risk of rupture. Treatment options are either open surgery with graft placement or endovascular aneurysm repair using large covered stent grafts (EVAR). EVAR is a less invasive procedure with significantly faster recovery time and lower risk of renal injury. However, the long term outcomes of EVAR are limited by endoleaks in up to 20% of patients, requiring radiological monitoring, revision surgery or adjunctive procedures [23]. Endoleaks can be classified as Type I to Type V. Type I endoleaks occur at the proximal or distal graft attachment sites. Blood enters through gaps between the vessel wall and the graft and fills the sac leading to a risk of rupture. Type II endoleaks occur when retrograde flow occurs into the aneurysmal sac via side branches from lumbar or mesenteric vessels and also leads to a risk of rupture. Type I and II endoleaks account for the majority of morbidity associated with the EVAR post-operative course. Current treatment methods for Type I endoleaks include miniature screws and additional stent graft placements. Type II endoleaks can be treated with embolisation coil placement in the lumbar or mesenteric vessels supplying the sac. All of these methods are invasive, costly and carry complications of aortic wall rupture and infection. Accordingly, there is a need for techniques to reduce the risk of Type I and Type II endoleaks. In one embodiment a method is provided for preparing sections of the aorta close to graft attachment sites to reduce the risk of Type I endoleaks. This is performed by using a helical coil to denude the endothelial lining in these specific locations whose locations can be easily determined based on preoperative imaging planning. By performing this procedure, the arterial wall is primed to develop a neointimal proliferation at the graft attachment site and reduce the risk of blood leakage and Type I endoleaks. This benefit will reduce the risk of adjunctive procedures which can complicate the post-operative course. A similar method could be used to treat Type I endoleaks as they occur by inserting an expandable resilient abrasive device in the gap where the endoleak is occurring to cause thrombotic occlusion with fibrotic transformation over time. A further method is provided for the treatment of Type II endoleaks by using an expansive resilient abrasive element to denude the feeding lumbar or mesenteric arteries causing occlusion and preventing the risk of sac rupture. As the flow in these arteries is retrograde from anastomotic connections, they are more likely to behave like veins and be amenable to thrombotic occlusion with the permanent implantation of coils. A similar method could be used to treat paravalvular leaks associated with percutaneous heart valve replacement. Paravalvular leaks post percutaneous mitral and aortic valve replacement procedures leads to postoperative morbidity and in some cases revision surgery.

Diabetes Intervention Treatment

Duodenal Mucosal resurfacing (DMR) is a new technique that has been shown to improve blood glucose control in diabetic patients in early clinical studies [24]. The duodenum is an important conduit for glucose absorption and signalling to endocrine organs. It is thought that the duodenal mucosa becomes hyperplastic in response to chronic high sugar diets which creates an insulin-resistant signal, worsening glucose control. By ablating this hyperplastic mucosa, a new mucosal surface can regenerate without harmful signalling.

The anatomy of the duodenum shares some important characteristics with the venous system. It has a tortuous curved pathway, it is highly compliant and distensible and muscular wall contractions can cause constriction. The aim of treatment is to safely ablate only the superficial mucosal layer without affecting the deeper muscularis layer below. This is performed over the length of the duodenum of approximately 10 cms.

Figure 75:
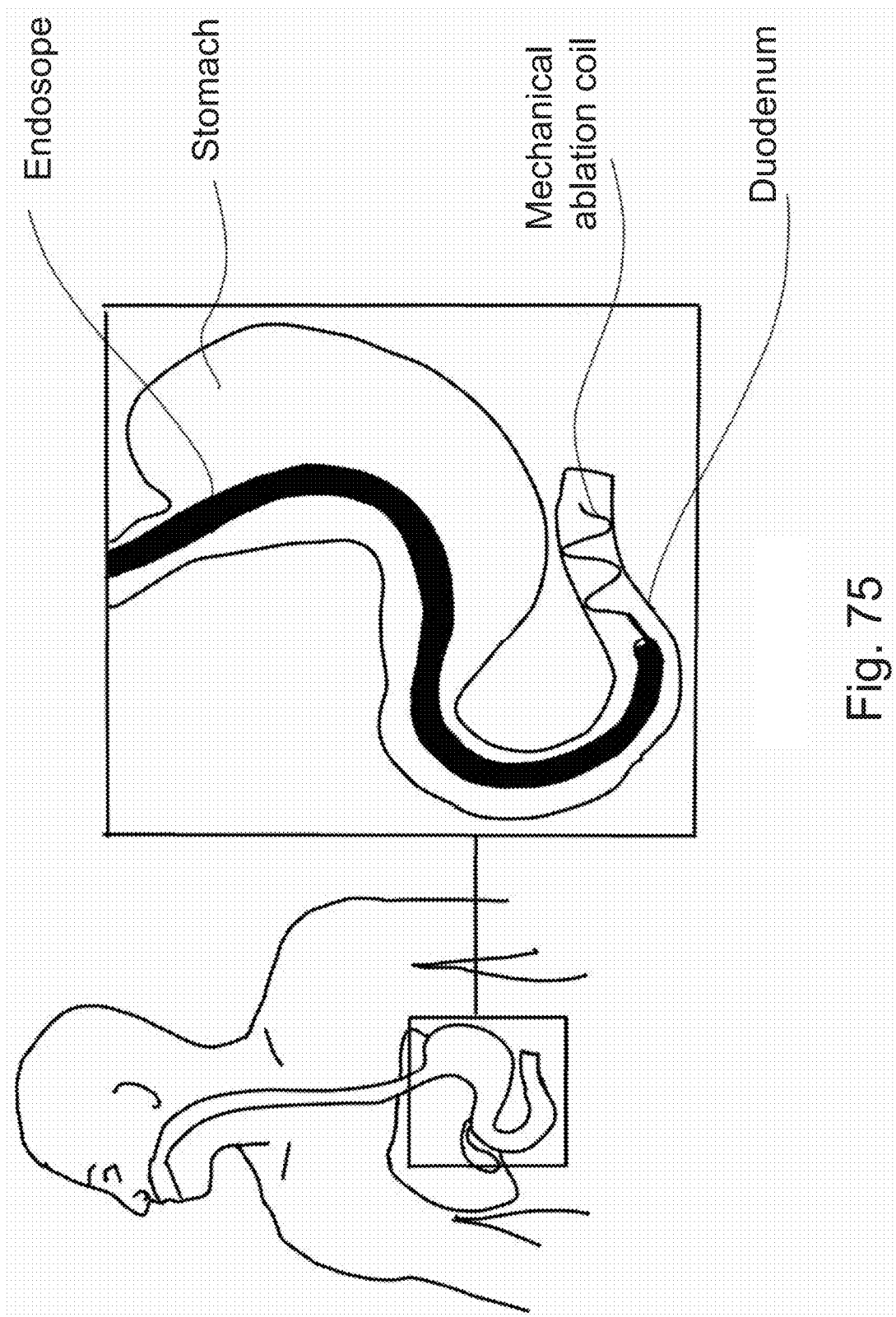
FIG. 75 illustrates the use of a helical coil during an endoscopy procedure to resurface the mucosal layer of the duodenum in the treatment of diabetes.

Current methods in development involve placing an expandable balloon capable of transmitting hydrothermal energy from fluid within the balloon to the duodenal wall and thus causing ablation or damage to the cells on the mucosal lining [22]. This method requires a skilled endoscopist to create a thermal barrier by lifting the mucosa away from the submucosa. This is currently achieved by suction channels around the circumference of the balloon to hold the superficial mucosa layer while a needle is inserted submucosally to inject saline. There is a risk of duodenal wall perforation and damage to deeper muscularis layer if this is not performed correctly. Accordingly, there is a need for a less invasive, easier to perform, lower cost and faster treatment which can selectively ablate the superficial layers of the duodenum to a depth of no greater than 0.6 mm. In one embodiment of the present disclosure a radially expansive resiliently deformable abrasive device is delivered via a channel in a standard endoscope as illustrated in FIG. 75. The abrasive element is deployed to contact the duodenal wall distally near the junction with the jejunum. The abrasive element has a surface roughness with maximum peak to trough distance of 0.6 mm. The device is withdrawn proximally towards the stomach. During withdrawal it causes a circumferential denudation or damage to the mucosal layer. This allows regeneration and improvement of glucose control. A similar method could be employed in other parts of the gastrointestinal tract to treat pathologies affected by the absorption of lipids, iron, vitamins and minerals including manganese.

Small Intestinal Bacterial Overgrowth

Small intestinal bacterial overgrowth (SIBO) occurs when the small bowel is colonised by excessive microbes that are normally present in the colon. Invasive bacterial strains injure the intestinal surface by the production of enterotoxins and through direct wall adherence. Fermentation of unabsorbed carbohydrates results in bloating, distension, and flatulence. Inflammation or the ileum can also occur causing diarrhoea and malabsorption of nutrients. The small bowel (jejunum and duodenum) normally has significantly lower concentrations of bacteria and other micro-organisms compared to the colon. The boundary between these sections of the gastrointestinal tract is controlled by the ileocaecal valve. When this valve becomes incompetent it can allow the reflux of large bowel contents into the small bowel. This encourages bacterial overgrowth which feeds off the nutrient rich contents of the small intestine [25]. Antibiotic treatment to stop bacterial overgrowth in the small bowel is currently used in primary treatment. However, approximately 40 percent of patients with small intestinal bacterial overgrowth (SIBO) have persistent symptoms after initial antibiotic treatment. It has been demonstrated that abnormal reflux through the ileocaecal valve is a causative factor in SIBO [25]. Accordingly, there is a need for more effective treatments for SIBO. In one embodiment a radially expandible abrasive device is used to disrupt the mucosal layers of the ileocaecal valve and ileum. This causes an inflammatory response followed by hyperplasia which could reduce the diameter of the ileocecal valve making it less likely to allow reflux of fluid from the colon. A secondary effect could be to ablate the areas of the ileum colonised by adherent bacteria to allow regeneration of normal or non-colonised mucosa. This method could be used in conjunction with antibiotic therapy to enhance the effect and lower the high recurrence rates. A similar method could be used to tighten the gastro-oesphageal junction which can be the cause of gastric reflux in the presence of sphincter laxity.

Barrett's Oesphagus

Barrett's esophagus (BE) is a premalignant condition for oesphageal carcinoma whereby cell changes in the lower oesphagus occur due to chronic injury and inflammation due to gastro-oesphageal reflux disease (GORD). It is estimated to be present in 10% of GORD patients. Early intervention can prevent progression to cancer. Current early intervention methods include thermal and radiofrequency ablation of the superficial layers affected to allow regeneration with normal tissue [26]. Radiofrequency ablation is a currently used technique involving endoscopic insertion of a radiofrequency probe. The main disadvantage of this method is the high cost of the radiofrequency device. Accordingly, there is a need for simpler, cost effective treatments for this common condition. In one embodiment a method is provided for the endoscopic deployment of radially expansive abrasive element to mechanically ablate the abnormal cells in the lower oesphagus thus reducing the risk of cancer development. Given that the histological grading and definitive diagnosis of Barrett's oesphagus is highly challenging for pathologists, a further advantage of this method is that it allows collection of cells on the denuding head which can be analysed post procedure. This is in contrast to thermal methods which completely destroy cells. This function of cell collection could also be applied to the diagnosis and management of premalignant or malignant lesions in other parts of the gastrointestinal tract such as the colon, pulmonary bronchi and bronchioli, uterus, cervix, urinary tract and bladder.

Peri-Anal Fistulae Management

Perianal fistulae are abnormal connections between the rectum and the skin surrounding the anal canal. They are a present in patients with inflammatory bowel disease and lead to significant morbidity due to infection, pain and bleeding. They are difficult to treat with current methods including invasive surgical resection or application of a seton stitch to gradually remove the channel over a long term treatment course. These treatment options carry a high recurrence rate [27]. Accordingly, there is a need to develop a less invasive more effective treatment for perianal fistuale. In one embodiment a radially expansive abrasive device is provided for deployment and withdrawal in the fistual tract. This caused denudation of the tract which is lined with endothelial cells. The subsequent inflammatory reaction causes scarring and blockage of faecal contents from entering the tract and preventing healing. Subsequent closure of the tract by a fibrotic inflammatory reaction prevents symptoms. A similar method could be used to seal or close sections of disease lung that occur in chronic obstructive lung disease. When inhaled air enters these parts of the disease lung oxygen exchange does not occur leading to a reduction in blood oxygen levels. There is a need to occlude or seal bronchioli or alveoli in these instances to divert air to healthy lung tissue.

Sterilisation

Female sterilisation is commonly performed by fallopian tube ligation when permanent contraception is desired by the patient. Current methods range from open surgical ligation, salpingectomy and minimally invasive clip placement. Complications of these procedures include pain, bleeding and infection. A less invasive reliable method which avoids surgical resection or permanent implantation is required. In one embodiment a radial expansive helical device is inserted, deployed and withdrawn in the fallopian tube. This disrupts the endothelial and subendothelial layers initiating an inflammatory response causing fibrotic occlusion of the fallopian tube over time. This technique could also be applied to male sterilisation procedures on the lumen of the vas deferens.

FIGS. 52A to 55 illustrate uses of the device of the present disclosure to occlude various vessel in the treatment of disease in a subject.

Referring to FIGS. 53A and 53B, the use of the device of the present disclosure to occlude the portal venous system is illustrated. This treatment may be employed to treat liver cancers, by occlusion of parts of the portal vein system which bring nutrients from the intestines 254 to the liver. In the figures, a vessel denuding head 252 is shown in a portal vein 251 in a deployed configuration. The retraction of the helical coil along the vein, coupled with the circumferential contact between the roughened surface of the helical coil and the lumen of the vein, causes a section of the lumen of the portal vein to be denuded with removal of the epithelial layer of cells, and consequent thrombus formation resulting in occlusion of the vein.

Referring to FIG. 54, there is illustrated a use of the device of the present disclosure to treat arteriovenous malformation, which is an abnormal tangle of blood vessels 261 connecting the venous 262 and arterial 263 blood vessels. In the embodiment illustrated, a device of the present disclosure is advanced along an artery and into the malformation, and the helical coil 264 is deployed into circumferential contact with the vessel 261 and retracted to denude the lumen of the vessel, causing thrombus formation and occlusion of the vessel 261, thereby shutting the shunt between the arterial and venous blood system.

Referring to FIG. 55, there is illustrated a use of the device of the present disclosure to treat spermatic vein insufficiency (or varicocele), which is a condition similar to varicose veins that occurs in the veins in the scrotum 272 and which can cause infertility, pain and discomfort for the patient. In the embodiment illustrated, a device of the present disclosure is advanced along a left internal spermatic vein 270, and the helical coil 271 is deployed into circumferential contact with the vein 270 and retracted to denude the lumen of the vessel, causing thrombus formation and occlusion of the vessel 270, thereby occluding the vein and treating the condition.

Figure 56C:
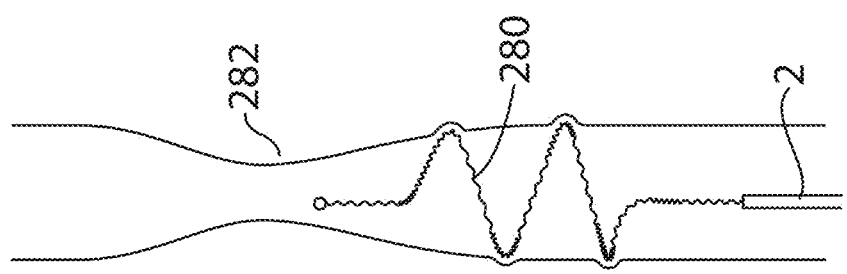
FIGS. 56A to 56C illustrate how the helical coil forming part of a device of the present disclosure can self-adapt to varying vessel diameter, and constrictions or narrowed sections in vessels, as it is pulled through the vessel: (A) the deployed helical coil in circumferential contact with the lumen of the vessel approaching the narrowed section of the vessel; (B) the helical coil having passed through the narrowed section and maintaining circumferential contact with the lumen of the vessel just proximal of the narrowed section; and (C) the helical coil moving proximally of the narrowed section and self-adjusting to maintain circumferential contact with the lumen of the vessel.
Figure 56B:
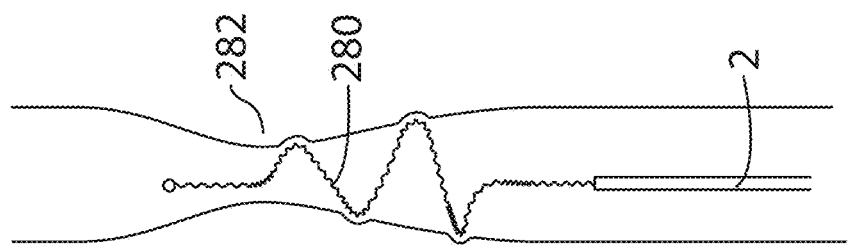
Figure 56A:
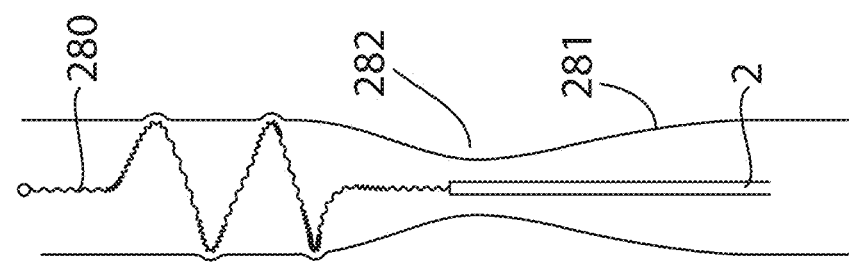

Referring to FIGS. 56A to 56C, the use of a device of the present disclosure, and in particular the ability of the device to self-adjust its diameter to adapt to vessels of varying diameter is illustrated. The coil is formed from nitinol, and in a relaxed state forms a helical coil having a diameter that is larger than the vessel to be treated. When the coil is deployed in a vessel (generally deployed from a delivery catheter), the catheter expands to conform to the circumference of the vessel, exerting an outward radial force against the circumference of the vessel through at least one turn of the coil. FIG. 56A shows the deployed helical coil 280 in a vessel 281 in circumferential contact with the lumen of the vessel approaching the narrowed section 282 of the vessel, with the diameter of the proximal part of the coil self-adjusting to the smaller diameter of the vessel. FIG. 56B shows the helical coil 280 having passed through the narrowed section 282 and maintaining circumferential contact with the lumen of the vessel just proximal of the narrowed section. FIG. 56C shows the helical coil moving proximally of the narrowed section and self-adjusting to maintain circumferential contact with the lumen of the vessel as it widens.

Figure 57C:
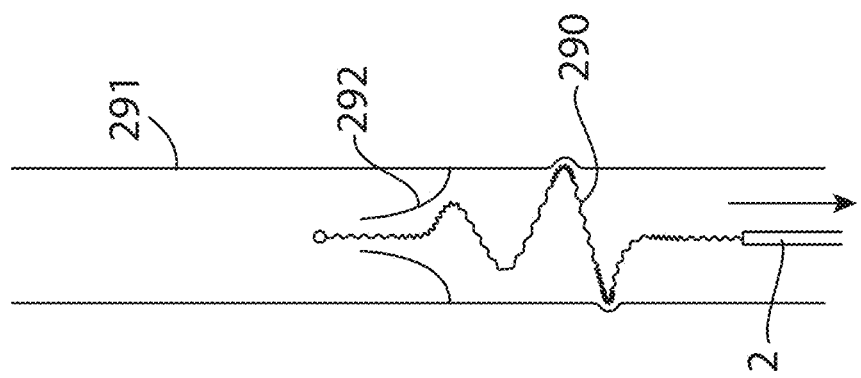
FIGS. 57A to 57C illustrate how the helical coil forming part of a device of the present disclosure can navigate through valves in veins as it is pulled through a section of a vein: (A) the deployed helical coil in circumferential contact with the lumen of the vein distal of the valve; (B) the helical coil passing through the valve without snagging; and (C) the helical coil moving proximally of the narrowed section and self-adjusting to maintain circumferential contact with the lumen of the vessel.
Figure 57B:
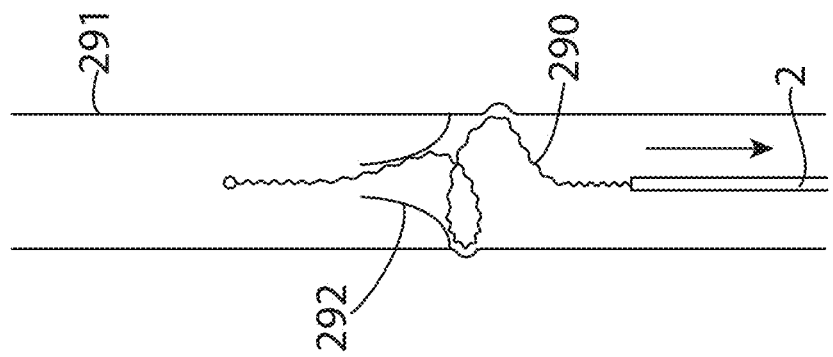
Figure 57A:
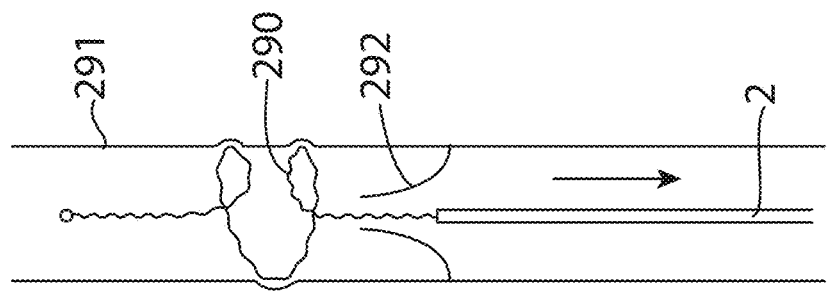

Referring to FIGS. 57A to 57C, the use of a device of the present disclosure is illustrated, in particular how the helical coil forming part of the device of the present disclosure can navigate through valves in veins as it is pulled through a section of a vein: (A) the deployed helical coil 290 attached to control arm 31 and in circumferential contact with the lumen of the vein 291 distal of the valve 292; (B) the helical coil 290 being retracted proximally through the valve 292 with the diameter of the coil self-adjusting to prevent the coil snagging on the valve leaflets; and (C) the helical coil moving proximally of the narrowed section and self-adjusting to maintain circumferential contact with the lumen of the vessel proximal of the valve.

Figure 58A:
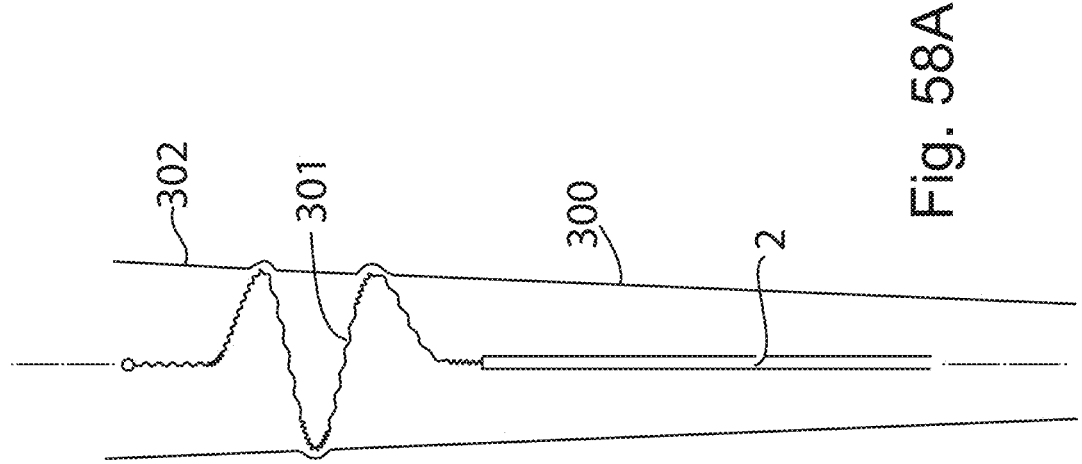
FIG. 58A and FIG. 58B illustrate how the helical coil forming part of a device of the present disclosure can navigate through a section of vasculature that progressively narrows and self-adjusts the diameter of the coil to maintain circumferential engagement with the lumen of the vessel: (A) the deployed helical coil in circumferential contact with a wide section of the vessel; (B) the deployed helical coil in circumferential contact with a narrower section of the vessel.
Figure 58B:
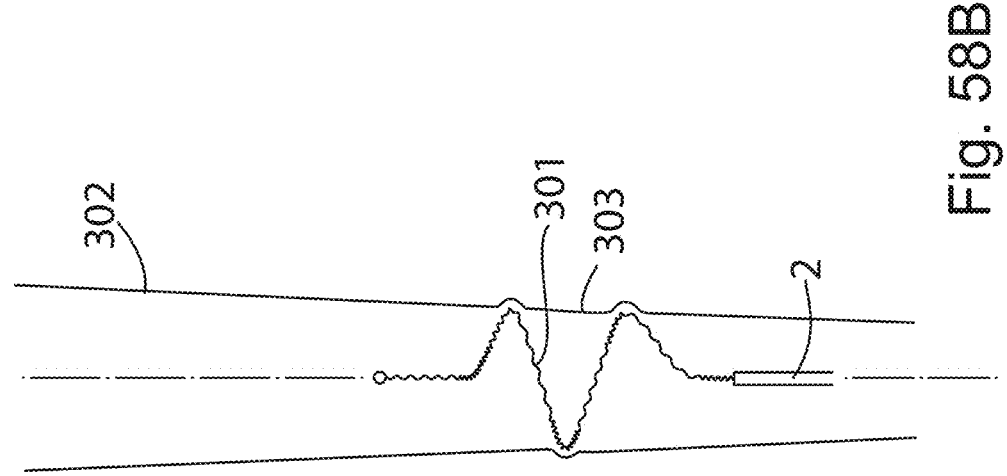

Referring to FIGS. 58A to 58B, the use of a device of the present disclosure is illustrated, in particular how the helical coil forming part of the device of the present disclosure can self-adjust to navigate through a section of vasculature 300 that progressively narrows with the diameter of the helical coil 301 self-adjusting to maintain circumferential engagement with the lumen of the vessel: (A) the deployed helical coil 301 in circumferential contact with a wide section 302 of the vessel; (B) the deployed helical coil 301 in circumferential contact with a narrower section 303 of the vessel;

Referring to FIGS. 59A to 59C, the use of a device of the present disclosure is illustrated, in particular how the helical coil forming part of the device of the present disclosure can self-adapt to varying vessel diameter and navigate a tortuous vessel: (A) the deployed helical coil 310 in circumferential contact with the lumen of the vessel at a narrowed section 311 of the vessel; (B) the helical coil 310 navigating through a sharp turn 312 in the vessel while maintaining circumferential contact with the lumen of the vessel; and (C) the helical coil 310 navigating through a second sharp turn 313 in the vessel of greater diameter while maintaining circumferential contact with the lumen of the vessel. It can be seen from the figures how the helical coil adapts to the changing diameter of the vessel and maintains circumferential contact with the lumen of the vessel, even as it passes through tortuous turns.

Referring to FIGS. 60A, 60B, and 60C, the use of a device of the present disclosure is illustrated, in particular how the helical coil forming part of the device of the present disclosure can self-adjust the diameter of the coil to maintain circumferential engagement with the lumen of the vessel when the vessel constricts due to a vasospasm: (A) the deployed helical coil in circumferential contact over length l within a wide vessel of diameter D prior to vasospasm of the vessel; (B) Section A-A illustrates an axial view of the coil within the vessel under a constraint pressure P which translates as a hoop force (HF) within the coil. This HF causes lengthening of the coil, promoted by its open ended design (C) the deployed helical coil in circumferential contact over an extended length L within constricted vessel of diameter d during a vasospasm of the vessel.

Figure 62B:
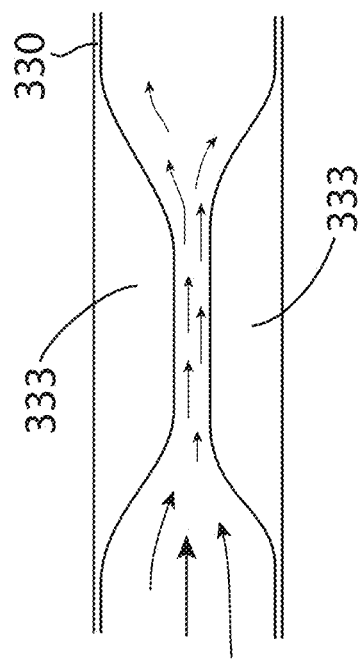
FIG. 62A and FIG. 62B illustrate how a device of the present disclosure can be used to treat vasculature having abnormally high blood volumes or high blood flow rates, to partially occlude the vessel to normalise the blood volume or flow: (A) shows a pulmonary artery prior to treatment, with the device deployed in the artery and being pulled proximally; (B) shows the chronic changes in the pulmonary artery of FIG. 62A after treatment with the device with intimal hyperplasia partially occluding (narrowing) the artery to provide for reduced blood volume and flow through the artery.
Figure 62A:
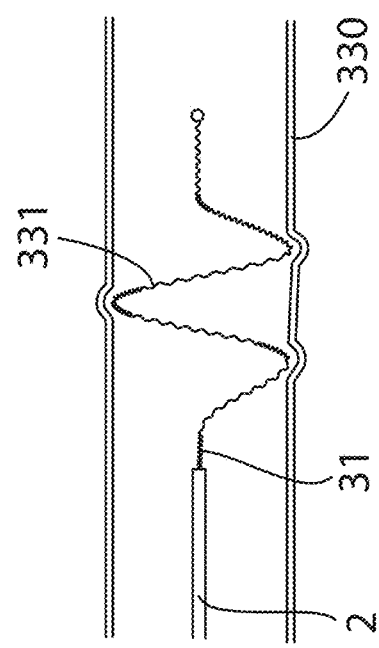

Referring to FIGS. 62A and 62B, the use of a device of the present disclosure to partially occlude a body lumen, and in the embodiment illustrated, to specifically treat vasculature having abnormally high blood volumes or high blood flow rates, to partially occlude the vessel to normalise the blood volume or flow. (A) shows a pulmonary artery 330 prior to treatment, with the device of the present disclosure including helical coil 331, control arm 31 and catheter member 2 deployed in the artery and being pulled in the direction of the arrow marked X; (B) shows the pulmonary artery of 330 after treatment with the device of the present disclosure with intimal hyperplasia of 333 partially occluding the artery to provide for reduced blood volume and flow through the artery.

Vessel Wall Evaluation

Understanding the biophysical properties of vessel walls in the arterial and venous system is important for both predicting disease progression and assessing the response to treatment.

Abnormalities in the vascular endothelium are now seen as early precursors of vascular disease [28]. One such marker is how well the vessel can contract or spasm in response to mechanical or chemical stimuli. Chronic high blood pressure and/or chronically uncontrolled blood sugar levels cause damage to the endothelial layer and can be detected at a much earlier stage than atherosclerosis, arterial stenosis or occlusion. Acetylcholine iontophoresis is a method of testing the endothelial response in conjunction with measuring blood flow across the section of vessel. These methods have shown experimentally that endothelial function is inhibited by consumption of sugar sweetened beverages and chronic high blood pressure states [29]. During vascular interventional procedures there is currently no way to assess endothelial cell function in or adjacent to artherosclerotic lesions. Accordingly, there is a need to collect more information on the function on the endothelium to inform treatment decisions and inform prognosis. During intravascular stent placement for instance there is currently no way for e physicians to know how the vessel wall is responding to expansion during angioplasty. This can lead to complications including vessel rupture, haemorrhage and thrombotic occlusion [30]. Currently the air pressure in the inflated balloon is measured and inflated to standard levels based on experience and angiographic appearance post inflation. However, due to differences in vessel wall characteristics and inter patient differences, occurrences of complications such as vessel wall rupture remain difficult to predict. In one embodiment a radial expandable element which contacts the vessel wall at discrete distant points is used to measure the response of the endothelium to chemical or mechanical stimuli. Mechanical stimuli can be provided by the radial force of the device itself which can be static or modifiable via a control arm. Chemical stimuli can be provided by coating of pharmacological agents on the device surface. In one embodiment piezoelectric sensors are incorporated into the radial expansive element to measure pressure and flow effects on the coil during intraluminal procedures. An expansive element within a vein lumen generating an outward radial force will cause a hoop force (HF) within the vessel wall. This stretching HF will cause an opposing compressive hoop force within the intra luminal device. Thus, measuring the intrinsic compression within the device will act as a surrogate marker to characterise the response of the vessel wall to stretch. This data can be recorded and stored in a central control unit. This data could be used for future performance enhancements including automation of procedures in the vascular system. This data could also be analysed either manually or by utilising machine learning methods to determine prognosis and validate diagnostic markers of vascular disease.

EQUIVALENTS

The foregoing description details presently preferred embodiments of the present disclosure. Numerous modifications and variations in practice thereof are expected to occur to those skilled in the art upon consideration of these descriptions. Those modifications and variations are intended to be encompassed within the claims appended hereto.

REFERENCES

1. Evans C J, et al. Prevalence of varicose veins and chronic venous insufficiency in men and women in the general population: Edinburgh Vein Study. J Epidemiol Community Health 1999
2. O'Donnell T F, et al. Assessment of thrombotic adverse events and treatment patterns associated with varicose vein treatment J Vasc Surg: Venous and Lym Dis 2015
3. Proebstle T. M, et al. Endovenous treatment of the greater saphenous vein with a 940-nm diode laser. Thrombotic occlusion after endoluminal thermal damage by laser-generated steam bubbles. J Vasc Surg 2005
4. Ikponmwosa A, et al. The Impact of Different Concentrations of Sodium Tetradecyl Sulphate and Initial Balloon Denudation on Endothelial Cell Loss and Tunica Media Injury in a Model of Foam Sclerotherapy Eur J Vasc Endovasc Surg 2010
5. Boersma D, et al. Macroscopic and Histologic Analysis of Vessel Wall Reaction After Mechanochemical Endovenous Ablation Using the ClariVein OC Device in an Animal Model. Eur J Vasc Endovasc Surg 2016
6. Lane T R, et al. Retrograde inversion stripping as a complication of the ClariVein® mechanochemical venous ablation procedure. Ann R Coll Surg Engl 2015
7. Rice J B, et al. Burden of venous leg ulcers in the United States. Journal of Medical Economics 2014
8. Gohel M S, et al. A Randomized Trial of Early Endovenous Ablation in Venous Ulceration. New Eng J Med 2018
9. Kerver A L, et al. The surgical anatomy of the small saphenous vein and adjacent nerves in relation to endovenous thermal ablation. J Vasc Surg 2012
10. Whiteley M, et al. Media Damage Following Detergent Sclerotherapy Appears to be Secondary to the Induction of Inflammation and Apoptosis: An Immunohistochemical Study Elucidating Previous Histological Observations. Eur J Vasc Endovasc Surg 2016
11. Chen Y M, et al. Study on the Sliding Friction of Endothelial Cells Cultured on Hydrogel and the Role of Glycocalyx on Friction Reduction. Advanced Engineering Materials 2010
12. Dimitrievska S, et al. New functional tools for anti-thrornbogenic activity assessment of live surface glycocalyx. Arterioscler Thromb Vasc Biol. 2016
13. Caggiati A, et al. Segmental hypoplasia of the great saphenous vein and varicose disease. Eur J Vasc Endovasc Surg 2004
14. Sanioglu S, et al. Mid-calf level as a puncture site is not safe enough for thermal ablation of the small saphenous vein. SAGE Open Medicine 2017
15. Proebstle T. M. et al. A two-cohort feasibility study on polyglycolic acid yarn implantation for abolition of saphenous vein reflux, J Vasc Surg: Venous and Lynn Dis 2018
16. Kwon S H, et al. Transcatheter ovarian vein embolization using coils for the treatment of pelvic congestion syndrome. Cardiovasc Intervent Radiol 2007
17. Zakharchenko A, et al. Safety and efficacy of superior rectal artery embolization with particles and metallic coils for the treatment of hemorrhoids (Emborrhoid technique) Diagnostic and Interventional Imaging 2016
18. Owens, C. D. Adaptive changes in autogenous vein grafts for arterial reconstruction: clinical implications. J. Vasc. Surg. 2010
19. Beathard G A, et al. Aggressive treatment of early fistula failure. Kidney International 2003
20. Oyabu J, et al. Angioscopic evaluation of neointima coverage: sirolimus drug-eluting stent versus bare metal stent. *Am Heart J.* 2006
21. Leyon J J, et al. Endovascular Embolization: Review of Currently Available Embolization Agents. Curr Probl Diagn Radiol, January/February 2014
22. Delaney J W, et al. Patent ductus arteriosus closure using the Amplatzer® vascular plug II for all anatomic variants. Catheter Cardiovasc Interv 2013
23. Avgerinos E D, Chaer R A, Makaroun M S. Type II endoleaks. J Vasc Surg 2014
24. Haidry R J, et al. Duodenal mucosal resurfacing: proof-of-concept, procedural development, and initial implementation in the clinical setting. Gastrointestinal Endoscopy 2019
25. Roland B C, et al. Low ileocecal valve pressure is significantly associated with small intestinal bacterial overgrowth (SIBO). Dig Dis Sci. 2014
26. Akiyama J, et al. Managing Barrett's esophagus with radiofrequency ablation. Gastroenterology Report 1 2013

27. Keogh K M, et al. The proposed use of radiofrequency ablation for the treatment of fistula-in-ano. Med Hypotheses 2016.
28. Boulanger C M,. et al. Highlight on Endothelial Activation and Beyond. Arterioscler Thromb Vasc Biol 2018
29. Loader J, et al. Effects of Sugar-Sweetened Beverage Consumption on Microvascular and Macrovascular Function in a Healthy Population. Arterioscler Thromb Vasc Biol 2017
30. Gruberg L, et al. Incidence, management, and outcome of coronary artery perforation during percutaneous coronary intervention. Am J Cardiol 2000

What is claimed is:

1. A vein denuding device comprising:
a coil configured for transluminal delivery to a vein to be treated during a procedure and deployment whereby the coil circumferentially engages an inner lumen of the vein and forms a completely open lumen devoid of any structure inside the coil,
the coil has a first planar side, a second planar side, a smooth internally facing surface, and an externally facing surface normal to the first and second side,
the externally facing surface is a roughened lumen-engaging surface, so that when the coil is deployed the externally facing, roughened lumen-engaging surface bears against the inner lumen of the vein,
the roughened lumen-engaging surface of the coil comprises a series of teeth, in which each tooth in the series of teeth has a triangular profile extending across the lumen-engaging surface of the coil from the first side of the coil to the second side of the coil and orthogonally to a longitudinal aspect of the coil,
whereby axial movement of the coil along the vein mechanically denudes a length of the vein with consequent disruption of endothelial and media layers of the vein.

2. A vein denuding device according to claim 1, configured to mechanically denude the vein to a depth of at least 5 μm and up to but not exceeding 100 μm.

3. A vein denuding device according to claim 1, in which the coil is oversized relative to a diameter of the vein being treated to ensure circumferential engagement between the roughened surface of the coil and lumen of the vein.

4. A vein denuding device according to claim 1, in which the coil is resiliently deformable to allow the coil to reflexively self-adjust its diameter in response to variable vessel diameters and variable axial forces during axial movement along a treatment zone of the vein while maintaining an outward radial force on the vein.

5. A vein denuding device according to claim 1, in which the coil is helical and is configured to have a pitch of about 0.5 to 1.5 times a coil diameter in a coiled configuration when deployed.

6. A vein denuding device according to claim 1, in which a distal end of the coil comprises an atraumatic head comprising a ball.

7. A vein denuding device according to claim 1, in which the coil comprises a shape memory material and is configured to adopt a coiled configuration when deployed.

8. A vein denuding device according to claim 1, including an elongated catheter member operatively attached to the coil, wherein the coil is adjustable from an uncoiled delivery configuration suitable for transluminal delivery within the catheter member and a coiled deployed configuration having a diameter equal to or greater than the vein to be denuded.

9. A vein denuding device according to claim 8, in which the device comprises an elongated control arm for the coil disposed within the catheter member.

10. A vein denuding device according to claim 1, in which a diameter of the coil varies along its length.

11. A vein denuding device according to claim 1, in which a diameter of the coil increases towards one end.

12. A vein denuding device according to claim 1, in which a diameter of the coil increases towards a proximal end.

13. A vein denuding device according to claim 1, in which a diameter of the coil increases towards a mid-point along the coil, and then decreases.

14. A vein denuding device according to claim 1, in which a distal tip of the coil terminates at a point disposed along, or adjacent to, a longitudinal axis of the coil.

15. A vein denuding device according to claim 1, in which the coil has a proximal section of a first diameter, an intermediate section of reduced diameter relative to the proximal section, and a distal section of increased diameter relative to the intermediate section.

16. A vein denuding device according to claim 1, in which the coil has a proximal and distal helical coil section, and an intermediate connecting section that is not helical and may be straight or curved.

17. A vein denuding device comprising a coil configured for transluminal delivery to a vein whereby the coil circumferentially engages an inner lumen of the vein, in which the device forms a completely open lumen devoid of any structure inside the coil, the coil has a first planar side, a second planar side, and a roughened lumen-engaging surface extending between the first and second planar sides, so that when it is deployed the roughened lumen-engaging surface bears against the inner lumen of the vein, in which the roughened lumen-engaging surface of the coil comprises a contiguous series of teeth such that an end of one tooth forms a beginning of an adjacent tooth along the entire coil, in which each tooth in the contiguous series of teeth includes a linear apex extending normal to the first and second planar sides, whereby axial movement of the coil along the vein mechanically denudes a length of the vein with consequent disruption of endothelial and media layers of the vein.

18. A vein denuding device according to claim 17, in which the linear apex extends transversely across less than an entire transverse section of coil.

19. A vein denuding device according to claim 17, in which each tooth extends across the lumen-engaging surface of the coil orthogonally to a longitudinal aspect of the coil.

20. A vein denuding device for transluminal delivery to a vein to be treated during a procedure and deployment whereby the device circumferentially engages an inner lumen of the vein, the device comprising:
a wire including a distal end, a proximal end, and a coil portion between the proximal end and distal end,
the coil portion having a completely open coil lumen devoid of any structure inside the coil lumen,
an inner surface, an outer surface, and first and second planar side surfaces extending between the inner and outer surfaces; and
the outer surface including a series of teeth, in which each tooth in the series of teeth has a linear apex extending normal to the first and second planar side portions and orthogonally to a longitudinal aspect of the coil.

21. A vein denuding device according to claim 20, wherein the series of teeth are contiguous.

22. A vein denuding device according to claim 21, wherein the inner surface of the coil is smooth.

23. A vein denuding device according to claim 22, wherein the coil includes at least two circumferential turns.

24. A vein denuding device comprising a coil configured for transluminal delivery to a vein whereby the coil circumferentially engages an inner lumen of the vein, in which the coil expands by itself to engage the inner lumen, and the coil has a completely open lumen devoid of any structure within the coil, and the coil has a roughened lumen-engaging surface, so that when it is deployed the roughened lumen-engaging surface bears against the inner lumen of the vein, in which the roughened lumen-engaging surface of the coil comprises a contiguous series of teeth such that an end of one tooth forms a beginning of an adjacent tooth along the coil, in which each tooth in the series of teeth comprises a linear aspect extending normal to a first and second planar sides, and extending orthogonally to a longitudinal aspect of the coil, and is configured to mechanically denude a length of the vein with consequent disruption of endothelial and media layers of the vein when the coil is moved axially along the vein.

25. A vein denuding device according to claim 24, in which the coil has a smooth internal surface.

26. A vein denuding device according to claim 24, in which each tooth has a triangular profile extending transversely across the lumen-engaging surface of the coil transversely to a longitudinal aspect of the coil.

* * * * *